United States Patent
Thommen et al.

(10) Patent No.: US 9,913,727 B2
(45) Date of Patent: Mar. 13, 2018

(54) EXPANDABLE IMPLANT

(71) Applicant: Medos International Sarl, Le Locle (CH)

(72) Inventors: Daniel Thommen, Oberdorf (CH); Joern Richter, Oberdorf (CH); Peter Senn, Oberdorf (CH)

(73) Assignee: Medos International Sarl, Le Locle (CH)

( * ) Notice: Subject to any disclaimer, the term of this patent is extended or adjusted under 35 U.S.C. 154(b) by 230 days.

(21) Appl. No.: 14/790,866

(22) Filed: Jul. 2, 2015

(65) Prior Publication Data

US 2017/0000622 A1    Jan. 5, 2017

(51) Int. Cl.
*A61F 2/44* (2006.01)
*A61F 2/30* (2006.01)

(52) U.S. Cl.
CPC ............ *A61F 2/4425* (2013.01); *A61F 2/447* (2013.01); *A61F 2002/3055* (2013.01); *A61F 2002/30556* (2013.01); *A61F 2002/443* (2013.01); *A61F 2250/0008* (2013.01)

(58) Field of Classification Search
CPC ............................... A61F 2/4425; A61F 2/447
See application file for complete search history.

(56) References Cited

U.S. PATENT DOCUMENTS

| | | |
|---|---|---|
| 1,802,560 A | 4/1931 | Kerwin et al. |
| 2,077,804 A | 4/1937 | Monroe et al. |
| 2,121,193 A | 6/1938 | Hanicke |
| 2,173,655 A | 9/1939 | Neracher et al. |

(Continued)

FOREIGN PATENT DOCUMENTS

| | | |
|---|---|---|
| AU | 2005314079 | 10/2012 |
| CN | 1177918 | 4/1998 |

(Continued)

OTHER PUBLICATIONS

Hoogland, T. et al., Total Lumbar Intervertebral Disc Replacement: testing of a New Articulating Space in Human Cadaver Spines—24 1 Annual ORS, Dallas TX, Feb. 21-23, 1978, 8 pages.
Spine Solutions Brochure—Prodisc 2001, 16 pages.
Link SB Charite Brochure—Intervertebral Prosthesis 1988, 29 pages.
Alfen et al., "Developments in the Area of Endoscopic Spine Surgery", European Musculoskeletal Review 2006, pp. 23-24.
ThessysTM, Transforaminal Endoscopic Spine Systems, joi max Medical Solutions.

(Continued)

*Primary Examiner* — Zade Coley
*Assistant Examiner* — Olivia C Chang
(74) *Attorney, Agent, or Firm* — Baker & Hostetler LLP

(57) ABSTRACT

An intervertebral implant includes a frame including an end member and an intermediate member pivotally coupled to the end member about a first pivot axis. The intervertebral implant includes a first vertebral contact member pivotally coupled to the frame about a second pivot axis that is substantially perpendicular to the first pivot axis, and a second vertebral contact member coupled to the frame. The frame is configured such that pivoting the intermediate member with respect to the end member about the first pivot axis changes both a width between the first vertebral contact member and the second vertebral contact member with respect to a direction that is substantially parallel to the second pivot axis, and changes a height between the first vertebral contact member and the second vertebral contact member with respect to a direction that is substantially parallel to the first pivot axis.

20 Claims, 20 Drawing Sheets

(56) References Cited

U.S. PATENT DOCUMENTS

| | | |
|---|---|---|
| 2,243,717 A | 5/1941 | Godoy et al. |
| 2,381,050 A | 8/1945 | Hardinge et al. |
| 2,388,056 A | 10/1945 | Hendricks et al. |
| 2,485,531 A | 10/1949 | William et al. |
| 2,489,870 A | 11/1949 | William et al. |
| 2,570,465 A | 10/1951 | Lundholm et al. |
| 2,677,369 A | 5/1954 | Knowles et al. |
| 3,115,804 A | 12/1963 | Lee et al. |
| 3,312,139 A | 4/1967 | Di et al. |
| 3,486,505 A | 12/1969 | Morrison et al. |
| 3,489,143 A | 1/1970 | Halloran et al. |
| 3,698,391 A | 10/1972 | Mahony et al. |
| 3,760,802 A | 9/1973 | Fischer et al. |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,867,728 A | 2/1975 | Stubstad et al. |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,175,555 A | 11/1979 | Herbert |
| 4,236,512 A | 12/1980 | Aginsky |
| 4,262,665 A | 4/1981 | Roalstad et al. |
| 4,275,717 A | 6/1981 | Bolesky |
| 4,312,353 A | 1/1982 | Shahbabian |
| 4,341,206 A | 7/1982 | Perrett et al. |
| 4,349,921 A | 9/1982 | Kuntz |
| 4,350,151 A | 9/1982 | Scott |
| 4,369,790 A | 1/1983 | McCarthy |
| 4,401,112 A | 8/1983 | Rezaian |
| 4,401,433 A | 8/1983 | Luther |
| 4,409,974 A | 10/1983 | Freedland |
| 4,449,532 A | 5/1984 | Storz |
| 4,451,256 A | 5/1984 | Weikl et al. |
| 4,456,005 A | 6/1984 | Lichty |
| 4,463,753 A | 8/1984 | Gustilo |
| 4,488,543 A | 12/1984 | Tornier |
| 4,494,535 A | 1/1985 | Haig |
| 4,532,660 A | 8/1985 | Field |
| 4,537,185 A | 8/1985 | Stednitz |
| 4,545,374 A | 10/1985 | Jacobson |
| 4,573,448 A | 3/1986 | Kambin |
| 4,601,710 A | 7/1986 | Moll |
| 4,625,725 A | 12/1986 | Davison et al. |
| 4,629,450 A | 12/1986 | Suzuki et al. |
| 4,632,101 A | 12/1986 | Freedland |
| 4,640,271 A | 2/1987 | Lower |
| 4,641,640 A | 2/1987 | Griggs |
| 4,653,489 A | 3/1987 | Tronzo |
| 4,667,663 A | 5/1987 | Miyata |
| 4,686,984 A | 8/1987 | Bonnet |
| 4,688,561 A | 8/1987 | Reese |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Tormala et al. |
| 4,759,766 A | 7/1988 | Buettner-Janz et al. |
| 4,760,843 A | 8/1988 | Fischer et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,858,601 A | 8/1989 | Glisson |
| 4,862,891 A | 9/1989 | Smith |
| 4,863,476 A | 9/1989 | Shepperd |
| 4,871,366 A | 10/1989 | von Recum et al. |
| 4,873,976 A | 10/1989 | Schreiber |
| 4,878,915 A | 11/1989 | Brantigan |
| 4,898,186 A | 2/1990 | Ikada et al. |
| 4,903,692 A | 2/1990 | Reese |
| 4,917,554 A | 4/1990 | Bronn |
| 4,940,467 A | 7/1990 | Tronzo |
| 4,959,064 A | 9/1990 | Engelhardt |
| 4,963,144 A | 10/1990 | Huene |
| 4,966,587 A | 10/1990 | Baumgart |
| 4,968,317 A | 11/1990 | Tormala et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 5,002,557 A | 3/1991 | Hasson |
| 5,011,484 A | 4/1991 | Breard |
| 5,013,315 A | 5/1991 | Barrows |
| 5,013,316 A | 5/1991 | Goble et al. |
| 5,059,193 A | 10/1991 | Kuslich |
| 5,062,849 A | 11/1991 | Schelhas |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,114,407 A | 5/1992 | Burbank |
| 5,116,336 A | 5/1992 | Frigg |
| 5,120,171 A | 6/1992 | Lasner |
| 5,122,133 A | 6/1992 | Evans |
| 5,122,141 A | 6/1992 | Simpson et al. |
| 5,123,926 A | 6/1992 | Pisharodi |
| 5,139,486 A | 8/1992 | Moss |
| 5,158,543 A | 10/1992 | Lazarus |
| 5,167,663 A | 12/1992 | Brumfield |
| 5,167,664 A | 12/1992 | Hodorek |
| 5,169,400 A | 12/1992 | Muhling et al. |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,697 A | 1/1993 | Hasson et al. |
| 5,178,501 A | 1/1993 | Carstairs |
| 5,183,464 A | 2/1993 | Dubrul et al. |
| 5,188,118 A | 2/1993 | Terwilliger |
| 5,195,506 A | 3/1993 | Hulfish |
| 5,201,742 A | 4/1993 | Hasson |
| 5,217,462 A | 6/1993 | Asnis et al. |
| 5,217,486 A | 6/1993 | Rice et al. |
| 5,224,952 A | 7/1993 | Deniega et al. |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,246,441 A | 9/1993 | Ross et al. |
| 5,250,049 A | 10/1993 | Michael |
| 5,269,797 A | 12/1993 | Bonati et al. |
| 5,280,782 A | 1/1994 | Wilk |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,304,142 A | 4/1994 | Liebl et al. |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,324,261 A | 6/1994 | Amundson et al. |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,382,248 A | 1/1995 | Jacobson et al. |
| 5,387,213 A | 2/1995 | Breard et al. |
| 5,387,215 A | 2/1995 | Fisher |

(56) References Cited

U.S. PATENT DOCUMENTS

| | | |
|---|---|---|
| 5,390,683 A | 2/1995 | Pishardi |
| 5,395,317 A | 3/1995 | Kambin |
| 5,395,371 A | 3/1995 | Miller et al. |
| 5,401,269 A | 3/1995 | Buttner-Janz et al. |
| 5,407,430 A | 4/1995 | Peters |
| 5,415,661 A | 5/1995 | Holmes |
| 5,424,773 A | 6/1995 | Saito |
| 5,425,773 A | 6/1995 | Boyd et al. |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,790 A | 10/1995 | Dubrul |
| 5,464,427 A | 11/1995 | Curtis et al. |
| 5,470,333 A | 11/1995 | Ray |
| 5,472,426 A | 12/1995 | Bonati et al. |
| 5,474,539 A | 12/1995 | Costa et al. |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach, Jr. et al. |
| 5,505,710 A | 4/1996 | Dorsey, III |
| 5,507,816 A | 4/1996 | Bullivant |
| 5,512,037 A | 4/1996 | Russell et al. |
| 5,514,180 A | 5/1996 | Heggeness et al. |
| 5,520,690 A | 5/1996 | Errico et al. |
| 5,520,896 A | 5/1996 | de Graaf et al. |
| 5,522,899 A | 6/1996 | Michelson |
| 5,527,312 A | 6/1996 | Ray |
| 5,534,029 A | 7/1996 | Shima |
| 5,536,127 A | 7/1996 | Pennig |
| 5,540,688 A | 7/1996 | Navas |
| 5,540,693 A | 7/1996 | Fisher |
| 5,545,164 A | 8/1996 | Howland |
| 5,549,610 A | 8/1996 | Russell et al. |
| 5,554,191 A | 9/1996 | Lahille et al. |
| 5,556,431 A | 9/1996 | Buttner-Janz |
| 5,558,674 A | 9/1996 | Heggeness et al. |
| D374,287 S | 10/1996 | Goble et al. |
| 5,562,738 A | 10/1996 | Boyd et al. |
| 5,564,926 A | 10/1996 | Brånemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,591,168 A | 1/1997 | Judet et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,639,276 A | 6/1997 | Weinstock et al. |
| 5,643,320 A | 7/1997 | Lower et al. |
| 5,645,589 A | 7/1997 | Li |
| 5,645,599 A | 7/1997 | Samani |
| 5,647,857 A | 7/1997 | Anderson et al. |
| 5,649,931 A | 7/1997 | Bryant et al. |
| 5,653,763 A | 8/1997 | Errico |
| 5,658,335 A | 8/1997 | Allen |
| 5,662,683 A | 9/1997 | Kay |
| 5,665,095 A | 9/1997 | Jacobson |
| 5,665,122 A | 9/1997 | Kambin |
| 5,667,508 A | 9/1997 | Errico et al. |
| 5,669,915 A | 9/1997 | Caspar et al. |
| 5,676,701 A | 10/1997 | Yuan et al. |
| 5,683,465 A | 11/1997 | Shinn et al. |
| 5,693,100 A | 12/1997 | Pisharodi |
| 5,697,977 A | 12/1997 | Pisharodi |
| 5,702,391 A | 12/1997 | Lin |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,541 A | 3/1998 | Anspach, III et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,282 A | 4/1998 | Anspach, III et al. |
| 5,743,881 A | 4/1998 | Demco |
| 5,743,912 A | 4/1998 | Lahille et al. |
| 5,743,914 A | 4/1998 | Skiba |
| 5,749,889 A | 5/1998 | Bacich et al. |
| 5,752,969 A | 5/1998 | Cunci et al. |
| 5,762,500 A | 6/1998 | Lazarof |
| 5,762,629 A | 6/1998 | Kambin |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,792,044 A | 8/1998 | Foley et al. |
| 5,797,909 A | 8/1998 | Michelson |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,836,948 A | 11/1998 | Zucherman et al. |
| 5,846,259 A | 12/1998 | Berthiaume |
| 5,849,004 A | 12/1998 | Bramlet |
| 5,851,216 A | 12/1998 | Allen |
| 5,860,973 A | 1/1999 | Michelson |
| 5,860,977 A | 1/1999 | Zucherman et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,957,924 A | 9/1999 | Törmälä et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,976,139 A | 11/1999 | Bramlet |
| 5,976,146 A | 11/1999 | Ogawa et al. |
| 5,976,186 A | 11/1999 | Bao et al. |
| 5,980,522 A | 11/1999 | Koros et al. |
| 5,984,927 A | 11/1999 | Wenstrom, Jr. et al. |
| 5,984,966 A | 11/1999 | Kiema et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |

(56) References Cited

U.S. PATENT DOCUMENTS

| | | |
|---|---|---|
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke et al. |
| 6,007,519 A | 12/1999 | Rosselli |
| 6,007,566 A | 12/1999 | Wenstrom, Jr. |
| 6,007,580 A | 12/1999 | Lehto et al. |
| 6,010,513 A | 1/2000 | Tormala et al. |
| 6,015,410 A | 1/2000 | Törmälä et al. |
| 6,019,762 A | 2/2000 | Cole |
| 6,022,352 A | 2/2000 | Vandewalle |
| 6,030,162 A | 2/2000 | Huebner |
| 6,030,364 A | 2/2000 | Durgin et al. |
| 6,033,406 A | 3/2000 | Mathews |
| 6,036,701 A | 3/2000 | Rosenman |
| 6,039,761 A | 3/2000 | Li |
| 6,039,763 A | 3/2000 | Shelokov |
| 6,045,579 A | 4/2000 | Hochshuler |
| 6,048,309 A | 4/2000 | Flom et al. |
| 6,048,342 A | 4/2000 | Zucherman et al. |
| 6,053,935 A | 4/2000 | Brenneman et al. |
| 6,066,142 A | 5/2000 | Serbousek et al. |
| 6,068,630 A | 5/2000 | Zucherman et al. |
| 6,068,648 A | 5/2000 | Cole et al. |
| 6,074,390 A | 6/2000 | Zucherman et al. |
| 6,080,155 A | 6/2000 | Michelson |
| 6,080,193 A | 6/2000 | Hochshuler et al. |
| 6,083,244 A | 7/2000 | Lubbers et al. |
| 6,090,112 A | 7/2000 | Zucherman et al. |
| 6,096,038 A | 8/2000 | Micheson |
| 6,102,914 A | 8/2000 | Bulstra et al. |
| 6,102,950 A | 8/2000 | Vaccaro |
| 6,106,557 A | 8/2000 | Robioneck et al. |
| 6,113,637 A | 9/2000 | Gill et al. |
| 6,113,638 A | 9/2000 | Williams et al. |
| 6,117,174 A | 9/2000 | Nolan |
| 6,123,711 A | 9/2000 | Winters |
| 6,126,661 A | 10/2000 | Faccioli et al. |
| 6,126,663 A | 10/2000 | Hair |
| 6,127,597 A | 10/2000 | Beyar et al. |
| 6,129,762 A | 10/2000 | Li |
| 6,129,763 A | 10/2000 | Chauvin et al. |
| 6,146,384 A | 11/2000 | Lee et al. |
| 6,146,387 A | 11/2000 | Trott et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,161,350 A | 12/2000 | Espinosa |
| 6,162,234 A | 12/2000 | Freedland et al. |
| 6,162,236 A | 12/2000 | Osada |
| 6,168,595 B1 | 1/2001 | Durham et al. |
| 6,168,597 B1 | 1/2001 | Biedermann et al. |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,190,387 B1 | 2/2001 | Zucherman et al. |
| 6,193,757 B1 | 2/2001 | Foley et al. |
| 6,197,041 B1 | 3/2001 | Shichman et al. |
| 6,200,322 B1 | 3/2001 | Branch et al. |
| 6,206,826 B1 | 3/2001 | Mathews et al. |
| 6,206,922 B1 | 3/2001 | Zdeblick et al. |
| 6,213,957 B1 | 4/2001 | Milliman et al. |
| 6,217,509 B1 | 4/2001 | Foley et al. |
| 6,221,082 B1 | 4/2001 | Marino et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,238,397 B1 | 5/2001 | Zucherman et al. |
| 6,245,107 B1 | 6/2001 | Ferree |
| 6,248,108 B1 | 6/2001 | Tormala et al. |
| 6,251,111 B1 | 6/2001 | Barker et al. |
| 6,264,676 B1 | 7/2001 | Gellman et al. |
| 6,267,765 B1 | 7/2001 | Taylor et al. |
| 6,267,767 B1 | 7/2001 | Strobel et al. |
| 6,280,444 B1 | 8/2001 | Zucherman et al. |
| 6,287,313 B1 | 9/2001 | Sasso |
| 6,293,909 B1 | 9/2001 | Chu et al. |
| 6,293,952 B1 | 9/2001 | Brosens et al. |
| 6,296,647 B1 | 10/2001 | Robioneck et al. |
| 6,302,914 B1 | 10/2001 | Michelson |
| 6,306,136 B1 | 10/2001 | Baccelli |
| 6,319,254 B1 | 11/2001 | Giet et al. |
| 6,319,272 B1 | 11/2001 | Brenneman et al. |
| 6,332,882 B1 | 12/2001 | Zucherman et al. |
| 6,332,883 B1 | 12/2001 | Zucherman et al. |
| 6,332,895 B1 | 12/2001 | Suddaby |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,897 B1 | 4/2002 | Bonutti |
| 6,368,350 B1 | 4/2002 | Erickson et al. |
| 6,368,351 B1 | 4/2002 | Glenn |
| 6,371,971 B1 | 4/2002 | Tsugita et al. |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,379,363 B1 | 4/2002 | Herrington et al. |
| 6,387,130 B1 | 5/2002 | Stone |
| 6,409,766 B1 | 6/2002 | Brett |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,425,919 B1 | 7/2002 | Lambrecht |
| 6,428,541 B1 | 8/2002 | Boyd et al. |
| 6,428,556 B1 | 8/2002 | Chin |
| 6,436,140 B1 | 8/2002 | Liu et al. |
| 6,436,143 B1 | 8/2002 | Ross et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,468,277 B1 | 10/2002 | Justin et al. |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,488,710 B2 | 12/2002 | Besselink |
| 6,489,309 B1 | 12/2002 | Singh et al. |
| 6,491,714 B1 | 12/2002 | Bennett |
| 6,494,860 B2 | 12/2002 | Rocamora et al. |
| 6,494,893 B2 | 12/2002 | Dubrul et al. |
| 6,500,178 B2 | 12/2002 | Zucherman et al. |
| 6,506,192 B1 | 1/2003 | Gertzman et al. |
| 6,511,481 B2 | 1/2003 | von Hoffmann et al. |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,527,774 B2 | 3/2003 | Lieberman |

(56) References Cited

U.S. PATENT DOCUMENTS

| | | |
|---|---|---|
| 6,527,803 B1 | 3/2003 | Crozet |
| 6,527,804 B1 | 3/2003 | Gauchet et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,554,831 B1 | 4/2003 | Rivard et al. |
| 6,554,852 B1 | 4/2003 | Oberlander |
| 6,558,389 B2 | 5/2003 | Clark et al. |
| 6,558,424 B2 | 5/2003 | Thalgott |
| 6,562,046 B2 | 5/2003 | Sasso |
| 6,562,049 B1 | 5/2003 | Norlander et al. |
| 6,562,074 B2 | 5/2003 | Gerbec et al. |
| 6,575,979 B1 | 6/2003 | Cragg |
| 6,576,016 B1 | 6/2003 | Hochshuler et al. |
| 6,579,293 B1 | 6/2003 | Chandran |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,595,998 B2 | 7/2003 | Johnson et al. |
| 6,596,008 B1 | 7/2003 | Kambin |
| 6,599,297 B1 | 7/2003 | Carlsson et al. |
| 6,607,530 B1 | 8/2003 | Carl et al. |
| 6,610,091 B1 | 8/2003 | Reiley |
| 6,610,094 B2 | 8/2003 | Husson |
| 6,613,050 B1 | 9/2003 | Wagner et al. |
| 6,616,678 B2 | 9/2003 | Nishtala et al. |
| 6,620,196 B1 | 9/2003 | Trieu |
| 6,626,944 B1 | 9/2003 | Taylor |
| 6,632,224 B2 | 10/2003 | Cachia et al. |
| 6,635,059 B2 | 10/2003 | Randall et al. |
| 6,635,362 B2 | 10/2003 | Zheng |
| 6,641,564 B1 | 11/2003 | Kraus |
| 6,641,614 B1 | 11/2003 | Wagner et al. |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,655,962 B1 | 12/2003 | Kennard |
| 6,666,891 B2 | 12/2003 | Boehm, Jr. et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,664 B1 | 1/2004 | Al-Assir |
| 6,676,665 B2 | 1/2004 | Foley et al. |
| 6,679,833 B2 | 1/2004 | Smith et al. |
| 6,682,535 B2 | 1/2004 | Hoogland |
| 6,685,706 B2 | 2/2004 | Padget et al. |
| 6,685,742 B1 | 2/2004 | Jackson |
| 6,689,152 B2 | 2/2004 | Balceta et al. |
| 6,692,499 B2 | 2/2004 | Tormala et al. |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,760 B2 | 4/2004 | Dorchak et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,730,126 B2 | 5/2004 | Boehm, Jr. et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| 6,743,166 B2 | 6/2004 | Berci et al. |
| 6,743,255 B2 | 6/2004 | Ferree |
| 6,746,451 B2 | 6/2004 | Middleton et al. |
| 6,752,831 B2 | 6/2004 | Sybert et al. |
| 6,761,720 B1 | 7/2004 | Senegas |
| 6,770,075 B2 | 8/2004 | Howland |
| 6,790,210 B1 | 9/2004 | Cragg et al. |
| 6,793,656 B1 | 9/2004 | Mathews |
| 6,793,678 B2 | 9/2004 | Hawkins |
| 6,796,983 B1 | 9/2004 | Zucherman et al. |
| 6,805,685 B2 | 10/2004 | Taylor |
| 6,805,695 B2 | 10/2004 | Keith et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,821,298 B1 | 11/2004 | Jackson |
| 6,824,565 B2 | 11/2004 | Muhanna |
| 6,830,589 B2 | 12/2004 | Erickson |
| 6,835,205 B2 | 12/2004 | Atkinson et al. |
| 6,835,206 B2 | 12/2004 | Jackson |
| 6,852,129 B2 | 2/2005 | Gerbec et al. |
| 6,855,167 B2 | 2/2005 | Shimp |
| 6,863,673 B2 | 3/2005 | Gerbec et al. |
| 6,875,215 B2 | 4/2005 | Taras et al. |
| 6,881,229 B2 | 4/2005 | Khandkar et al. |
| 6,887,243 B2 | 5/2005 | Culbert |
| 6,890,333 B2 | 5/2005 | von Hoffmann et al. |
| 6,893,464 B2 | 5/2005 | Kiester |
| 6,893,466 B2 | 5/2005 | Trieu |
| 6,902,566 B2 | 6/2005 | Zucherman et al. |
| 6,908,465 B2 | 6/2005 | von Hoffmann et al. |
| 6,916,323 B2 | 7/2005 | Kitchens |
| 6,921,403 B2 | 7/2005 | Cragg et al. |
| 6,923,811 B1 | 8/2005 | Carl et al. |
| 6,929,606 B2 | 8/2005 | Ritland |
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,975 B2 | 9/2005 | Dalton |
| 6,946,000 B2 | 9/2005 | Senegas et al. |
| 6,949,100 B1 | 9/2005 | Venturini |
| 6,951,561 B2 | 10/2005 | Warren et al. |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 6,972,035 B2 | 12/2005 | Michelson |
| 6,997,929 B2 | 2/2006 | Manzi et al. |
| 7,004,945 B2 | 2/2006 | Boyd et al. |
| 7,008,431 B2 | 3/2006 | Simonson |
| 7,018,412 B2 | 3/2006 | Ferreira et al. |
| 7,018,415 B1 | 3/2006 | McKay |
| 7,018,416 B2 | 3/2006 | Hanson et al. |
| 7,025,746 B2 | 4/2006 | Tal |
| 7,029,473 B2 | 4/2006 | Zucherman et al. |
| 7,037,339 B2 | 5/2006 | Houfburg et al. |
| 7,041,107 B2 | 5/2006 | Pohjonen et al. |
| 7,048,736 B2 | 5/2006 | Robinson et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,066,960 B1 | 6/2006 | Dickman |
| 7,066,961 B2 | 6/2006 | Michelson |
| 7,070,601 B2 | 7/2006 | Culbert et al. |
| 7,074,203 B1 | 7/2006 | Johanson et al. |
| 7,083,650 B2 | 8/2006 | Moskowitz et al. |
| 7,087,083 B2 | 8/2006 | Pasquet et al. |
| 7,094,239 B1 | 8/2006 | Michelson |
| 7,094,257 B2 | 8/2006 | Mujwid et al. |

(56) References Cited

U.S. PATENT DOCUMENTS

| | | |
|---|---|---|
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,118,572 B2 | 10/2006 | Bramlet et al. |
| 7,118,579 B2 | 10/2006 | Michelson |
| 7,118,598 B2 | 10/2006 | Michelson |
| 7,128,760 B2 | 10/2006 | Michelson |
| 7,153,305 B2 | 12/2006 | Johnson et al. |
| D536,096 S | 1/2007 | Hoogland et al. |
| 7,156,876 B2 | 1/2007 | Moumene et al. |
| 7,163,558 B2 | 1/2007 | Senegas et al. |
| 7,172,612 B2 | 2/2007 | Ishikawa |
| 7,179,294 B2 | 2/2007 | Eisermann et al. |
| 7,201,751 B2 | 4/2007 | Zucherman et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,238,204 B2 | 7/2007 | Le Couedic et al. |
| 7,267,683 B2 | 9/2007 | Sharkey et al. |
| 7,282,061 B2 | 10/2007 | Sharkey et al. |
| 7,300,440 B2 | 11/2007 | Zdeblick |
| 7,306,628 B2 | 12/2007 | Zucherman et al. |
| 7,309,357 B2 | 12/2007 | Kim |
| 7,326,211 B2 | 2/2008 | Padget et al. |
| 7,326,248 B2 | 2/2008 | Michelson |
| 7,335,203 B2 | 2/2008 | Winslow et al. |
| 7,361,140 B2 | 4/2008 | Ries et al. |
| 7,371,238 B2 | 5/2008 | Soboleski et al. |
| 7,377,942 B2 | 5/2008 | Berry |
| 7,400,930 B2 | 7/2008 | Sharkey et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,445,636 B2 | 11/2008 | Michelson |
| 7,445,637 B2 | 11/2008 | Taylor |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,488,326 B2 | 2/2009 | Elliott |
| 7,503,933 B2 | 3/2009 | Michelson |
| 7,507,241 B2 | 3/2009 | Levy et al. |
| 7,517,363 B2 | 3/2009 | Rogers |
| 7,520,888 B2 | 4/2009 | Trieu |
| 7,547,317 B2 | 6/2009 | Cragg |
| 7,556,629 B2 | 7/2009 | von Hoffmann et al. |
| 7,556,651 B2 | 7/2009 | Humphreys et al. |
| 7,569,054 B2 | 8/2009 | Michelson |
| 7,569,074 B2 | 8/2009 | Eiserman et al. |
| 7,588,574 B2 | 9/2009 | Assell et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,378 B2 | 12/2009 | Foley |
| 7,641,657 B2 | 1/2010 | Cragg |
| 7,641,670 B2 | 1/2010 | Davison et al. |
| 7,647,123 B2 | 1/2010 | Sharkey et al. |
| 7,648,523 B2 | 1/2010 | Mirkovic et al. |
| 7,670,354 B2 | 3/2010 | Davison et al. |
| 7,674,273 B2 | 3/2010 | Davison et al. |
| 7,682,370 B2 | 3/2010 | Pagliuca et al. |
| 7,691,120 B2 | 4/2010 | Shluzas et al. |
| 7,691,147 B2 | 4/2010 | Gutlin et al. |
| 7,699,878 B2 | 4/2010 | Pavlov et al. |
| 7,703,727 B2 | 4/2010 | Selness |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,740,633 B2 | 6/2010 | Assell et al. |
| 7,744,599 B2 | 6/2010 | Cragg |
| 7,749,270 B2 | 7/2010 | Peterman |
| 7,762,995 B2 | 7/2010 | Eversull et al. |
| 7,763,025 B2 | 7/2010 | Assell et al. |
| 7,763,055 B2 | 7/2010 | Foley |
| 7,766,930 B2 | 8/2010 | DiPoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,083 B2 | 9/2010 | Smith et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,922,729 B2 | 4/2011 | Michelson |
| 7,931,689 B2 | 4/2011 | Hochschuler et al. |
| 7,938,832 B2 | 5/2011 | Culbert et al. |
| 7,951,199 B2 | 5/2011 | Miller |
| 7,985,231 B2 | 7/2011 | Sankaran |
| 7,993,403 B2 | 8/2011 | Foley et al. |
| 7,998,176 B2 | 8/2011 | Culbert |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,109,977 B2 | 2/2012 | Culbert et al. |
| 8,114,088 B2 | 2/2012 | Miller |
| 8,133,232 B2 | 3/2012 | Levy et al. |
| 8,177,812 B2 | 5/2012 | Sankaran |
| 8,192,495 B2 | 6/2012 | Simpson et al. |
| 8,221,501 B2 | 7/2012 | Eiserman et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,273,128 B2 | 9/2012 | Oh et al. |
| 8,273,129 B2 | 9/2012 | Baynham et al. |
| 8,287,599 B2 | 10/2012 | McGuckin |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |

(56) References Cited

U.S. PATENT DOCUMENTS

| | | |
|---|---|---|
| 8,366,777 B2 | 2/2013 | Matthis et al. |
| 8,382,842 B2 | 2/2013 | Greenhalgh et al. |
| 8,394,129 B2 | 3/2013 | Morgenstern Lopez et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,659 B2 | 7/2013 | Weiman |
| 8,506,635 B2 | 8/2013 | Palmatier et al. |
| 8,518,087 B2 | 8/2013 | Morgenstern et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,597,333 B2 | 12/2013 | Morgenstern Lopez et al. |
| 8,603,170 B2 | 12/2013 | Cipoletti et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,242 B2 | 10/2014 | Morgenstern Lopez et al. |
| 8,852,243 B2 | 10/2014 | Morgenstern Lopez et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,926,704 B2 | 1/2015 | Glerum |
| 8,936,641 B2 | 1/2015 | Cain |
| 8,940,052 B2 | 1/2015 | Lechmann et al. |
| 8,979,860 B2 | 3/2015 | Voellmicke et al. |
| 8,986,387 B1 | 3/2015 | To et al. |
| 9,005,291 B2 | 4/2015 | Loebl et al. |
| 9,039,767 B2 | 5/2015 | Raymond et al. |
| 9,039,771 B2 | 5/2015 | Glerum et al. |
| 9,060,876 B1 | 6/2015 | To et al. |
| 9,078,767 B1 | 7/2015 | McLean |
| 9,091,488 B2 | 7/2015 | Postma et al. |
| 9,095,446 B2 | 8/2015 | Landry et al. |
| 9,095,447 B2 | 8/2015 | Barreiro et al. |
| 9,101,489 B2 | 8/2015 | Protopsaltis et al. |
| 9,107,766 B1 | 8/2015 | Mclean et al. |
| 9,277,928 B2 | 3/2016 | Morgenstern Lopez |
| 9,402,739 B2 | 8/2016 | Weiman et al. |
| 9,463,099 B2 | 10/2016 | Levy et al. |
| 2001/0012950 A1 | 8/2001 | Nishtala et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2001/0049529 A1 | 12/2001 | Cachia et al. |
| 2001/0049530 A1 | 12/2001 | Culbert et al. |
| 2002/0001476 A1 | 1/2002 | Nagamine et al. |
| 2002/0010070 A1 | 1/2002 | Cales et al. |
| 2002/0032462 A1 | 3/2002 | Houser et al. |
| 2002/0055740 A1 | 5/2002 | Lieberman |
| 2002/0068976 A1 | 6/2002 | Jackson |
| 2002/0068977 A1 | 6/2002 | Jackson |
| 2002/0087152 A1 | 7/2002 | Mikus et al. |
| 2002/0091387 A1 | 7/2002 | Hoogland |
| 2002/0120335 A1 | 8/2002 | Angelucci et al. |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | von Hoffmann et al. |
| 2002/0151895 A1 | 10/2002 | Soboleski et al. |
| 2002/0151976 A1 | 10/2002 | Foley et al. |
| 2002/0161444 A1 | 10/2002 | Choi |
| 2002/0165612 A1 | 11/2002 | Gerber et al. |
| 2002/0183848 A1 | 12/2002 | Ray et al. |
| 2003/0004575 A1 | 1/2003 | Erickson |
| 2003/0004576 A1 | 1/2003 | Thalgott |
| 2003/0023305 A1 | 1/2003 | McKay |
| 2003/0028250 A1 | 2/2003 | Reiley et al. |
| 2003/0040799 A1 | 2/2003 | Boyd et al. |
| 2003/0063582 A1 | 4/2003 | Culbert |
| 2003/0065330 A1 | 4/2003 | Zucherman et al. |
| 2003/0065396 A1 | 4/2003 | Michelson |
| 2003/0069582 A1 | 4/2003 | Culbert et al. |
| 2003/0078667 A1 | 4/2003 | Manasas et al. |
| 2003/0083688 A1 | 5/2003 | Simonson |
| 2003/0130739 A1 | 7/2003 | Gerbec et al. |
| 2003/0135275 A1 | 7/2003 | Garcia |
| 2003/0139648 A1 | 7/2003 | Foley et al. |
| 2003/0139812 A1 | 7/2003 | Garcia |
| 2003/0139813 A1 | 7/2003 | Messerli et al. |
| 2003/0153874 A1 | 8/2003 | Tal |
| 2003/0187431 A1 | 10/2003 | Simonson |
| 2003/0204261 A1 | 10/2003 | Eiserman |
| 2003/0208122 A1 | 11/2003 | Melkent et al. |
| 2003/0208220 A1 | 11/2003 | Worley et al. |
| 2003/0220643 A1 | 11/2003 | Ferree |
| 2003/0229350 A1 | 12/2003 | Kay |
| 2003/0233102 A1 | 12/2003 | Nakamura et al. |
| 2003/0233145 A1 | 12/2003 | Landry et al. |
| 2004/0006391 A1 | 1/2004 | Reiley |
| 2004/0008949 A1 | 1/2004 | Liu et al. |
| 2004/0019359 A1 | 1/2004 | Worley et al. |
| 2004/0024463 A1 | 2/2004 | Thomas et al. |
| 2004/0030387 A1 | 2/2004 | Landry et al. |
| 2004/0049190 A1 | 3/2004 | Biedermann et al. |
| 2004/0049223 A1 | 3/2004 | Nishtala et al. |
| 2004/0054412 A1 | 3/2004 | Gerbec et al. |
| 2004/0059350 A1 | 3/2004 | Gordon et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0097924 A1 | 5/2004 | Lambrecht et al. |
| 2004/0097941 A1 | 5/2004 | Weiner et al. |
| 2004/0097973 A1 | 5/2004 | Loshakove et al. |
| 2004/0106925 A1 | 6/2004 | Culbert |
| 2004/0059339 A1 | 7/2004 | Roehm, III et al. |
| 2004/0127906 A1 | 7/2004 | Culbert et al. |
| 2004/0127991 A1 | 7/2004 | Ferree |
| 2004/0133280 A1 | 7/2004 | Trieu |
| 2004/0143284 A1 | 7/2004 | Chin |
| 2004/0143734 A1 | 7/2004 | Buer et al. |
| 2004/0147877 A1 | 7/2004 | Heuser |
| 2004/0147950 A1 | 7/2004 | Mueller et al. |
| 2004/0153065 A1 | 8/2004 | Lim |
| 2004/0153156 A1 | 8/2004 | Cohen et al. |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0172133 A1 | 9/2004 | Gerber et al. |
| 2004/0186471 A1 | 9/2004 | Trieu |
| 2004/0186482 A1 | 9/2004 | Kolb et al. |
| 2004/0186570 A1 | 9/2004 | Rapp |
| 2004/0186577 A1 | 9/2004 | Ferree |
| 2004/0199162 A1 | 10/2004 | von Hoffmann et al. |
| 2004/0215343 A1 | 10/2004 | Hochschuler et al. |
| 2004/0215344 A1 | 10/2004 | Hochschuler et al. |

(56) References Cited

U.S. PATENT DOCUMENTS

| | | |
|---|---|---|
| 2004/0220580 A1 | 11/2004 | Johnson et al. |
| 2004/0225292 A1 | 11/2004 | Sasso et al. |
| 2004/0225361 A1 | 11/2004 | Glenn et al. |
| 2004/0230309 A1 | 11/2004 | DiMauro |
| 2004/0243239 A1 | 12/2004 | Taylor |
| 2004/0249466 A1 | 12/2004 | Liu et al. |
| 2004/0254575 A1 | 12/2004 | Obenchain et al. |
| 2004/0260297 A1 | 12/2004 | Padget et al. |
| 2004/0266257 A1 | 12/2004 | Ries et al. |
| 2005/0019365 A1 | 1/2005 | Frauchiger et al. |
| 2005/0033289 A1 | 2/2005 | Warren et al. |
| 2005/0033434 A1 | 2/2005 | Berry |
| 2005/0038515 A1 | 2/2005 | Kunzler |
| 2005/0043796 A1 | 2/2005 | Grant et al. |
| 2005/0065610 A1 | 3/2005 | Pisharodi |
| 2005/0090443 A1 | 4/2005 | Fallin et al. |
| 2005/0090833 A1 | 4/2005 | Di Poto |
| 2005/0102202 A1 | 5/2005 | Linden et al. |
| 2005/0113916 A1 | 5/2005 | Branch |
| 2005/0113917 A1 | 5/2005 | Chae et al. |
| 2005/0113927 A1 | 5/2005 | Malek |
| 2005/0118550 A1 | 6/2005 | Turri |
| 2005/0119657 A1 | 6/2005 | Goldsmith |
| 2005/0125062 A1 | 6/2005 | Biedermann et al. |
| 2005/0130929 A1 | 6/2005 | Boyd |
| 2005/0131406 A1 | 6/2005 | Reiley et al. |
| 2005/0131409 A1 | 6/2005 | Chervitz et al. |
| 2005/0131411 A1 | 6/2005 | Culbert et al. |
| 2005/0131538 A1 | 6/2005 | Chervitz et al. |
| 2005/0137595 A1 | 6/2005 | von Hoffmann et al. |
| 2005/0143734 A1 | 6/2005 | Cachia et al. |
| 2005/0149030 A1 | 7/2005 | Serhan |
| 2005/0154467 A1 | 7/2005 | Peterman et al. |
| 2005/0165398 A1 | 7/2005 | Reiley |
| 2005/0165485 A1 | 7/2005 | Trieu |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177240 A1 | 8/2005 | Blain |
| 2005/0182414 A1 | 8/2005 | Manzi et al. |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0203512 A1 | 9/2005 | Hawkins et al. |
| 2005/0216026 A1 | 9/2005 | Culbert |
| 2005/0222681 A1 | 10/2005 | Richley et al. |
| 2005/0251142 A1 | 11/2005 | von Hoffmann et al. |
| 2005/0256525 A1 | 11/2005 | Warren et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2005/0283238 A1 | 12/2005 | Reiley |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0020284 A1 | 1/2006 | Foley et al. |
| 2006/0030872 A1 | 2/2006 | Culbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041314 A1 | 2/2006 | Millard |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki |
| 2006/0079908 A1 | 4/2006 | Lieberman |
| 2006/0084977 A1 | 4/2006 | Lieberman |
| 2006/0084988 A1 | 4/2006 | Kim |
| 2006/0085010 A1 | 4/2006 | Lieberman |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0161166 A1 | 7/2006 | Johnson et al. |
| 2006/0178743 A1 | 8/2006 | Carter |
| 2006/0195103 A1 | 8/2006 | Padget et al. |
| 2006/0206207 A1 | 9/2006 | Dryer et al. |
| 2006/0217711 A1 | 9/2006 | Stevens et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235531 A1 | 10/2006 | Buettner |
| 2006/0247634 A1 | 11/2006 | Warner et al. |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2006/0276899 A1 | 12/2006 | Zipnick et al. |
| 2006/0276901 A1 | 12/2006 | Zipnick et al. |
| 2006/0276902 A1 | 12/2006 | Boyer, II et al. |
| 2006/0293662 A1 | 12/2006 | Boyer et al. |
| 2006/0293663 A1 | 12/2006 | Walkenhorst et al. |
| 2007/0010826 A1 | 1/2007 | Rhoda |
| 2007/0010886 A1 | 1/2007 | Banick et al. |
| 2007/0016191 A1 | 1/2007 | Culbert et al. |
| 2007/0032790 A1 | 2/2007 | Aschmann et al. |
| 2007/0055236 A1 | 3/2007 | Hudgins et al. |
| 2007/0055377 A1 | 3/2007 | Hanson et al. |
| 2007/0067035 A1 | 3/2007 | Falahee |
| 2007/0073399 A1 | 3/2007 | Zipnick et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0149978 A1 | 6/2007 | Shezifi et al. |
| 2007/0162005 A1 | 7/2007 | Peterson et al. |
| 2007/0168036 A1 | 7/2007 | Ainsworth et al. |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0191959 A1 | 8/2007 | Hartmann et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0219634 A1 | 9/2007 | Greenhalgh et al. |
| 2007/0233083 A1 | 10/2007 | Abdou |
| 2007/0233089 A1 | 10/2007 | DiPoto et al. |
| 2007/0233244 A1 | 10/2007 | Lopez et al. |
| 2007/0270954 A1 | 11/2007 | Wu |
| 2007/0270968 A1 | 11/2007 | Baynham et al. |
| 2007/0276375 A1 | 11/2007 | Rapp |
| 2007/0282449 A1 | 12/2007 | de Villiers et al. |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058598 A1 | 3/2008 | Ries et al. |
| 2008/0058944 A1 | 3/2008 | Duplessis et al. |
| 2008/0065219 A1 | 3/2008 | Dye |
| 2008/0077148 A1 | 3/2008 | Ries et al. |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0108996 A1 | 5/2008 | Padget et al. |

(56) References Cited

U.S. PATENT DOCUMENTS

| | | |
|---|---|---|
| 2008/0132934 A1 | 6/2008 | Reilly |
| 2008/0140207 A1 | 6/2008 | Olmos |
| 2008/0147193 A1 | 6/2008 | Matthis et al. |
| 2008/0154377 A1 | 6/2008 | Voellmicke et al. |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0255618 A1 | 10/2008 | Fisher et al. |
| 2008/0262619 A1 | 10/2008 | Ray |
| 2008/0281425 A1 | 11/2008 | Thalgott |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2009/0005873 A1 | 1/2009 | Slivka et al. |
| 2009/0030423 A1 | 1/2009 | Puno |
| 2009/0054991 A1 | 2/2009 | Biyani |
| 2009/0069813 A1 | 3/2009 | von Hoffmann et al. |
| 2009/0076610 A1 | 3/2009 | Afzal |
| 2009/0099568 A1 | 4/2009 | Lowry et al. |
| 2009/0105712 A1 | 4/2009 | Dauster |
| 2009/0105745 A1 | 4/2009 | Culbert |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0149857 A1 | 6/2009 | Culbert et al. |
| 2009/0164020 A1 | 6/2009 | Janowski |
| 2009/0177284 A1 | 7/2009 | Rogers et al. |
| 2009/0182429 A1 | 7/2009 | Humphreys et al. |
| 2009/0198339 A1 | 8/2009 | Kleiner |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0275890 A1 | 11/2009 | Leibowitz et al. |
| 2009/0292361 A1 | 11/2009 | Lopez |
| 2010/0016905 A1 | 1/2010 | Greenhalgh et al. |
| 2010/0040332 A1 | 2/2010 | Van Den Meersschaut et al. |
| 2010/0076492 A1 | 3/2010 | Warner et al. |
| 2010/0076559 A1 | 3/2010 | Bagga |
| 2010/0082109 A1 | 4/2010 | Greenhalgh et al. |
| 2010/0114105 A1 | 5/2010 | Butters |
| 2010/0114147 A1 | 5/2010 | Biyani |
| 2010/0174314 A1 | 7/2010 | Mirkovic et al. |
| 2010/0179594 A1 | 7/2010 | Theofilos et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234956 A1 | 9/2010 | Attia et al. |
| 2010/0262240 A1 | 10/2010 | Chavatte et al. |
| 2010/0268231 A1 | 10/2010 | Kuslich et al. |
| 2010/0286783 A1 | 11/2010 | Lechmann et al. |
| 2010/0292700 A1 | 11/2010 | Ries |
| 2010/0298938 A1 | 11/2010 | Humphreys et al. |
| 2010/0324607 A1 | 12/2010 | Davis |
| 2010/0331891 A1 | 12/2010 | Culbert et al. |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0054538 A1 | 3/2011 | Zehavi et al. |
| 2011/0071527 A1 | 3/2011 | Nelson et al. |
| 2011/0093074 A1 | 4/2011 | Glerum et al. |
| 2011/0098531 A1 | 4/2011 | To |
| 2011/0098628 A1 | 4/2011 | Yeung et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0153020 A1 | 6/2011 | Abdelgany et al. |
| 2011/0172716 A1 | 7/2011 | Glerum |
| 2011/0172774 A1 | 7/2011 | Varela |
| 2011/0238072 A1 | 9/2011 | Tyndall |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0215262 A1 | 8/2012 | Culbert et al. |
| 2012/0226357 A1 | 9/2012 | Varela |
| 2012/0232658 A1 | 9/2012 | Morgenstern Lopez et al. |
| 2012/0277795 A1 | 11/2012 | von Hoffmann et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0025169 A1 | 1/2014 | Lechmann et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0094916 A1* | 4/2014 | Glerum .................. A61F 2/442 623/17.15 |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |

(56) References Cited

U.S. PATENT DOCUMENTS

| | | | |
|---|---|---|---|
| 2014/0180421 A1 | 6/2014 | Glerum et al. | |
| 2014/0228959 A1 | 8/2014 | Niemiec et al. | |
| 2014/0243981 A1 | 8/2014 | Davenport et al. | |
| 2014/0243982 A1 | 8/2014 | Miller | |
| 2014/0249629 A1 | 9/2014 | Moskowitz et al. | |
| 2014/0249630 A1 | 9/2014 | Weiman | |
| 2014/0257484 A1 | 9/2014 | Flower et al. | |
| 2014/0257486 A1 | 9/2014 | Alheidt | |
| 2014/0277139 A1* | 9/2014 | Vrionis | A61B 17/70 606/246 |
| 2014/0277204 A1 | 9/2014 | Sandhu | |
| 2014/0277474 A1 | 9/2014 | Robinson et al. | |
| 2014/0303731 A1 | 10/2014 | Glerum et al. | |
| 2014/0303732 A1 | 10/2014 | Rhoda et al. | |
| 2014/0324171 A1 | 10/2014 | Glerum et al. | |
| 2015/0012097 A1 | 1/2015 | Ibarra et al. | |
| 2015/0045894 A1 | 2/2015 | Hawkins et al. | |
| 2015/0094610 A1 | 4/2015 | Morgenstern Lopez et al. | |
| 2015/0094812 A1 | 4/2015 | Marden et al. | |
| 2015/0094813 A1 | 4/2015 | Lechmann et al. | |
| 2015/0112398 A1 | 4/2015 | Morgenstern Lopez et al. | |
| 2015/0112438 A1 | 4/2015 | McLean | |
| 2015/0157470 A1 | 6/2015 | Voellmicke et al. | |
| 2015/0182347 A1 | 7/2015 | Robinson | |
| 2015/0250606 A1 | 9/2015 | Mclean | |
| 2016/0045333 A1 | 2/2016 | Baynham | |
| 2016/0081814 A1 | 3/2016 | Baynham | |
| 2016/0317317 A1 | 3/2016 | Marchek et al. | |
| 2016/0242929 A1 | 8/2016 | Voellmicke et al. | |
| 2016/0256291 A1 | 9/2016 | Miller | |
| 2016/0367265 A1 | 12/2016 | Morgenstern Lopez | |

FOREIGN PATENT DOCUMENTS

| | | |
|---|---|---|
| CN | 101909548 A | 12/2010 |
| DE | 2804936 | 8/1979 |
| DE | 3023353 | 4/1981 |
| DE | 3911610 | 10/1990 |
| DE | 4012622 | 7/1997 |
| DE | 19832798 | 11/1999 |
| DE | 20101793 | 5/2001 |
| DE | 202008001079 | 3/2008 |
| EP | 077159 | 4/1983 |
| EP | 0260044 | 3/1988 |
| EP | 282161 | 9/1988 |
| EP | 0433717 | 6/1991 |
| EP | 0525352 | 2/1993 |
| EP | 0611557 | 8/1994 |
| EP | 0625336 | 11/1994 |
| EP | 678489 | 10/1995 |
| EP | 0270704 | 6/1998 |
| EP | 1046376 | 4/2000 |
| EP | 0853929 | 9/2002 |
| EP | 1290985 | 3/2003 |
| EP | 1378205 | 7/2003 |
| EP | 1374784 | 1/2004 |
| EP | 1532949 | 5/2005 |
| EP | 1541096 | 6/2005 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 1845874 | 10/2012 |
| EP | 2764851 | 8/2014 |
| FR | 2649311 | 1/1991 |
| FR | 2699065 | 12/1992 |
| FR | 2728778 | 12/1994 |
| FR | 2718635 | 10/1995 |
| FR | 2745709 | 3/1996 |
| FR | 2730159 | 8/1996 |
| FR | 2800601 | 11/1999 |
| FR | 2801189 | 11/1999 |
| FR | 2808182 | 4/2000 |
| FR | 2874814 | 3/2006 |
| GB | 2157788 | 10/1985 |
| GB | 2173565 | 10/1986 |
| JP | 06-500039 | 6/1994 |
| JP | 06-319742 | 11/1994 |
| JP | 07-502419 | 3/1995 |
| JP | 07-184922 | 7/1995 |
| JP | 10-85232 | 4/1998 |
| JP | 11-89854 | 4/1999 |
| JP | 2003-010197 | 1/2003 |
| JP | 2003-126266 | 5/2003 |
| JP | 2003-526457 | 9/2003 |
| JP | 2006-516456 | 7/2006 |
| JP | 2007-54666 | 3/2007 |
| JP | 2011-509766 A | 3/2011 |
| JP | 2011-520580 | 7/2011 |
| JP | 4988203 | 7/2011 |
| JP | 5164571 | 8/2012 |
| JP | 64-52439 | 12/2012 |
| WO | WO 91/09572 | 12/1989 |
| WO | WO 93/04652 | 3/1993 |
| WO | WO 1994004100 | 3/1994 |
| WO | WO 1995/031158 | 11/1995 |
| WO | WO 96/28100 | 9/1996 |
| WO | WO 97/00054 | 1/1997 |
| WO | WO 99/52478 | 10/1999 |
| WO | WO 1999053871 | 10/1999 |
| WO | WO 99/62417 | 12/1999 |
| WO | WO 2000/012033 | 3/2000 |
| WO | WO 00/67652 | 5/2000 |
| WO | WO 00/76409 | 12/2000 |
| WO | WO 2000/074605 | 12/2000 |
| WO | WO 01/01895 | 1/2001 |
| WO | WO 2000/53127 | 1/2001 |
| WO | WO 2001001893 | 1/2001 |
| WO | WO 01/12054 | 2/2001 |
| WO | WO 2001017464 | 3/2001 |
| WO | WO 01/80751 | 11/2001 |
| WO | WO 02/43601 | 6/2002 |
| WO | WO 03/21308 | 3/2003 |
| WO | WO 03/43488 | 5/2003 |
| WO | WO 2004/008949 | 1/2004 |
| WO | WO 2004/064603 | 8/2004 |
| WO | WO 2004/078220 | 9/2004 |
| WO | WO 2004/078221 | 9/2004 |
| WO | WO 2004/098453 | 11/2004 |
| WO | WO 2005/112834 | 12/2005 |
| WO | WO 2005/112835 | 12/2005 |
| WO | WO 2006/017507 | 2/2006 |
| WO | WO 2006/047587 | 5/2006 |
| WO | WO 2006/058281 | 6/2006 |
| WO | WO 2006/063083 | 6/2006 |
| WO | WO 2006/065419 | 6/2006 |
| WO | WO 2006/081843 | 8/2006 |
| WO | WO 2006/108067 | 10/2006 |
| WO | WO 2007/028098 | 3/2007 |
| WO | WO 2007/048012 | 4/2007 |
| WO | WO 2007/119212 | 10/2007 |
| WO | WO 2007/124130 | 4/2008 |
| WO | WO 2008/044057 | 4/2008 |
| WO | WO 2008/064842 | 6/2008 |
| WO | WO 2008/070863 | 6/2008 |
| WO | WO 2007/009107 | 8/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2009/147527 | 12/2009 |
| WO | WO 2009/152919 | 12/2009 |
| WO | WO 2010/068725 | 6/2010 |
| WO | WO 2010/136170 | 12/2010 |
| WO | WO 2010/148112 | 12/2010 |
| WO | WO 2011/079910 | 7/2011 |
| WO | WO 2011/142761 | 11/2011 |
| WO | WO 2011/150350 | 12/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |

(56) References Cited

FOREIGN PATENT DOCUMENTS

| WO | WO 2013/023096 | 2/2013 |
|---|---|---|
| WO | WO 2013/025876 | 2/2013 |
| WO | WO 2013/043850 | 5/2013 |
| WO | WO 2013/062903 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |
| WO | WO 2014/144696 | 9/2014 |
| WO | WO 2016/069796 | 5/2016 |
| WO | WO 2016/127139 | 8/2016 |

OTHER PUBLICATIONS

Brooks, M.D. et al., "Efficacy of Supplemental Posterior Transfacet Pedicle Device Fixation in the Setting of One- or Two-Level Anterior Lumbar Interbody Fusion", retrieved Jun. 19, 2017, 6 pages.
Brochure for PERPOS PLS System Surgical Technique by Interventional Spine, 2008, 8 pages.
Paul D. Fuchs, "The use of an interspinous implant in conjunction with a graded facetectomy procedure", Spine vol. 30, No. 11, pp. 1266-1272, 2005.
Iprenburg et al., "Transforaminal Endoscopic Surgery in Lumbar Disc Herniation in an Economic Crisis—The TESSYS Method", US Musculoskeletal, 2008, pp. 47-49.
King, M.D., Don, "Internal Fixation for Lumbosacral Fusion", The Journal of Bone and Joint Surgery, J. Bone Joint Surg Am., 1948; 30: 560-578.
Morgenstern R; "Transforaminal Endoscopic Stenosis Surgery—A Comparative Study of Laser and Reamed Foraminoplasty", in European Musculoskeletal Review, Issue 1, 2009.
ProMap TM EMG Navigation Probe. Technical Brochure Spineology Inc., Dated May 2009.
Chin, Kingsley R., M.D. "Early Results of the Triage Medical Percutaneous Transfacet Pedicular BONE-LOK Compression Device for Lumbar Fusion", accessed online Jul. 10, 2017, 10 pages.
Niosi, Christina A., "Biomechanical Characterization of the three-dimentinoal kinematic behavior of the Dynesys dynamic stabilization system: an in vitro study", Eur Spine J. (2006) 15: pp. 913-922.
Manal Siddiqui, "The Positional Magnetic Resonance Imaging Changes in the Lumbar Spine Following Insertion of a Novel Interspinous Process Distraction Device", Spine vol. 30, No. 23, pp. 2677-2682, 2005.
Vikram Talwar, " Insertion loads of the X STOP Interspinous Process Distraction System Designed to Treat Neurogenic Intermittent Claudication", Eur Spine J. (2006) 15: pp. 908-912.
James F. Zucherman, "A Multicenter, Prospective, Randomized Trial Evaluating the X STOP Interspinous Process Decompression System for the Treatment of Neurogenic Intermittent Claudication", Spine, vol. 30, No. 12, pp. 1351-1358, 2005.
Kambin et al., "Percutaneous Lateral Discectomy of the Lumbar Spine: A Preliminary Report"; Clin. Orthop.; 1983; 174: 127-132.
Medco Forum, "Percutaneous Lumbar Fixation Via PERPOS PLS System Interventional Spine", Sep. 2008, vol. 15, No. 37.
Medco Forum, "Percutaneous Lumbar Fixation via PERPOS System From Interventional Spine", Oct. 2007, vol. 14, No. 49.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
U.S. Appl. No. 61/675,975, filed Jul. 26, 2012, Lechmann et al.
U.S. Appl. No. 14/685,358, filed Apr. 13, 2015, Marden et al.
U.S. Appl. No. 14/640,220, filed Mar. 6, 2015, Marden.
U.S. Appl. No. 14/685,402, filed Apr. 13, 2015, Cain.
International Patent Application No. PCT/US2013/029014, International Search Report dated Jul. 1, 2013, 7 pages.
Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expandable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).

\* cited by examiner

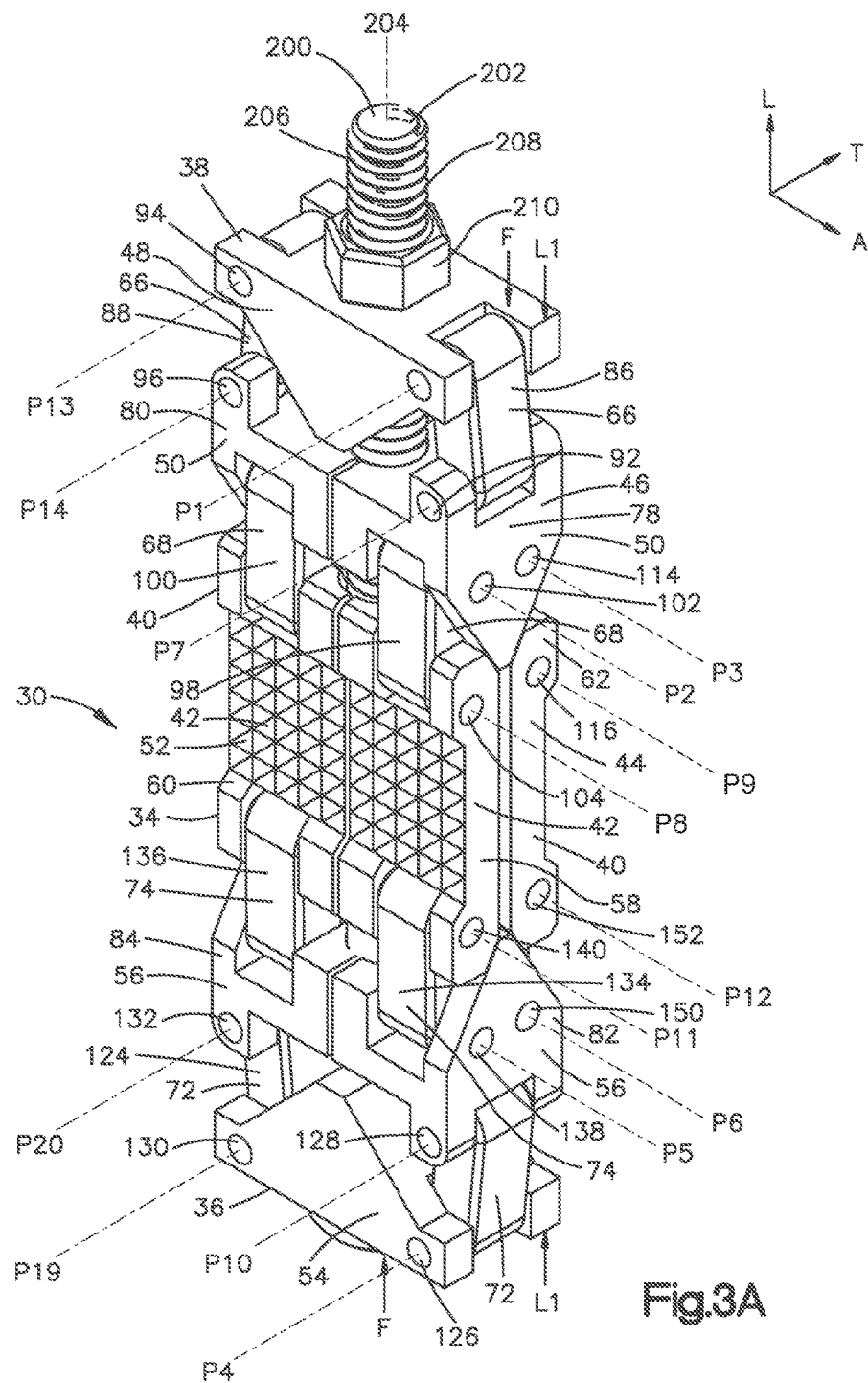

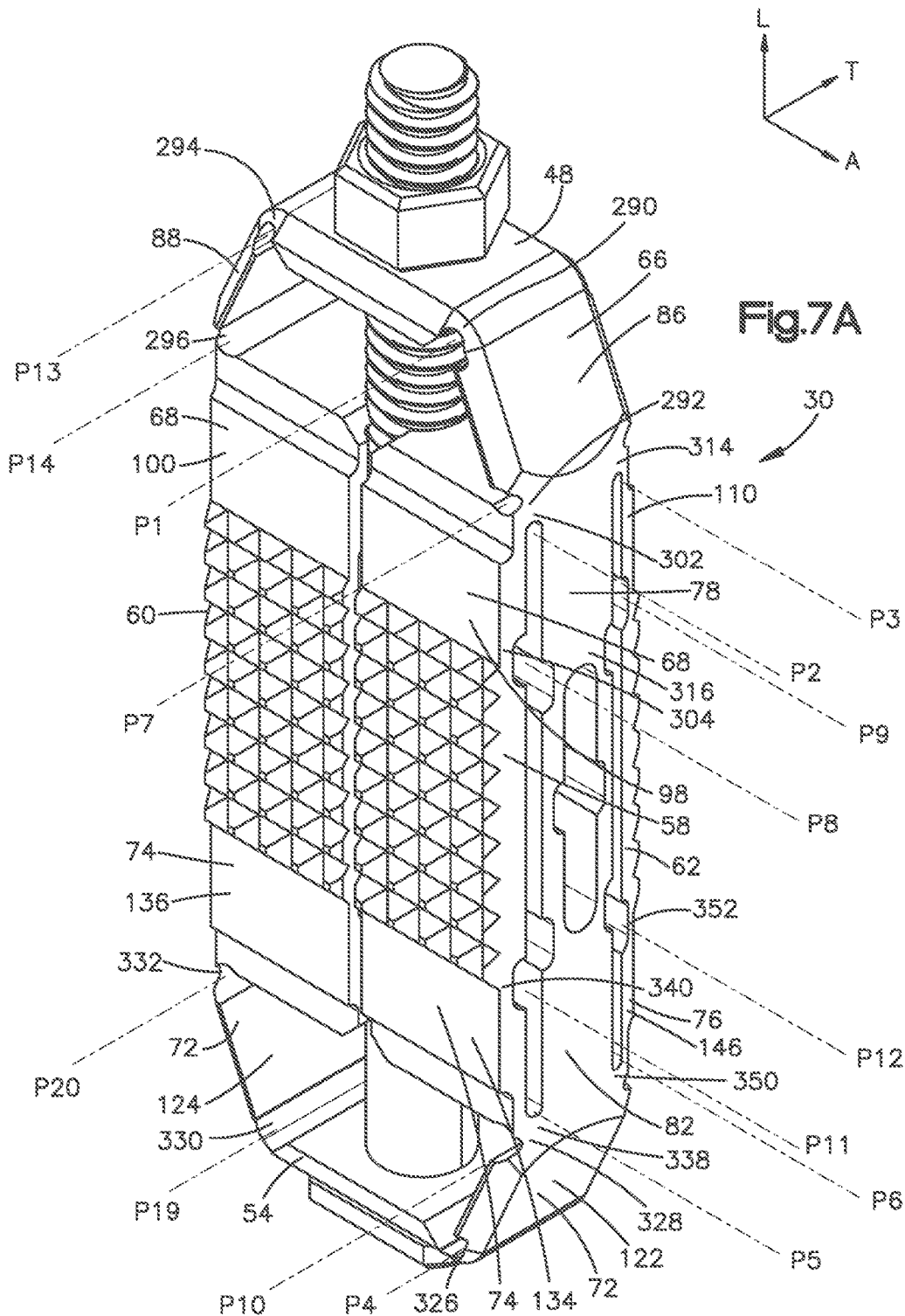

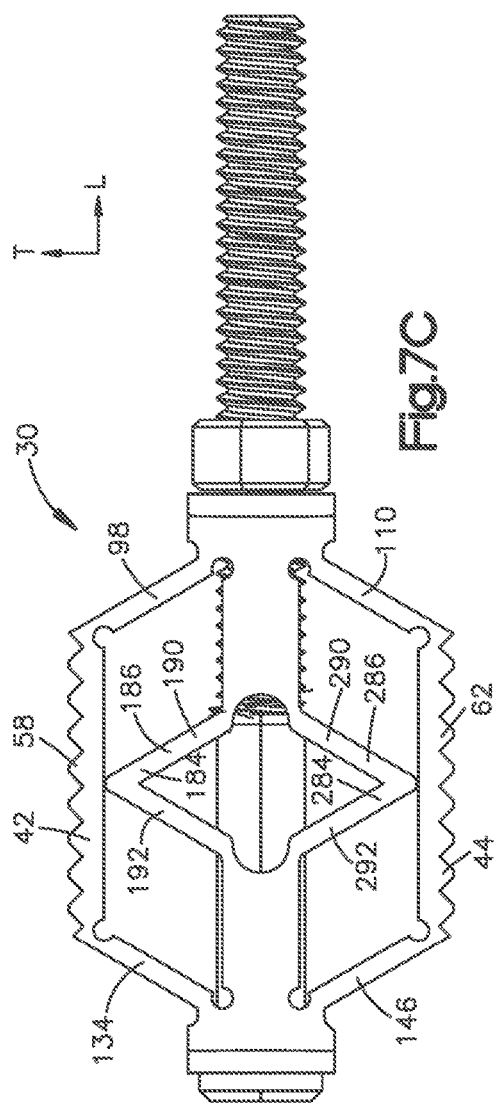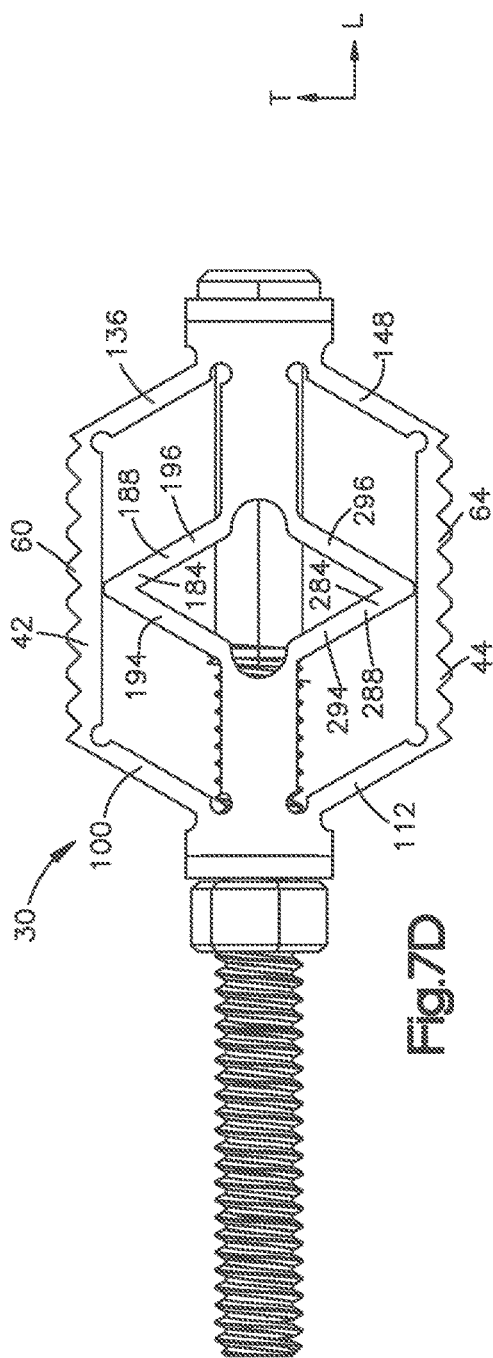

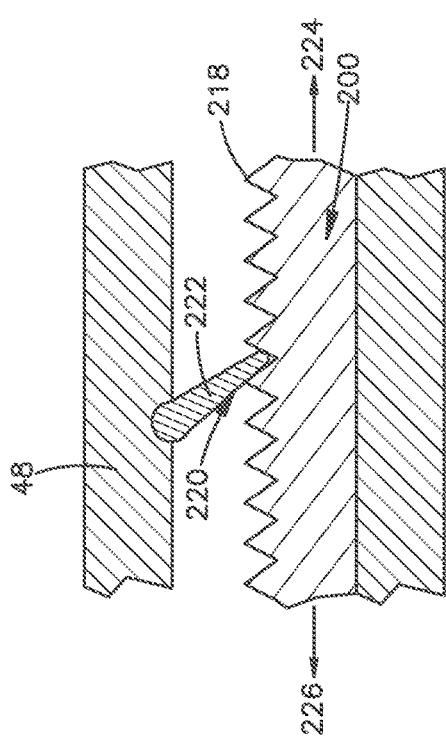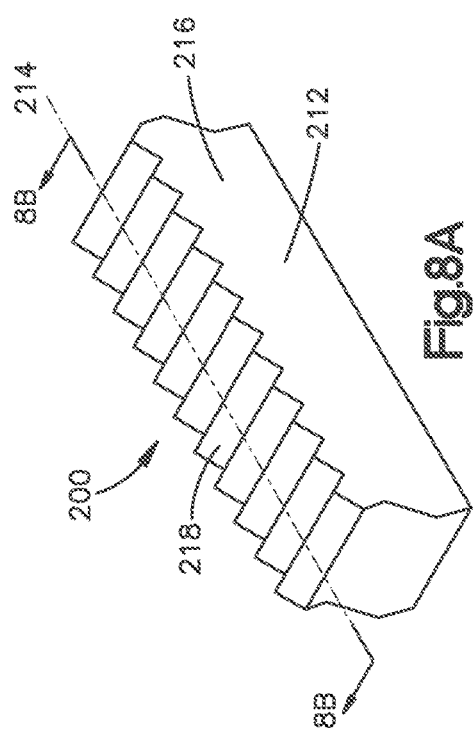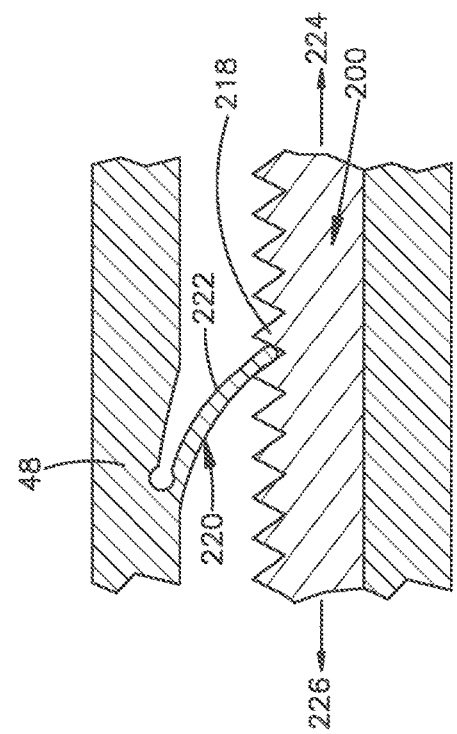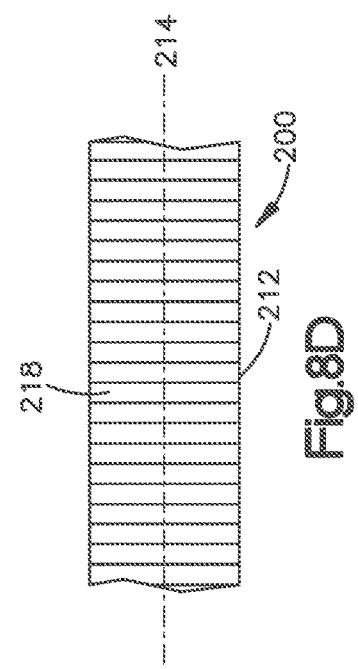

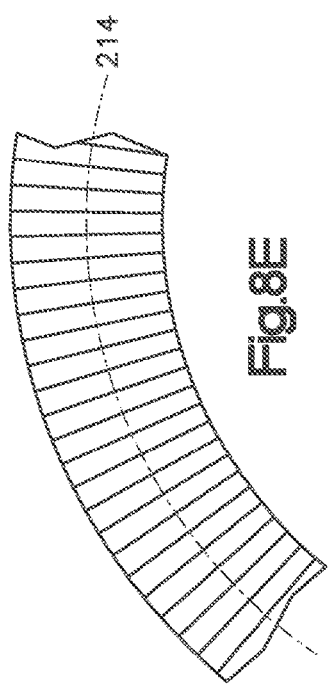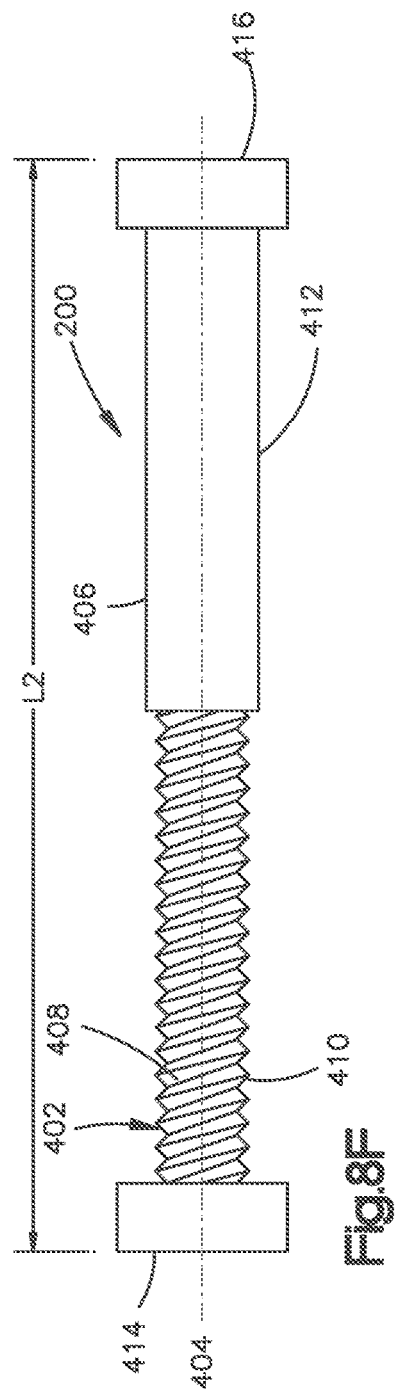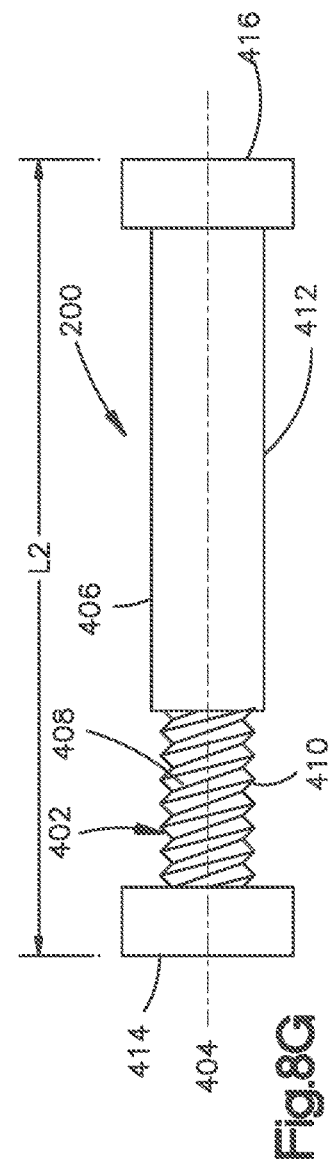

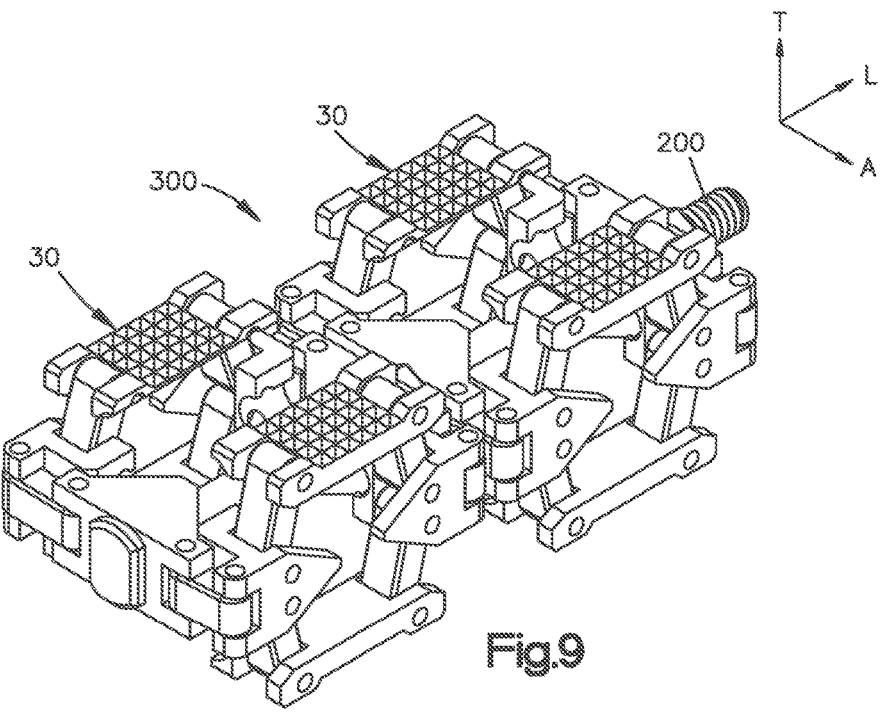
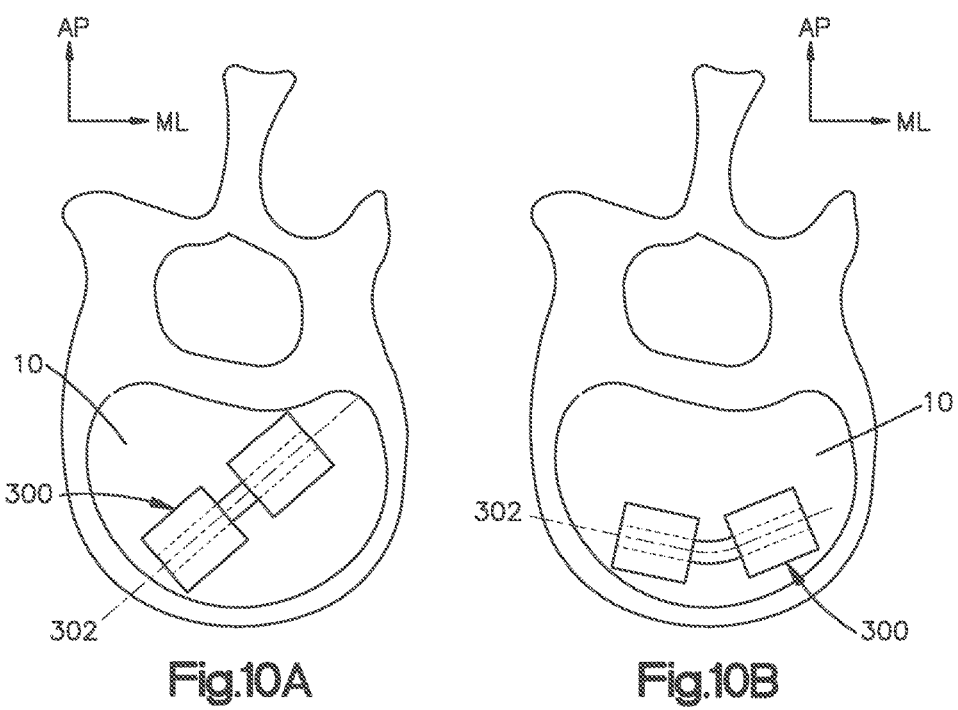

EXPANDABLE IMPLANT

TECHNICAL FIELD

The present application relates generally to medical devices. More specifically, the present application related to devices, kits, and methods for treatment of a spine.

BACKGROUND

The human spine is a flexible weight bearing column formed from a plurality of bones called vertebrae. Typically, a human spine includes thirty-three vertebrae, grouped into five regions (cervical, thoracic, lumbar, sacral, and coccygeal). Moving down the spine along the cranial-caudal direction, there are typically seven cervical vertebrae, twelve thoracic vertebrae, five lumbar vertebrae, five sacral vertebrae, and four coccygeal vertebrae.

The human vertebrae and associated connective elements are susceptible to a variety of diseases and conditions which may cause pain and disability. These diseases and conditions include spondylosis, spondylolisthesis, vertebral instability, spinal stenosis, degenerated intervertebral discs, and herniated intervertebral discs. The vertebrae and associated connective elements are also susceptible to injuries, including fractures and torn ligaments and further may endure surgical manipulations, including a laminectomy to relieve pressure on the spinal cord or nearby nerves.

The pain and disability related to the diseases and conditions often result from the displacement of all or part of a vertebra from the remainder of the vertebral column. Spinal fusion is a surgical procedure that aims to restore displaced vertebrae to their normal position and to fix those previously displaced vertebrae within the vertebral column. During a spinal fusion procedure, vertebrae are fused together so that relative motion no longer occurs between the fused vertebrae. Typically, a spinal fusion procedure includes removing a damaged intervertebral disc and restoring the spacing between the fused vertebrae, thereby eliminating the instability and removing the pressure on the neurological elements that are causing pain as a result of the disease or condition. The spinal fusion procedure can further include implanting an intervertebral implant between vertebrae, for example adjacent vertebrae, to recreate the natural intervertebral spacing between adjacent vertebrae, previously provided by the damaged and now removed intervertebral disc.

Intervertebral implants and techniques associated with implanting them typically involve an open surgical procedure. An open surgical procedure is any surgical technique where the size of an incision in a patient's body is sufficient to permit the surgical procedure to take place under the direct vision of the surgeon. In other words, the structures and tissues involved can be seen and touched, and they are directly exposed to the air. Open surgical procedures may results in higher cost, lengthy in-patient hospital stays and increased post-operative pain.

An alternative to an open surgical procedure is a minimally invasive surgical procedure, for example a surgical procedure that involves endoscopic techniques. A minimally invasive surgical procedure typically includes accessing the site of pathology through one or more small incisions, with the goal of protecting the integrity of intervening tissues. A minimally invasive surgical procedure may result in reduced post-operative pain, reduced post-operative recovery time, and damage to healthy tissue compared to an open surgical procedure.

Minimally invasive surgical techniques are particularly desirable for spinal and neurosurgical applications because of the need for access to locations deep within the body and the danger of damage to vital intervening tissues. For example, such minimally invasive techniques can be utilized for spinal discectomy, or removal of an intervertebral disc, and spinal fusion, in which two or more vertebrae are fused together to stop the motion between them.

However, in a minimally invasive spinal fusion procedure using an intervertebral implant, the size of the opening in the patient's body must be large enough to accommodate the largest dimension of the intervertebral implant. Additionally, the maximum dimension of the intervertebral implant may limit the approaches available to a surgeon for use during a minimally invasive spinal fusion procedure. These and other short comings of the prior art are addressed by the present disclosure.

SUMMARY

In accordance with an aspect of the disclosure, the present application discloses an implant including a frame including an end member and an intermediate member pivotally coupled to the end member about a first pivot axis. The implant includes a first vertebral contact member pivotally coupled to the frame about a second pivot axis that is substantially perpendicular to the first pivot axis, the first vertebral contact member defining a face configured to engage a first vertebra. The implant includes a second vertebral contact member coupled to the frame, the second vertebral contact member defining a face configured to engage a second vertebra. The frame is configured such that pivoting the intermediate member with respect to the end member about the first pivot axis changes a width between the first vertebral contact member and the second vertebral contact member with respect to a direction that is substantially parallel to the second pivot axis. The frame is also configured such that pivoting the first vertebral contact member with respect to the frame about the second pivot axis changes a height between the first vertebral contact member and the second vertebral contact member with respect to a direction that is substantially parallel to the first pivot axis.

In accordance with an aspect of the disclosure, the present application discloses an implant including a frame including an end member and an intermediate member pivotally coupled to the end member about a first pivot axis. The implant includes a first vertebral contact member pivotally coupled to the frame about a second pivot axis that is substantially perpendicular to the first pivot axis, the first vertebral contact member defining a face configured to engage a first vertebra. The implant includes a second vertebral contact member coupled to the frame, the second vertebral contact member defining a face configured to engage a second vertebra. The frame is configured such that pivoting the intermediate member with respect to the end member about the first pivot axis changes a width of the first vertebral contact member, the width measured along a straight line that is substantially parallel to the second pivot axis. The frame is also configured such that pivoting the first vertebral contact member with respect to the frame about the second pivot axis changes a height measured from the face of the first vertebral contact member to the face of the second vertebral contact member along a straight line that is substantially parallel to the first pivot axis.

In accordance with an aspect of the disclosure, an implant includes a first vertebral contact member defining a face configured to engage a first vertebra, and a second vertebral contact member defining a face configured to engage a second vertebra. The implant includes a frame including an end member, an intermediate member, a first linkage pivotally coupling the end member to the intermediate member such that the end member and the intermediate member are pivotable relative one another about a first pair of pivot axes that are parallel to each other, and a second linkage pivotally coupling the intermediate member to the first vertebral contact member such that the intermediate member and the first vertebral contact member are pivotable relative to one another about a second pair of pivot axes that are parallel to each other and perpendicular to the first pair of pivot axes. The first pair of pivot axes are separated by a first distance as measured along a straight line that is substantially parallel to the second pair of pivot axes, the second pair of pivot axes are separated by a second distance as measured along a straight line that is substantially parallel to the first pair of pivot axes, and the first distance is greater than the second distance.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

FIG. 3A is an isometric view of the intervertebral implant illustrated in FIG. 2, according to an aspect of the disclosure, the intervertebral implant in one configuration;

FIG. 7A is an isometric view of the intervertebral implant illustrated in FIG. 2, according to an aspect of the disclosure, the intervertebral implant in one configuration;

FIG. 7C is a side elevation view of the intervertebral implant illustrated in FIG. 7A, the intervertebral implant in another configuration;

FIG. 7D is another side elevation view of the intervertebral implant illustrated in FIG. 7C;

FIG. 8A is an isometric view of an actuator according to one aspect of the disclosure;

FIG. 8B is a cross-sectional view of the actuator illustrated in FIG. 8A along line 8B-8B, and a first end member of the intervertebral implant;

FIG. 8C is a cross-sectional view of the actuator illustrated in 8A along line 8B-8B, and the first end member of the intervertebral implant;

FIG. 8D is a top plan view of the actuator illustrated in FIG. 8A;

FIG. 8E is a top plan view of an actuator according to another aspect of the disclosure;

FIG. 8F is a side elevation view of an actuator according to another aspect of the disclosure, in one configuration;

FIG. 8G is a side elevation view of the actuator illustrated in FIG. 8G, in another configuration;

FIG. 9 is an isometric view of an implant construct according to one aspect of the disclosure, the implant construct including a first intervertebral implant and a second intervertebral implant;

FIG. 10A is a top plan view of the implant construct implanted in an intervertebral disc space, according to one aspect of the disclosure;

FIG. 10B is a top plan view of the implant construct implanted in an intervertebral disc space, according to another aspect of the disclosure;

DETAILED DESCRIPTION OF ILLUSTRATIVE EMBODIMENTS

Figure 1:
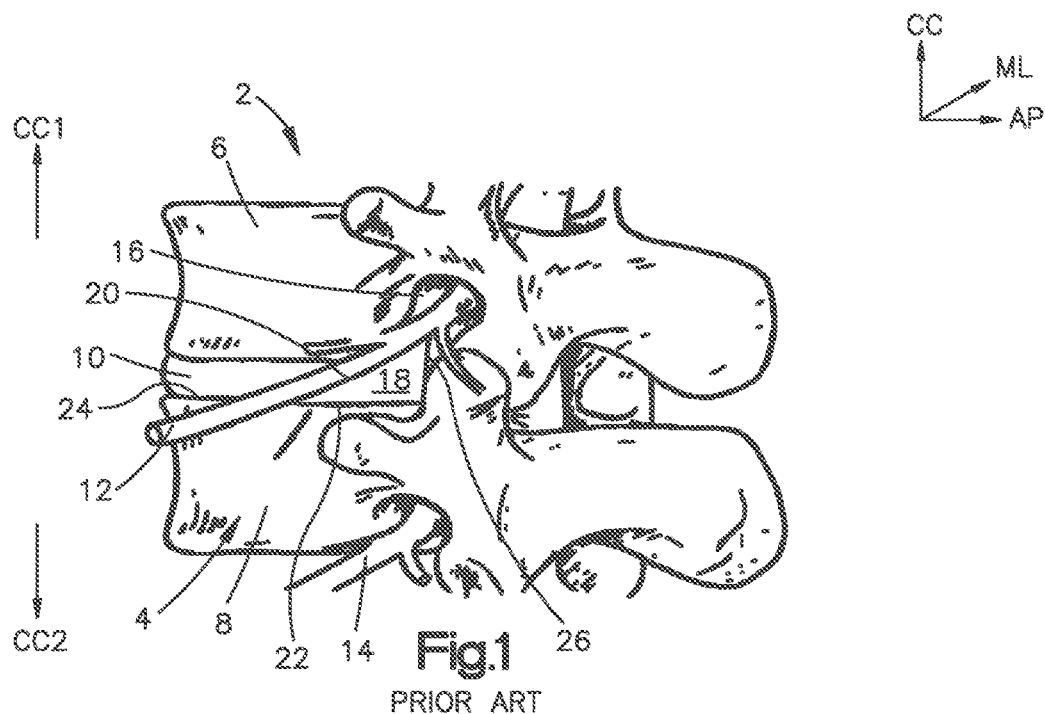
FIG. 1 is a posterolateral view of a region of a spine.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the medical device. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Aspects of the disclosure will now be described in detail with reference to the drawings, wherein like reference numbers refer to like elements throughout, unless specified otherwise. Certain terminology is used in the following description for convenience only and is not limiting. The term "plurality", as used herein, means more than one. The terms "a portion" and "at least a portion" of a structure include the entirety of the structure. Certain features of the disclosure which are described herein in the context of separate embodiments may also be provided in combination in a single embodiment. Conversely, various features of the disclosure that are described in the context of a single embodiment may also be provided separately or in any subcombination.

Reference herein to a first structure being pivotally coupled to or pivoting with respect to a second structure includes each of: 1) the first structure being pivotally coupled to or pivoting with respect to the second structure (such that the first structure moves while the second structure remains stationary); 2) the second structure being pivotally coupled to or pivoting with respect to the first structure (such that the second structure moves while the first structure remains stationary); and 3) both the first structure and the second structure being pivotally coupled to or pivoting with respect to each other (such that both the first structure and the second structure move either simultaneously or sequentially). The term "pivotally coupled" as used herein with respect to first and second structures includes both the first and second structures being directly coupled (such that the respective pivot axis passes through both the first structure and the second structure), and indirectly coupled (such that the respective pivot axis passes through only one of the first and second structures, in addition to passing through an intermediate structure).

A first three dimensional coordinate system is provided in reference to a human body, for example into which an intervertebral implant is to be implanted. The first three dimensional coordinate system includes a cranial-caudal direction CC, a medial-lateral direction ML that is perpendicular to the cranial-caudal direction CC, and an anterior-posterior direction AP that is perpendicular to both the cranial-caudal direction CC and the medial-lateral direction ML. Each of the cranial-caudal direction CC, the medial lateral direction ML, and the anterior-posterior AP is bidirectional. The cranial-caudal direction CC includes a cranial direction CC1 and a caudal direction CC2 that is opposite the cranial direction CC1. The medial-lateral direction ML includes a medial direction and a lateral direction that is opposite the medial direction. The anterior-posterior direction AP includes an anterior direction and a posterior direction that is opposite the anterior direction.

A second three dimensional coordinate system is also provided in reference to a medical device configured to be implanted, for example into a human body. The second three dimensional coordinate system includes a longitudinal direction L, a lateral direction A that is perpendicular to the longitudinal direction L, and a transverse direction T that is perpendicular to both the longitudinal direction L and the lateral direction A.

Referring to FIG. 1, a spine 2, for example a human spine, may include a region 4, and the region 4 includes a superior vertebra 6, an inferior vertebra 8, an intervertebral disc space 10, an exiting nerve root 12, and a traversing nerve root 14. According to one aspect of the disclosure, the superior vertebra 6 is adjacent to the inferior vertebra 8, the inferior vertebra 8 is separated from the superior vertebra 6 in the caudal direction CC2, and the intervertebral disc space 10 is positioned between the superior vertebra 6 and the inferior vertebra 8 with respect to the cranial-caudal direction CC. Further, according to one aspect of the disclosure, the exiting nerve root 12 emerges from a spinal canal 16 between the superior vertebra 6 and the inferior vertebra 8 with respect to the cranial-caudal direction CC, and the traversing nerve root 14 crosses the intervertebral disc space 10 with respect to the cranial-caudal direction CC and emerges from the spinal canal 16 at a location separated from the inferior vertebra 8 in the caudal direction CC2.

The region 4 includes a region known as Kambin's triangle 18. Kambin's triangle 18 is a right triangle positioned over a dorsolateral portion of the intervertebral disc space 10. As shown in the illustrated embodiment, the hypotenuse 20 of Kambin's triangle 18 is defined by the exiting nerve root 12. A first leg 22, also referred to as a base or width, of Kambin's triangle 18 is defined by the superior border 24 of the inferior vertebra 8, and a second leg 26, also referred to as the height, of Kambin's triangle 18 is defined by the traversing nerve root 14.

Kambin's triangle 18 is a known site used during minimally invasive discectomy procedures using a posterolateral approach. Using the posterolateral approach may protect body tissues adjacent to the region from harm during the discectomy procedure. Kambin's triangle 18 defines an approach with a cross-sectional access window at the intervertebral disc space 10 of roughly about 5 mm by about 10 mm. The size limitations imposed by Kambin's triangle 18 restrict the use of instruments and implants with a cross-sectional footprint greater than about 5 mm by about 10 mm in a posterolateral approach. Further, an implant with a cross-sectional footprint equal to or less than about 5 mm by about 10 mm may not provide the stability needed for a solid fusion between the superior vertebra 6 and the inferior vertebra 8. It will be appreciated Referring to FIG. 2, a system 28 includes an implant, for example an intervertebral implant 30, and an insertion instrument 32. The system 28 may be configured to implant the intervertebral implant 30 in the intervertebral disc space 10, for example through Kambin's triangle 18, in an insertion direction ID. The system 28 may further be configured to implant the intervertebral implant 30 into the intervertebral disc space 10 using any other approach, including but not limited to anterior, anterolateral, lateral, extraforaminal, and posterior.

Referring to FIGS. 3A to 3D, the intervertebral implant 30 defines a cross-sectional length L1 measured along the longitudinal direction L, a width W1 measured along the lateral direction A, and a height H1 measured along the transverse direction T. According to one aspect of the disclosure, the length L1 is the maximum dimension of the intervertebral implant 30 as measured along a straight line in the longitudinal direction L, the width W1 is the maximum dimension of the intervertebral implant 30 as measured along a straight line in the lateral direction A, and the height H1 is the maximum dimension of the intervertebral implant 30 as measured along a straight line in the transverse direction T.

Figure 2:
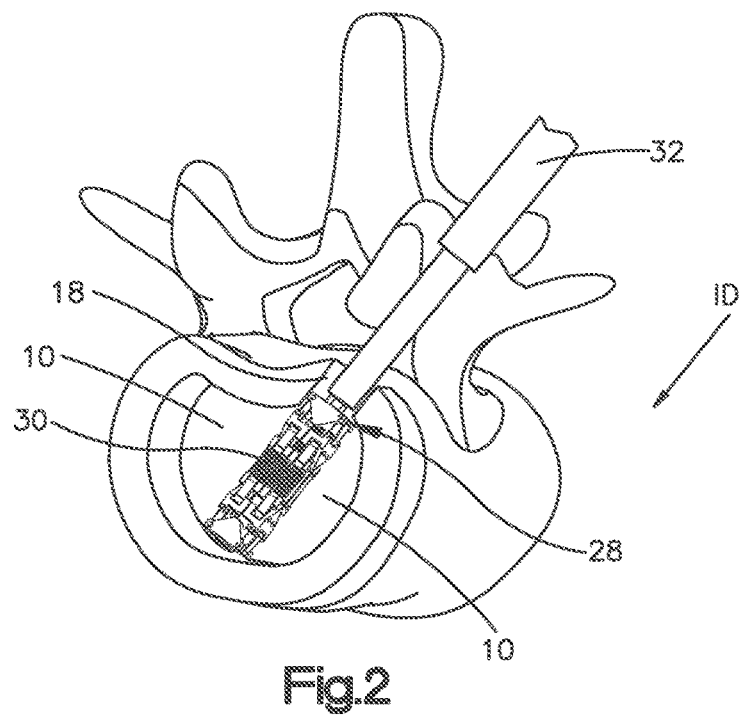
FIG. 2 is an isometric view of an intervertebral implant according to one aspect of the disclosure, being implanted into the region of the spine illustrated in FIG. 1.

Referring to FIGS. 2 and 3A, when the insertion direction ID is aligned with one of the directions of the second three dimensional coordinate system, the intervertebral implant 30 defines a maximum cross-sectional footprint defined by the other two remaining directions of the second three dimensional coordinate system. According to one embodiment of the disclosure, the intervertebral implant 30 is configured to be inserted such that the longitudinal direction L is aligned with the insertion direction ID, and the width W1 and the height H1 define the maximum cross-sectional footprint of the intervertebral implant 30. The intervertebral implant 30 may be configured such that one of the width W1 and the height H1 defines a maximum dimension of about 10 mm or less and the other of the width W1 and the height H1 defines a maximum dimension of about 5 mm or less such that the intervertebral implant 30 is configured to be implanted along a posterolateral approach through Kambin's triangle 18.

Because Kambin's triangle 18 is one of the more restrictive approaches, in regards to the cross-sectional dimensions of any implant being used in an approach through Kambin's triangle 18, if an implant, such as the intervertebral implant 30 is configured to be implanted along a posterolateral approach through Kambin's triangle 18, then the implant will also be configured to be implanted along a great number of other, less restrictive approaches.

Referring to FIGS. 3A to 5B, the intervertebral implant 30 includes an implant body 34 that defines a front end 36 and an opposed rear end 38 separated from the front end 36 along the longitudinal direction L. The implant body 34 further includes opposed sides 40 that are spaced along the lateral direction A. The front end 36 is separated from the rear end 38 in a forward direction, and the rear end 38 is separated from the front end 36 in a rearward direction opposite the forward direction, such that the forward direction and the rearward direction combined define the longitudinal direction L. The implant body 34 further includes a first vertebral contact member 42 and a second vertebral contact member 44 separated from the first vertebral contact member 42 substantially along the transverse direction T. In accordance with the illustrated embodiment, in a first configuration the body 34 is elongate along the longitudinal direction L.

According to one aspect of the disclosure, the implant body 34 further includes a frame 46, and the first vertebral contact member 42 is pivotally coupled to the frame 46 as described in detail below. The frame 46 includes an end member, for example a first end member 48, and an intermediate member, for example a first intermediate member 50, pivotally coupled to the first end member 48. As shown in the illustrated embodiment, the first end member 48 is pivotally coupled to the first intermediate member 50 about a first pivot axis P1. The intervertebral implant 30 may be oriented such that the first pivot axis P1 is substantially parallel to the transverse direction T.

The intervertebral implant 30 is configured such that the first vertebral contact member 42 is pivotally coupled to the frame 46 about a second pivot axis P2 that is substantially perpendicular to the first pivot axis P1. Substantially perpendicular as used herein refers to elements that are exactly perpendicular or nearly perpendicular within manufacturing tolerances. The intervertebral implant 30 may be oriented such that the second pivot axis P2 is substantially parallel to the lateral direction A. The first vertebral contact member 42 defines a face 52 that is configured to directly contact a vertebra, for example the superior vertebra shown in FIG. 1. The second vertebral contact member 44 defines a face 53 that is configured to directly contact a vertebra, for example the inferior vertebra shown in FIG. 1. The face 52, the face 53, or both may be smooth, rough, textured, or toothed to facilitate direct contact with the respective vertebra.

According to one aspect of the disclosure, the frame 46 may be configured such that pivoting the first intermediate member 50 with respect to the first end member 48 about the first pivot axis changes a width W2 between the first vertebral contact member 42 and the second vertebral contact member 44 with respect to a direction that is substantially parallel to the second pivot axis P2. As shown in the illustrated embodiment, the frame 46 may be configured such that pivoting the first intermediate member 50 with respect to the first end member 48 about the first pivot axis changes a width W2 between a portion of the first vertebral contact member 42 and a portion of the second vertebral contact member 44 with respect to the lateral direction A.

According to one aspect of the disclosure, the frame 46 may be configured such that pivoting the first vertebral contact member 42 with respect to the frame 46 about the second pivot axis P2 changes a height H2 between the first vertebral contact member 42 and the second vertebral contact member 44 with respect to a direction that is substantially parallel to the first pivot axis P1. As shown in the illustrated embodiment, the frame 46 may be configured such that pivoting the first vertebral contact member 42 with respect to the frame 46 about the second pivot axis P2 changes a height H2 between a portion of the first vertebral contact member 42 and a portion of the second vertebral contact member 44 with respect to the transverse direction T.

The second vertebral contact member 44 may be pivotally coupled to the frame 46 about a third pivot axis P3 that is substantially parallel to the second pivot axis P2. The frame 46 may be configured such that pivoting the second vertebral contact member 44 with respect to the frame 46 about the third pivot axis P3 changes the height H2 between the first vertebral contact member 42 and the second vertebral contact member 44 with respect to the direction that is substantially parallel to the first pivot axis P1. As shown in the illustrated embodiment, the frame 46 may be configured such that pivoting the second vertebral contact member 44 with respect to the frame 46 about the third pivot axis P3 changes the height H2 between the portion of the first vertebral contact member 42 and the portion of the second vertebral contact member 44 with respect to the transverse direction T.

The frame 46 may include a second end member 54 and a second intermediate member 56 pivotally coupled to the second end member 54 about a fourth pivot axis P4 that is substantially parallel to the first pivot axis P1. The frame 46 may be configured such that pivoting the second intermediate member 56 with respect to the second end member 54 about the fourth pivot axis P4 changes the width W2 between the first vertebral contact member 42 and the second vertebral contact member 44 with respect to the direction that is substantially parallel to the second pivot axis P2. As shown in the illustrated embodiment, the frame 46 may be configured such that pivoting the second intermediate member 56 with respect to the second end member 54 about the fourth pivot axis P4 changes the width W2 between a portion of the first vertebral contact member 42 and a portion of the second vertebral contact member 44 with respect to the lateral direction A.

As shown in the illustrated embodiment, the first vertebral contact member 42 may include a first vertebral contact component 58 and a second vertebral contact component 60 separated from the first vertebral contact component 58 with respect to the direction that is substantially parallel to the second pivot axis P2. The first vertebral contact component 58 may be pivotally coupled to the frame 46 about the second pivot axis P2 and the second vertebral contact component 60 may be pivotally coupled to the frame 46 about a fifth pivot axis P5 that is substantially parallel to the second pivot axis P2. In accordance with one aspect of the disclosure, the second pivot axis P2 and the fifth pivot axis P5 are collinear. Alternatively, the second pivot axis P2 and the fifth pivot axis P5 are offset with respect to a direction perpendicular to the second pivot axis P2, for example the longitudinal direction L.

The frame 46 may be configured such that pivoting the first vertebral contact component 58 with respect to the frame 46 about the second pivot axis P2 changes a height H3 measured between the first vertebral contact component 58 and the second vertebral contact member 44 with respect to the direction that is substantially parallel to the first pivot axis P1. The frame 46 may further be configured such that pivoting the second vertebral contact component 60 with respect to the frame 46 about the fifth pivot axis P5 changes a height H4 between the second vertebral contact component 60 and the second vertebral contact member 44 with respect to the direction that is substantially parallel to the first pivot axis P1. The height H3 may be equal to the height H4, as shown in the illustrated embodiment. Alternatively, the height H3 may be different than, for example either greater than or less than, the height H4.

The second vertebral contact member 44 may include a first vertebral contact component 62 and a second vertebral contact component 64 separated from the first vertebral contact component 62 with respect to the direction that is substantially parallel to the second pivot axis P2. The first vertebral contact component 62 may be pivotally coupled to the frame 46 about the third pivot axis P3 and the second vertebral contact component 64 may be pivotally coupled to the frame 46 about a sixth pivot axis P6 that is substantially parallel to the second pivot axis P2. In accordance with one aspect of the disclosure, the third pivot axis P3 and the sixth pivot axis P6 are collinear. Alternatively, the third pivot axis P3 and the sixth pivot axis P6 are offset with respect to a direction perpendicular to the second pivot axis P2, for example the longitudinal direction L.

The frame 46 may be configured such that pivoting the first vertebral contact component 62 with respect to the frame 46 about the third pivot axis P3 changes the height H3 measured between the first vertebral contact component 58 and the first vertebral contact component 62 with respect to the direction that is substantially parallel to the first pivot axis P1. The frame 46 may further be configured such that pivoting the second vertebral contact component 64 with respect to the frame 46 about the sixth pivot axis P6 changes the height H4 measured between the second vertebral contact component 60 and the second vertebral contact component 64 with respect to the direction that is substantially parallel to the first pivot axis P1. The height H3 may be equal to the height H4, as shown in the illustrated embodiment. Alternatively, the height H3 may be different than, for example either greater than or less than, the height H4.

The implant body 34, for example the frame 46, according to one aspect of the disclosure, includes a plurality of linkages. The plurality of linkages may include a first linkage 66 pivotally coupled to the first end member 48 about the first pivot axis P, and further pivotally coupled to the first intermediate member 50 about a seventh pivot axis P7 that is substantially parallel to the first pivot axis P1. The plurality of linkages may include a second linkage 68 pivotally coupled to the first intermediate member 50 about the second pivot axis P2, and further pivotally coupled to the first vertebral contact member 42 about an eighth pivot axis P8 that is substantially parallel to the second pivot axis P2.

The plurality of linkages may include a third linkage 70 pivotally coupled to the first intermediate member 50 about the third pivot axis P3, and further pivotally coupled to the second vertebral contact member 44 about a ninth pivot axis P9 that is substantially parallel to the third pivot axis P3. The plurality of linkages may include a fourth linkage 72 pivotally coupled to the second end member 54 about the fourth pivot axis P4, and further pivotally coupled to the second intermediate member about a tenth pivot axis P10 that is substantially parallel to the fourth pivot axis P4.

The plurality of linkages may include a fifth linkage 74 pivotally coupled to the second intermediate member 56 about the fifth pivot axis P5, and further pivotally coupled to the first vertebral contact member 42 about a eleventh pivot axis P11 that is substantially parallel to the fifth pivot axis P5. The plurality of linkages may include a sixth linkage 76 pivotally coupled to the second intermediate member 56 about the sixth pivot axis P6, and further pivotally coupled to the second vertebral contact member 44 about a twelfth pivot axis P12 that is substantially parallel to the sixth pivot axis P6.

The intervertebral implant 30 may include a plurality of horizontal linkages that pivot about one or more axes that are substantially parallel to the first pivot axis P1, and a plurality of vertical linkages that pivot about one or more axes that are substantially parallel to the second pivot axis P2. As shown in the illustrated embodiment, the plurality of horizontal linkages includes the first linkage 66 and the fourth linkage 72, and the plurality of vertical linkages includes the second linkage 68, the third linkage, 70, the fifth linkage 74, and the sixth linkage 76.

As shown in the illustrated embodiment, the first intermediate member 50 may include a first intermediate component 78 and a second intermediate component 80 separated from the first intermediate component 78 along the direction that is substantially parallel to the second pivot axis P2. Additionally, the second intermediate member 56 may include a first intermediate component 82 and a second intermediate component 84 separated from the first intermediate component 82 along the direction that is substantially parallel to the second pivot axis P2.

The first linkage 66 may include a first link 86 and a second link 88. As shown in the illustrated embodiment, the first link 86 may be both pivotally coupled to the first end member 48 about the first pivot axis P1, and pivotally coupled to the first intermediate component 78 of the first intermediate member 50 about the seventh pivot axis P7. The second link 88 may be both pivotally coupled to the first end member 48 about a thirteenth pivot axis P13 that is substantially parallel to the first pivot axis P1, and pivotally coupled to the second intermediate component 80 about a fourteenth pivot axis P14 that is substantially parallel to the first pivot axis P1.

The first linkage 66 may further include a first pin 90 pivotally coupling the first link 86 to the first end member 48 about the first pivot axis P1, a second pin 92 pivotally coupling the first link 86 to the first intermediate component 78 about the seventh pivot axis P7, a third pin 94 pivotally coupling the second link 88 to the first end member 48 about the thirteenth pivot axis P13, and a fourth pin 96 pivotally coupling the second link 88 to the second intermediate component 80 about the fourteenth pivot axis P14.

The second linkage 68 may include a first link 98 and a second link 100. As shown in the illustrated embodiment, the first link 98 may be both pivotally coupled to the first intermediate component 78 about the second pivot axis P2, and pivotally coupled to the first vertebral contact component 58 about the eighth pivot axis P8. The second link 100 may be both pivotally coupled to the second intermediate component 80 about a fifteenth pivot axis P15 that is substantially parallel to the second pivot axis P2, and pivotally coupled to the second vertebral contact component 60 about a sixteenth pivot axis P16 that is substantially parallel to the second pivot axis P2.

The second linkage 68 may further include a first pin 102 pivotally coupling the first link 98 to the first intermediate component 78 about the second pivot axis P2, a second pin 104 pivotally coupling the first link 98 to the first vertebral contact component 58 about the eighth pivot axis P8, a third pin 106 pivotally coupling the second link 100 to the second intermediate component 80 about the fifteenth pivot axis P15, and a fourth pin 108 pivotally coupling the second link 100 to the second vertebral contact component 60 about the sixteenth pivot axis P16.

The third linkage 70 may include a first link 110 and a second link 112. As shown in the illustrated embodiment, the first link 110 may be both pivotally coupled to the first intermediate component 82 about the third pivot axis P3, and pivotally coupled to the first vertebral contact component 62 about the ninth pivot axis P9. The second link 112 may be both pivotally coupled to the second intermediate component 84 about a seventeenth pivot axis P17 that is substantially parallel to the second pivot axis P2, and pivotally coupled to the second vertebral contact component 64 about an eighteenth pivot axis P18 that is substantially parallel to the second pivot axis P2.

The third linkage 70 may further include a first pin 114 pivotally coupling the first link 110 to the first intermediate component 82 about the third pivot axis P3, a second pin 116 pivotally coupling the first link 110 to the first vertebral contact component 62 about the ninth pivot axis P9, a third pin 118 pivotally coupling the second link 112 to the second intermediate component 84 about the seventeenth pivot axis P17, and a fourth pin 120 pivotally coupling the second link 112 to the second vertebral contact component 64 about the eighteenth pivot axis P18.

The fourth linkage 72 may include a first link 122 and a second link 124. As shown in the illustrated embodiment, the first link 122 may be both pivotally coupled to the second end member 54 about the fourth pivot axis P4, and pivotally coupled to the first intermediate component 82 about the tenth pivot axis P10. The second link 124 may be both pivotally coupled to the second end member 54 about a nineteenth pivot axis P19 that is substantially parallel to the first pivot axis P1, and pivotally coupled to the second intermediate component 84 about a twentieth pivot axis P20 that is substantially parallel to the first pivot axis P1.

The fourth linkage 72 may further include a first pin 126 pivotally coupling the first link 122 to the second end member 54 about the fourth pivot axis P4, a second pin 128 pivotally coupling the first link 122 to the first intermediate component 82 about the tenth pivot axis P10, a third pin 130 pivotally coupling the second link 124 to the second end member 54 about the nineteenth pivot axis P19, and a fourth pin 132 pivotally coupling the second link 124 to the second intermediate component 84 about the twentieth pivot axis P20.

The fifth linkage 74 may include a first link 134 and a second link 136. As shown in the illustrated embodiment, the first link 134 may be both pivotally coupled to the first intermediate component 82 about the fifth pivot axis P5, and pivotally coupled to the first vertebral contact component 58 about the eleventh pivot axis P11. The second link 136 may be both pivotally coupled to the second intermediate component 84 about a twenty-first pivot axis P21 that is substantially parallel to the second pivot axis P2, and pivotally coupled to the second vertebral contact component 60 about a twenty-second pivot axis P22 that is substantially parallel to the second pivot axis P2.

The fifth linkage 74 may further include a first pin 138 pivotally coupling the first link 134 to the first intermediate component 82 about the fifth pivot axis P5, a second pin 140 pivotally coupling the first link 134 to the first vertebral contact component 58 about the eleventh pivot axis P11, a third pin 142 pivotally coupling the second link 136 to the second intermediate component 84 about the twenty-first pivot axis P21, and a fourth pin 144 pivotally coupling the second link 136 to the second vertebral contact component 60 about the twenty-second pivot axis P22.

The sixth linkage 76 may include a first link 146 and a second link 148. As shown in the illustrated embodiment, the first link 146 may be both pivotally coupled to the first intermediate component 82 about the sixth pivot axis P6, and pivotally coupled to the first vertebral contact component 62 about the twelfth pivot axis P12. The second link 148 may be both pivotally coupled to the second intermediate component 84 about a twenty-third pivot axis P23 that is substantially parallel to the second pivot axis P2, and pivotally coupled to the second vertebral contact component 64 about a twenty-fourth pivot axis P24 that is substantially parallel to the second pivot axis P2.

The sixth linkage 76 may further include a first pin 150 pivotally coupling the first link 146 to the first intermediate component 82 about the sixth pivot axis P6, a second pin 152 pivotally coupling the first link 146 to the first vertebral contact component 62 about the twelfth pivot axis P12, a third pin 154 pivotally coupling the second link 148 to the second intermediate component 84 about the twenty-third pivot axis P23, and a fourth pin 156 pivotally coupling the second link 148 to the second vertebral contact component 64 about the twenty-fourth pivot axis P24.

According to one aspect of the disclosure, at least one of the pivot axes P1-P24 passes through a center of one of the pins. As shown in the illustrated embodiment, each of the pivot axes P1-P24 passes through a center of one of the pins.

Figure 5A:
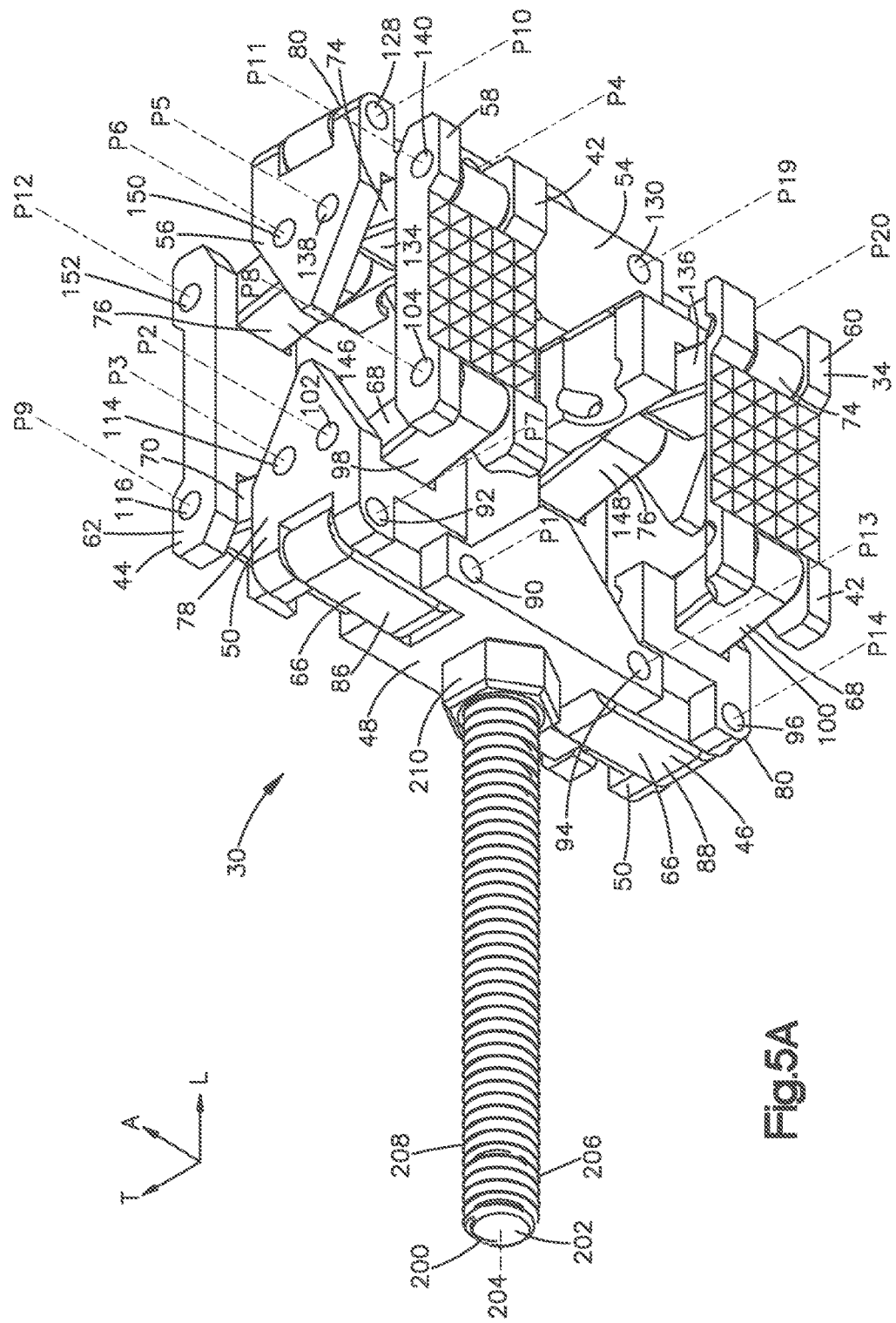
FIG. 5A is an isometric view of the intervertebral implant illustrated in FIG. 3A, the intervertebral implant in another configuration.
Figure 5B:
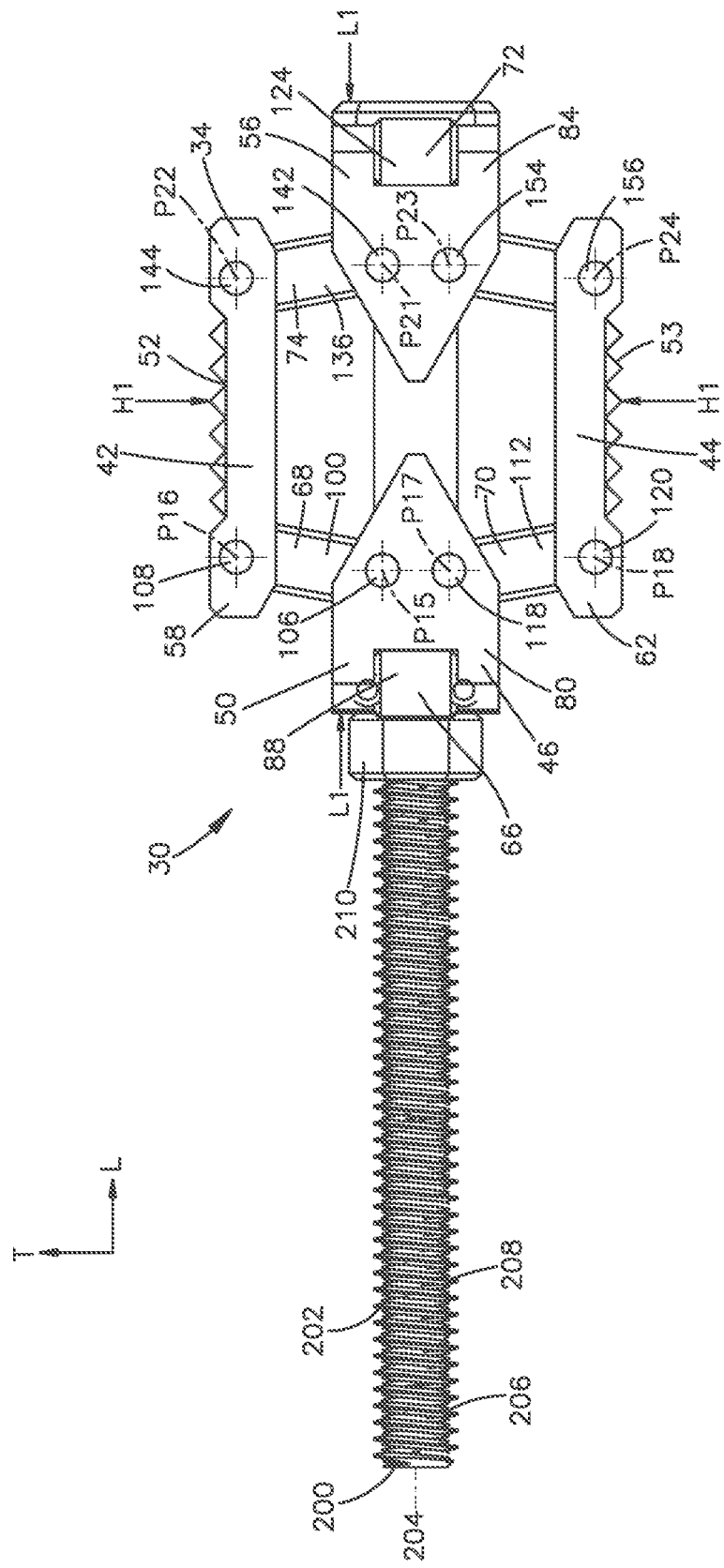
FIG. 5B is a side elevation view of the intervertebral implant illustrated in FIG. 5A.

The intervertebral implant 30 may further include an actuator 200 configured to be actuated to transition the intervertebral implant 30 from a first configuration, for example as shown in FIGS. 3A to 3D, to a second configuration, for example as shown in FIGS. 5A and 5B. When the longitudinal direction L is aligned with the insertion direction ID, the maximum width W1 and the maximum height H1 define the maximum cross-sectional footprint of the intervertebral implant 30. According to one aspect of the disclosure, the maximum width W1 in the first configuration is less than the maximum width W1 in the second configuration, and the maximum height H1 in the first configuration is less than the maximum height H1 in the second configuration. For example, in the first configuration the maximum width W1 is less than or equal to 10 mm and the maximum height H1 is less than or equal to 5 mm, and in the second configuration the maximum width W1 is greater than 10 mm and the maximum height H1 is greater than 5 mm.

Figure 4A:
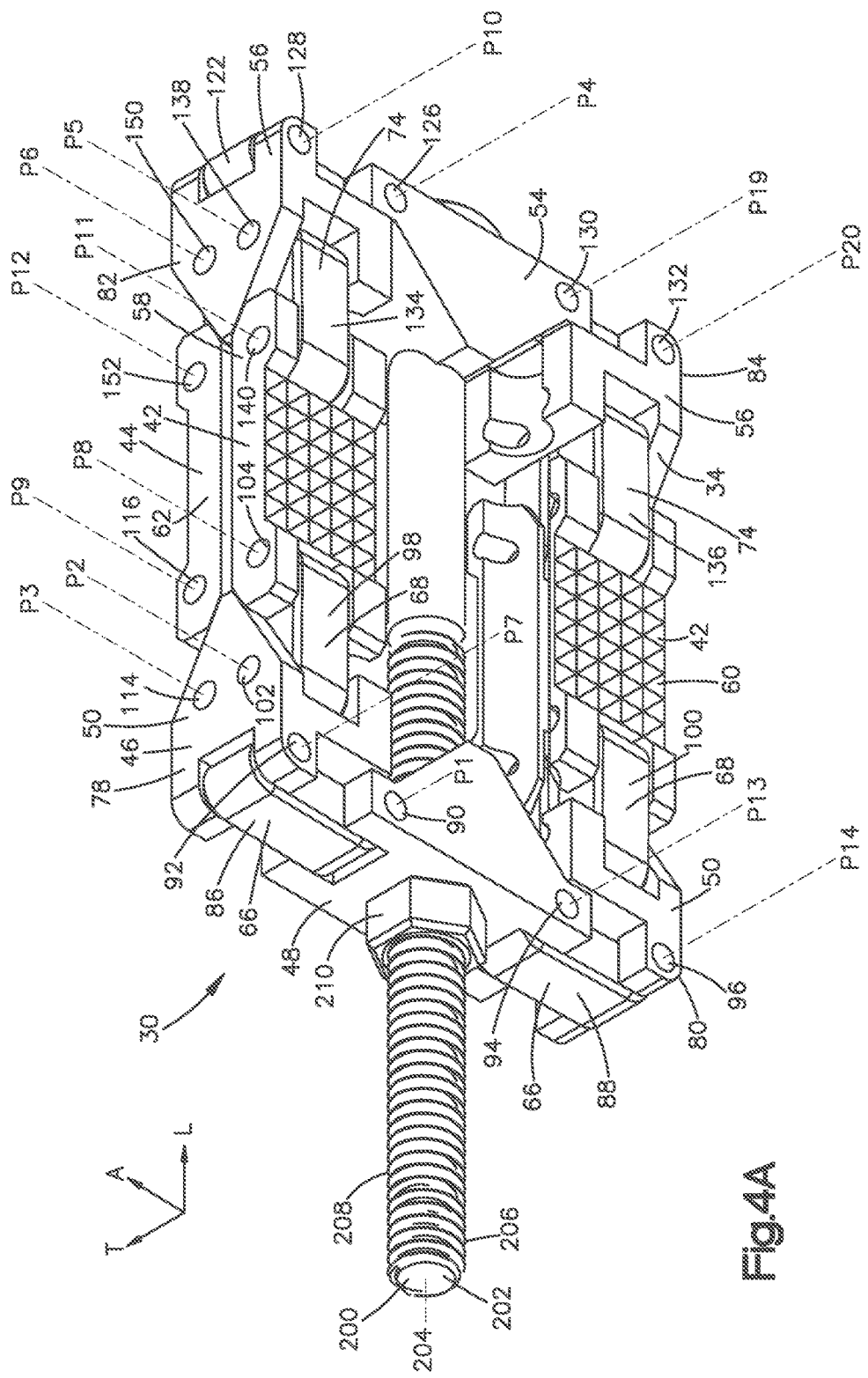
FIG. 4A is an isometric view of the intervertebral implant illustrated in FIG. 3A, the intervertebral implant in another configuration.
Figure 4B:
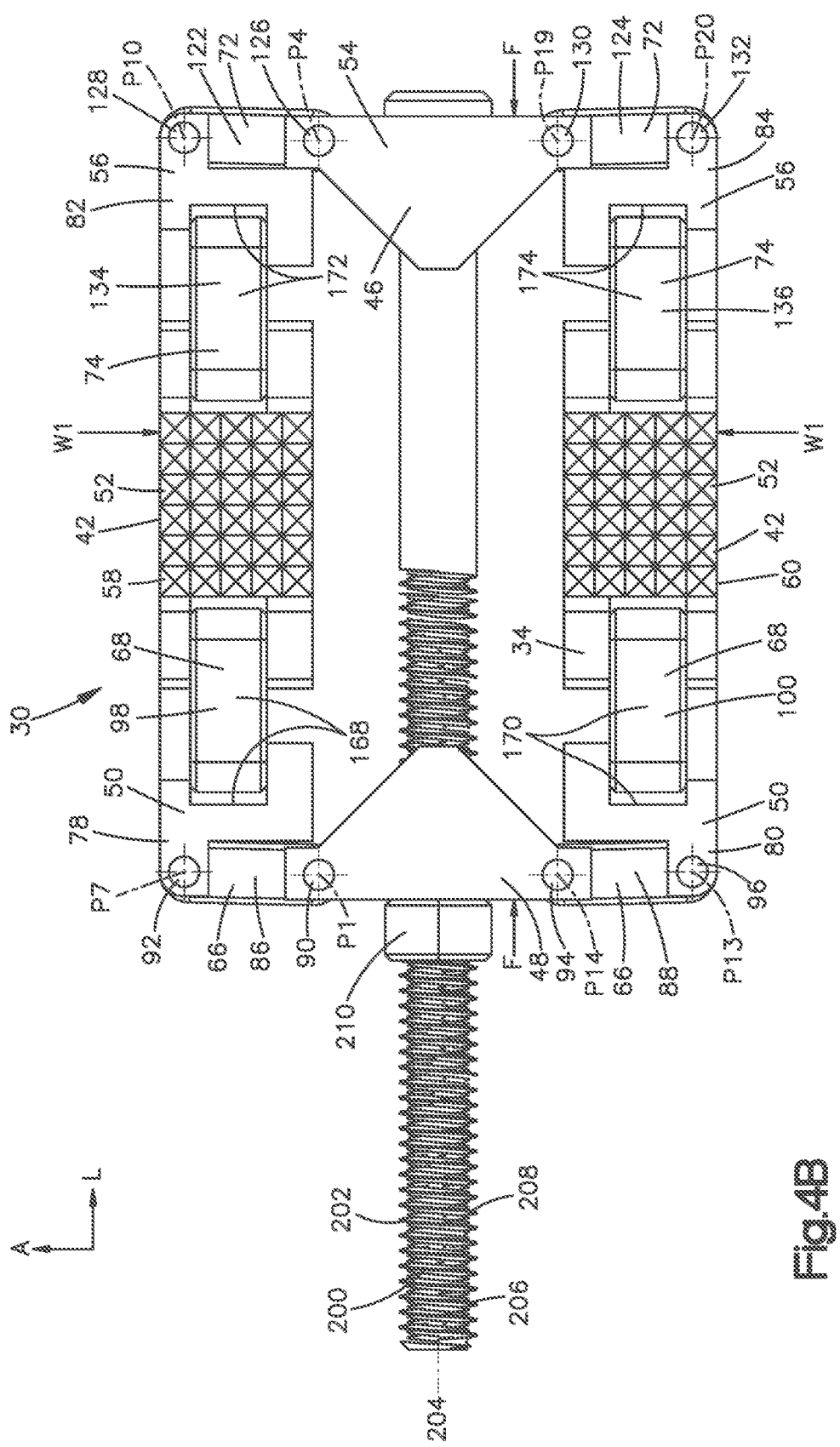
FIG. 4B is a top plan view of the intervertebral implant illustrated in FIG. 4A.

The actuator 200 may further be configured to transition the intervertebral implant 30 from the first configuration to a third configuration, for example as shown in FIGS. 4A and 4B, and from the third configuration to the second configuration. According to one aspect of the disclosure, the maximum width W1 in the third configuration is greater than the maximum width W1 in the first configuration, and the maximum height H1 in the third configuration is substantially equal to the maximum height H1 in the first configuration. Further, the maximum width W1 in the third configuration may be substantially equal to the maximum width W1 in the second configuration, and the maximum height H1 in the third configuration may be less than the maximum height H1 in the second configuration. For example, in the first configuration the maximum width W1 is less than or equal to 10 mm and the maximum height H1 is less than or equal to 5 mm, in the third configuration the maximum width W1 is greater than 10 mm and the maximum height H1 is less than or equal to 5 mm, and in the second configuration the maximum width W1 is greater than 10 mm and the maximum height H1 is greater than 5 mm.

The actuator 200 may be configured to exert a compressive force on the first end member 48 and the second end member 54 such that the compressive force transitions the intervertebral implant 30 from the first configuration to the second configuration, for example through the intermediate third configuration. As shown in the illustrated embodiment, the actuator 200 includes an actuation screw 202 that is elongate along a central axis 204, and the actuation screw 202 includes an outer surface 206 that includes external threads 208 on at least a portion of the outer surface 206. According to one aspect of the disclosure, the actuation screw 202 defines a fixed length as measured along the central axis 204.

The actuation screw 202 may be secured to the frame 46 such that the actuation screw 202 is rotatable about the central axis 204 relative to both the first end member 48 and the second end member 54. The actuation screw 202 may further be secured to the frame 46 such that the central axis 204 is parallel to the longitudinal direction L, the actuation screw 202 is translationally fixed relative to one of the first end member 48 and the second end member 54, and translatable relative to the other of the first end member 48 and the second end member 54.

According to one aspect of the disclosure, the actuation screw 202 is configured to be rotated about the central axis 204 such that the external threads 208 engage the one of the first end member 48 and the second end member 54. For example, the first end member 48 may include internal threads (not shown) that threadedly mate with the external threads 208 of the actuation screw 202. The second end member 54 may be connected, for example journaled, to the actuation screw 202 such that the actuation screw 202 can rotate freely with respect to the second end member 54 about the central axis 204, and the actuation screw 202 is fixed, or cannot translate, with respect to the second end member 54 along a direction parallel to the actuation screw 202.

The actuator 200 may include a locking mechanism 210 configured to, in a locked configuration, prevent actuation of the actuator 200. The locking mechanism 210 may further be configured such that in an unlocked configuration the locking mechanism 210 does not prevent actuation of the actuator 200. As shown in the illustrated embodiment, the locking mechanism 210 may include a nut with internal threads (not shown) that are configured to mate with the external threads 208 of the actuation screw 202. In an unlocked configuration the locking mechanism 210 is spaced from the first end member 48 of the implant body 34 such that the actuator 200 is actuatable to move the first end member 48 either towards or away from the second end member 54 along the longitudinal direction L. In an unlocked configuration the locking mechanism 210 abuts the first end member 48 such that the actuator 200 is not actuatable to move the first member 48 away from the second end member 54 along the longitudinal direction L.

Referring to FIGS. 1 to 5B, in use the actuator 200 is configured to be actuated thereby exerting a compressive force F, in accordance with Newton's third law of motion, on the first end member 48 and the second end member 54 along the longitudinal direction L. Referring to FIGS. 3A to 3D, when the intervertebral implant 30 is in the first configuration as shown, the compressive force F pivots the first intermediate member 50 relative to the first end member 48. In accordance with one embodiment, the compressive force F pivots the first intermediate component 78 relative to the first end member 48 about both the first pivot axis P1 and about the seventh pivot axis P7. The compressive force F further pivots the second intermediate component 80 relative to the first end member 48 about both the thirteenth pivot axis P13 and the fourteenth pivot axis P14, thereby increasing a distance between the first intermediate component 78 and the second intermediate component 80, the distance measured along a straight line parallel to the lateral direction A.

The first end member 48 and the first intermediate member 50 may define a plurality of stop surfaces configured to abut to prevent further pivoting relative to one another. As shown in the illustrated embodiment, the first end member 48 and the first intermediate component 78 collectively define a first pair of stop surfaces 160 and the first end member 48 and the second intermediate component 80 collectively define a second pair of stop surfaces 162.

In accordance with one aspect of the disclosure, the first vertebral contact component 58 and the second vertebral contact component 60 are coupled with the first intermediate component 78 and the second intermediate component 80, respectively, such that as the distance increases between the first intermediate component 78 and the second intermediate component 80, a distance between the first vertebral contact component 58 and the second vertebral contact component 60, measured along a straight line parallel to the lateral direction A, also increases.

The first vertebral contact component 62 and the second vertebral contact component 64 may be coupled with the first intermediate component 78 and the second intermediate component 80, respectively, such that as the distance increases between the first intermediate component 78 and the second intermediate component 80, a distance between the first vertebral contact component 62 and the second vertebral contact component 64, measured along a straight line parallel to the lateral direction A, also increases.

The first vertebral contact component 58 and the second vertebral contact component 60 may be coupled with the first intermediate component 78 and the second intermediate component 80, respectively, and the first vertebral contact component 62 and the second vertebral contact component 64 may be coupled with the first intermediate component 78 and the second intermediate component 80, respectively, such that as the distance increases between the first intermediate component 78 and the second intermediate component 80, a distance between the first vertebral contact component 58 and the second vertebral contact component 64, with respect to the lateral direction A and measured along a straight line parallel to the lateral direction A, also increases.

The compressive force F may further pivot the second intermediate member 56 relative to the second end member 54. In accordance with one embodiment, the compressive force F pivots the first intermediate component 82 relative to the second end member 54 about both the fourth pivot axis P4 and about the tenth pivot axis P10. The compressive force F further pivots the second intermediate component 84 relative to the second end member 54 about both the nineteenth pivot axis P19 and the twentieth pivot axis P20, thereby increasing a distance between the first intermediate component 82 and the second intermediate component 84, the distance measured along a straight line parallel to the lateral direction A.

The second end member 54 and the second intermediate member 56 may define a plurality of stop surfaces configured to abut to prevent further pivoting relative to one another. As shown in the illustrated embodiment, the second end member 54 and the first intermediate component 82 collectively define a third pair of stop surfaces 164 and the second end member 54 and the second intermediate component 84 collectively define a fourth pair of stop surfaces 166.

In accordance with one aspect of the disclosure, the first vertebral contact component 58 and the second vertebral contact component 60 are coupled with the first intermediate component 82 and the second intermediate component 84, respectively, such that as the distance increases between the first intermediate component 82 and the second intermediate component 84, a distance between the first vertebral contact component 58 and the second vertebral contact component 60, measured along a straight line parallel to the lateral direction A, also increases.

The first vertebral contact component 62 and the second vertebral contact component 64 may be coupled with the first intermediate component 82 and the second intermediate component 84, respectively, such that as the distance increases between the first intermediate component 82 and the second intermediate component 84, a distance between the first vertebral contact component 62 and the second vertebral contact component 64, measured along a straight line parallel to the lateral direction A, also increases.

The first vertebral contact component 58 and the second vertebral contact component 60 may be coupled with the first intermediate component 82 and the second intermediate component 84, respectively, and the first vertebral contact component 62 and the second vertebral contact component 64 may be coupled with the first intermediate component 82 and the second intermediate component 84, respectively, such that as the distance increases between the first intermediate component 82 and the second intermediate component 84, a distance between the first vertebral contact component 58 and the second vertebral contact component 64, with respect to the lateral direction A and measured along a straight line parallel to the lateral direction A, also increases.

Referring to FIGS. 3A to 4B, the intervertebral implant 30 is configured such that the compressive force F pivots the first vertebral contact member 42 relative to both the first intermediate member 50 and the second intermediate member 56. According to one embodiment of the disclosure, the compressive force F pivots the first vertebral contact member 42 relative to both the first intermediate member 50 and the second intermediate member 56 after the first pair of stop surfaces 160 abut each other, the second pair of stop surfaces 162 abut each other, the third pair of stop surfaces 164 abut each other, the fourth pair of stop surfaces 166 abut each other, or any combination thereof. As shown in FIGS. 4A and 4B, the first pair of stop surfaces 160 abut each other, the second pair of stop surfaces 162 abut each other, the third pair of stop surfaces 164 abut each other, and the fourth pair of stop surfaces 166 abut each other, and the intervertebral implant 30 is in the third configuration.

In accordance with another embodiment, the compressive force F pivots the first vertebral contact member 42 relative to both the first intermediate member 50 and the second intermediate member 56 prior to the first pair of stop surfaces 160 abutting each other, the second pair of stop surfaces 162 abutting each other, the third pair of stop surfaces 164 abut each other, the fourth pair of stop surfaces 166 abutting each other, or any combination thereof. For example, the intervertebral implant 30 may be configured, for example by changing the friction characteristics of the respective pivot axis, such that pivoting through a first portion of an arc requires less force than pivoting through a second portion of the arc. Thus, the intervertebral implant 30 may be configured such that the compressive force F pivots the first vertebral contact member 42 relative to both the first intermediate member 50 and the second intermediate member 56 prior to the first pair of stop surfaces 160 abutting each other, after the first intermediate member 50 has pivoted relative to the first end member 48 about the first pivot axis P1 through the first portion of an arc, and prior to the first intermediate member 50 pivoting relative to the first end member 48 about the first pivot axis P1 through the second portion of the arc.

Referring to FIGS. 4A to 4B, in accordance with one embodiment, the compressive force F pivots the first vertebral contact component 58 relative to the first intermediate component 78 about both the second pivot axis P2 and about the eighth pivot axis P8, and the compressive force F also pivots the first vertebral contact component 58 relative to the first intermediate component 82 about both the fifth pivot axis P5 and the eleventh pivot axis P11. The compressive force F further pivots the second vertebral contact component 60 relative to the second intermediate component 80 about both the fifteenth pivot axis P15 and the sixteenth pivot axis P16, and also pivots the second vertebral contact component 60 with respect to the second intermediate component 84 about both the twenty-first pivot axis P21 and the twenty-second pivot axis P22, thereby increasing a distance between the first vertebral contact member 42 and the second vertebral contact member 44, the distance measured along a straight line parallel to the transverse direction T.

The second linkage 68 and the first intermediate member 50 may define a plurality of stop surfaces configured to abut to prevent further pivoting relative to one another. As shown in the illustrated embodiment, the first link 98 and the first intermediate component 78 collectively define a fifth pair of stop surfaces 168 and the second link 100 and the second intermediate component 80 collectively define a sixth pair of stop surfaces 170. The fifth linkage 74 and the second intermediate member 56 may define a plurality of stop surfaces configured to abut to prevent further pivoting relative to one another. As shown in the illustrated embodiment, the first link 134 and the first intermediate component 82 may define a seventh pair of stop surfaces 172, and the second link 136 and the second intermediate component 84 may define an eighth pair of stop surfaces 174.

The intervertebral implant 30 may be further configured such that the compressive force F pivots the second vertebral contact member 44 relative to both the first intermediate member 50 and the second intermediate member 56. According to one embodiment of the disclosure, the compressive force F pivots the second vertebral contact member 44 relative to both the first intermediate member 50 and the second intermediate member 56 after the first pair of stop surfaces 160 abut each other, the second pair of stop surfaces 162 abut each other, the third pair of stop surfaces 164 abut each other, the fourth pair of stop surfaces 166 abut each other, or any combination thereof.

The intervertebral implant 30 may be configured such that the compressive force F pivots the second vertebral contact member 44 relative to both the first intermediate member 50 and the second intermediate member 56 and pivots the first vertebral contact member 42 relative to both the first intermediate member 50 and the second intermediate member 56 simultaneously. Alternatively, the intervertebral implant 30 may be configured such that the compressive force F pivots the second vertebral contact member 44 relative to both the first intermediate member 50 and the second intermediate member 56 either before or after the compressive force pivots the first vertebral contact member 42 relative to both the first intermediate member 50 and the second intermediate member 56.

In accordance with one embodiment, the compressive force F pivots the first vertebral contact component 62 relative to the first intermediate component 78 about both the third pivot axis P3 and about the ninth pivot axis P9, and the compressive force F also pivots the first vertebral contact component 62 relative to the first intermediate component 82 about both the sixth pivot axis P6 and the twelfth pivot axis P12. The compressive force F further pivots the second vertebral contact component 64 relative to the second intermediate component 80 about both the seventeenth pivot axis P17 and the eighteenth pivot axis P18, and also pivots the second vertebral contact component 64 with respect to the second intermediate component 84 about both the twenty-third pivot axis P23 and the twenty-fourth pivot axis P24, thereby increasing a distance between the first vertebral contact member 42 and the second vertebral contact member 44, the distance measured along a straight line parallel to the transverse direction T.

Figure 3B:
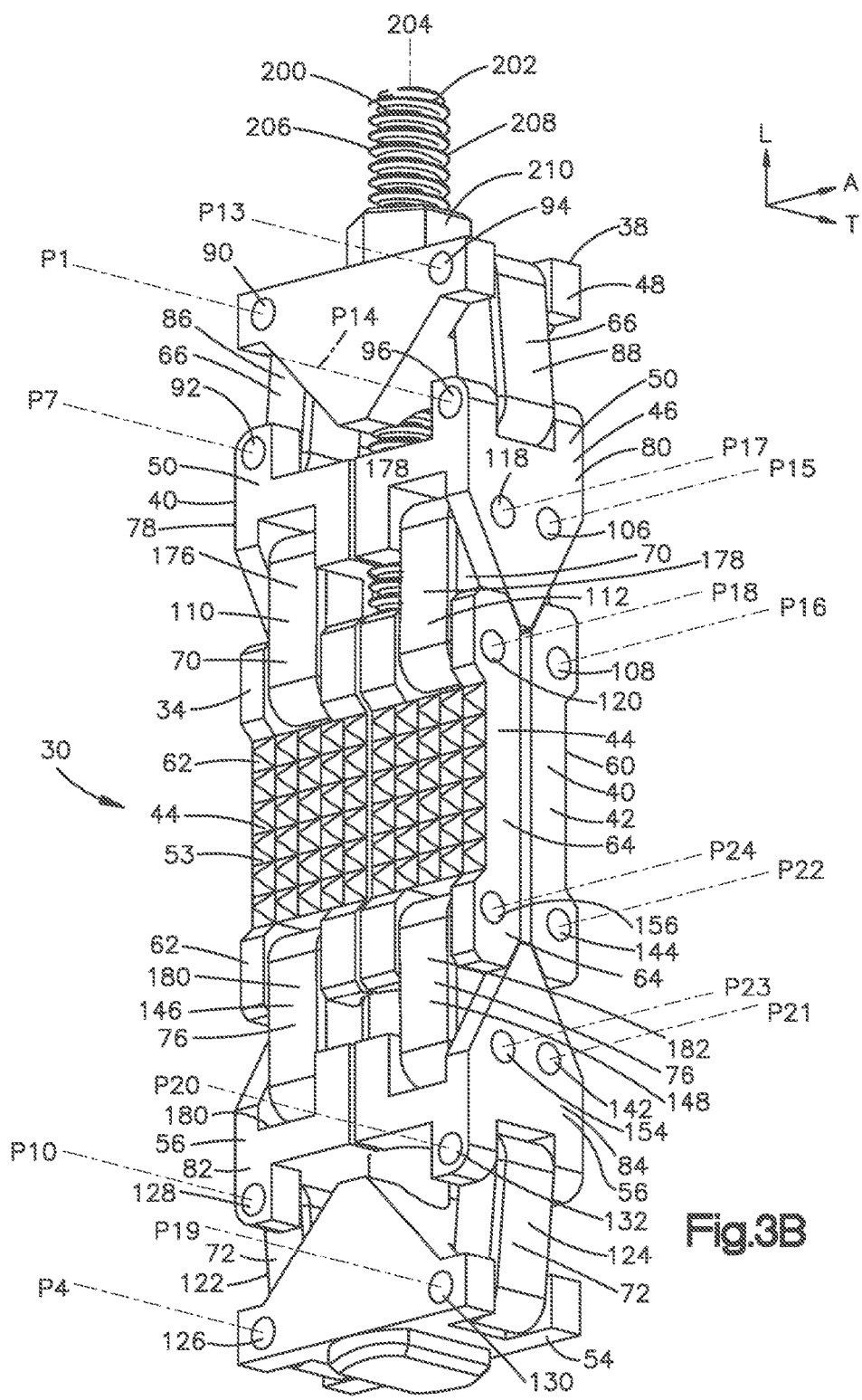
FIG. 3B is another isometric view of the intervertebral implant illustrated in FIG. 3A.

Referring to FIG. 3B, the third linkage 70 and the first intermediate member 50 may define a plurality of stop surfaces configured to abut to prevent further pivoting relative to one another. As shown in the illustrated embodiment, the first link 110 and the first intermediate component 78 collectively define a ninth pair of stop surfaces 176 and the second link 112 and the second intermediate component 80 collectively define a tenth pair of stop surfaces 178. The sixth linkage 76 and the second intermediate member 56 may define a plurality of stop surfaces configured to abut to prevent further pivoting relative to one another. As shown in the illustrated embodiment, the first link 146 and the first intermediate component 82 may define an eleventh pair of stop surfaces 180, and the second link 148 and the second intermediate component 84 may define a twelfth pair of stop surfaces 182.

Referring again to FIGS. 4A and 4B, the intervertebral implant 30 may be configured such that as the compressive force F pivots the first vertebral contact member 42 relative to both the first intermediate member 50 and the second intermediate member 56, pivots the second vertebral contact member 44 relative to both the first intermediate member 50 and the second intermediate member 56, or both, the height H1 of the intervertebral implant 30 changes. For example, when the intervertebral implant 30 is in the third configuration as shown in FIGS. 4A and 4B, and the compressive force F pivots both the first vertebral contact member 42 and the second vertebral contact member 44 relative to both the first intermediate member 50 and the second intermediate member 56, the height H1, measured from the face 52 to the face 53 along a straight line that is parallel to the transverse direction T, increases.

Referring to FIGS. 3A to 5B, according to one embodiment of the disclosure, the intervertebral implant 30 is configured such that when the at least one of the first pair of stop surfaces 160 abut each other, the second pair of stop surfaces 162 abut each other, the third pair of stop surfaces 164 abut each other, the fourth pair of stop surfaces 166 abut each other, and at least one of the fifth pair of stop surfaces 168 abut each other, the sixth pair of stop surfaces 170 abut each other, the seventh pair of stop surfaces 172 abut each other, the eighth pair of stop surfaces 174 abut each other, the ninth pair of stop surfaces 176 abut each other, the tenth pair of stop surfaces 178 abut each other, the eleventh pair of stop surfaces 180 abut each other, and the twelfth pair of stop surfaces 182 abut each other the intervertebral implant 30 is in the second configuration.

For example, the intervertebral implant 30 may be configured such that when the first pair of stop surfaces 160 abut each other, the second pair of stop surfaces 162 abut each other, the third pair of stop surfaces 164 abut each other, the fourth pair of stop surfaces 166 abut each other, the fifth pair of stop surfaces 168 abut each other, the sixth pair of stop surfaces 170 abut each other, the seventh pair of stop surfaces 172 abut each other, the eighth pair of stop surfaces 174 abut each other, the ninth pair of stop surfaces 176 abut each other, the tenth pair of stop surfaces 178 abut each other, the eleventh pair of stop surfaces 180 abut each other and the twelfth pair of stop surfaces 182 abut each other, the intervertebral implant 30 is in the second configuration, as shown in FIGS. 5A and 5B.

Referring to FIGS. 5A and 5B, the height H1 of the intervertebral implant 30 measured from the face 52 to the face 53 along a straight line that is parallel to the transverse direction T, is greater when the intervertebral implant 30 is in the second configuration than the height H1 of the intervertebral implant measured from the face 52 to the face 53 along a straight line that is parallel to the transverse direction T, is greater when the intervertebral implant 30 is in the third configuration (as shown in FIGS. 4A and 4B). The width W1 of the intervertebral implant 30 measured along a straight line that is parallel to the lateral direction A may be equal in the second configuration and the third configuration. The length L1 of the intervertebral implant 30 measured along a straight line that is parallel to the longitudinal direction L may be greater in the third configuration than the second configuration.

Figure 3C:
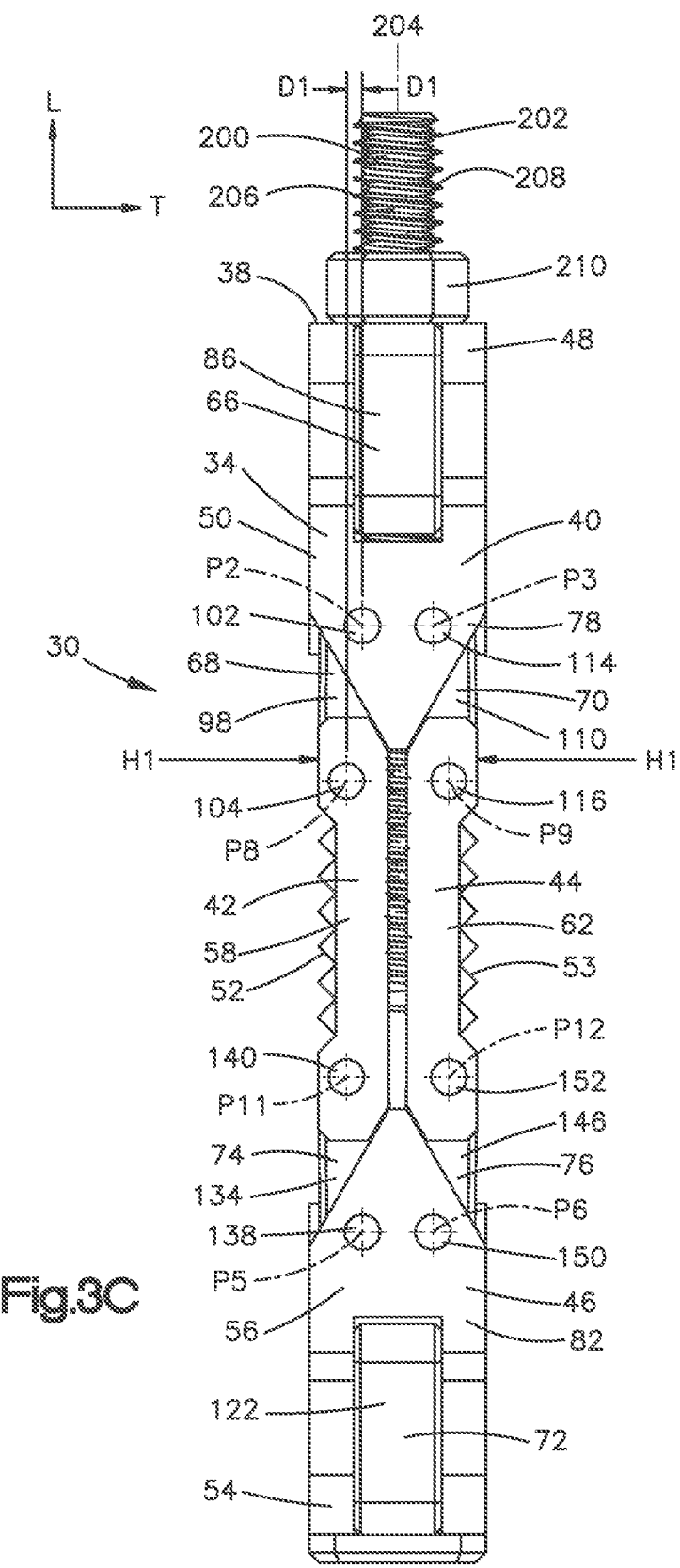
FIG. 3C is a side elevation view of the intervertebral implant illustrated in FIG. 3A.
Figure 3D:
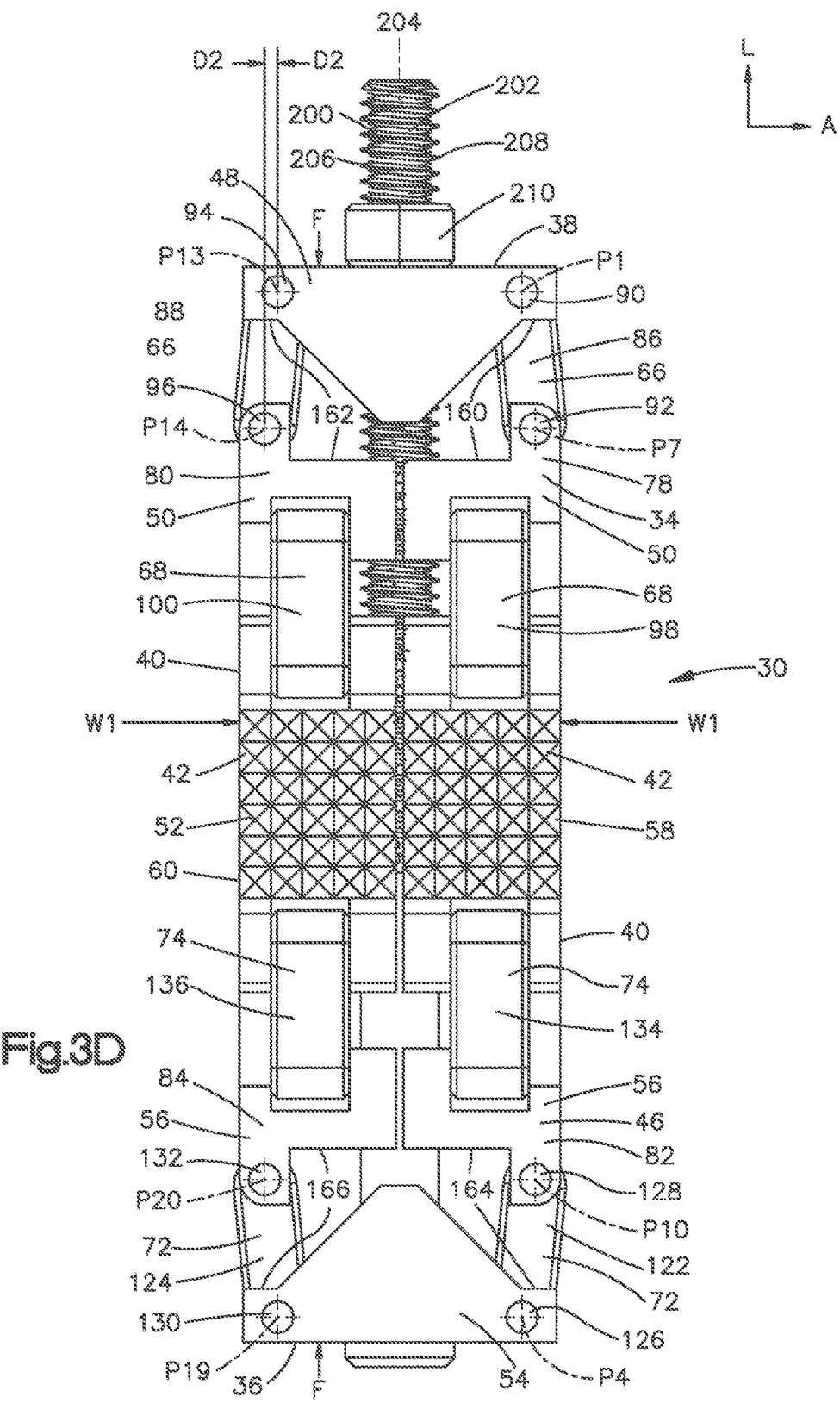
FIG. 3D is a top plan view of the intervertebral implant illustrated in FIG. 3A.

Referring to FIGS. 3C and 3D, the intervertebral implant 30 may be configured such that the compressive force F pivots the plurality of horizontal linkages prior to pivoting the plurality of vertical linkages. Alternatively, the intervertebral implant 30 may be configured such that the compressive force F pivots the plurality of vertical linkages prior to pivoting the plurality of horizontal linkages.

According to one embodiment, the intervertebral implant 30 is configured to be implanted such that resistance provided by the superior vertebra 6 and the inferior vertebra 8 on the intervertebral implant 30 cause the compressive force F to pivot the plurality of horizontal linkages prior to pivoting the plurality of vertical linkages. For example, the implant 30 may be configured such that in an environment devoid of external resistances applied to the intervertebral implant 30, the compressive force F pivots the plurality of horizontal linkages and the plurality of vertical linkages simultaneously.

According to anther embodiment, the intervertebral implant 30 defines a first distance D1 measured between the two pivot axes that pass through one of the links of the plurality of vertical linkages along a straight line that is substantially parallel to the transverse direction T, and the intervertebral implant 30 defines a second distance D2 measured between the two pivot axes that pass through one of the links of the plurality of horizontal linkages along a straight line that is substantially parallel to the lateral direction A. The intervertebral implant 30 may be configured such that when D2 is greater than D1, the compressive force F pivots the plurality of horizontal linkages prior to pivoting the plurality of vertical linkages. The intervertebral implant 30 may be configured such that when D1 is greater than D2, the compressive force F pivots the plurality of vertical linkages prior to pivoting the plurality of horizontal linkages.

For example, if the second distance D2 measured between the thirteenth pivot axis P13 and the fourteenth pivot axis P14 along the lateral direction A is greater than the first distance D1 measured between the second pivot axis P2 and the eighth pivot axis P8 along the transverse direction T, the compressive force F may pivot the second link 88 prior to pivoting the first Referring to FIGS. 3A to 5B, according to one aspect of the disclosure, the intervertebral implant 30 is configured such that the height H1 measured along a straight line that passes through the first vertebral contact component 58, passes through the first vertebral contact component 62, and is parallel to the transverse direction T, is equal to the height H1 measured along a straight line that passes through the second vertebral contact component 60, passes through the second vertebral contact component 64, and is parallel to the transverse direction T. The intervertebral implant 30 with equal heights H1 as described in this paragraph above is referred to herein as having a uniform height.

As shown in the illustrated embodiment, the first and second links, of each of the respective linkages may be equal in length as measured along a straight line that passes perpendicularly through each of the respective pivot axes that pass through the respective link. For example the first link 98 may have a length measured along a straight line that passes perpendicularly through the second pivot axis P2 and the eighth pivot axis P8 that is equal to a length of the link 100 measured along a straight line that passes perpendicularly through the fifteenth pivot axis P15 and the sixteenth pivot axis P16.

Figure 6A:
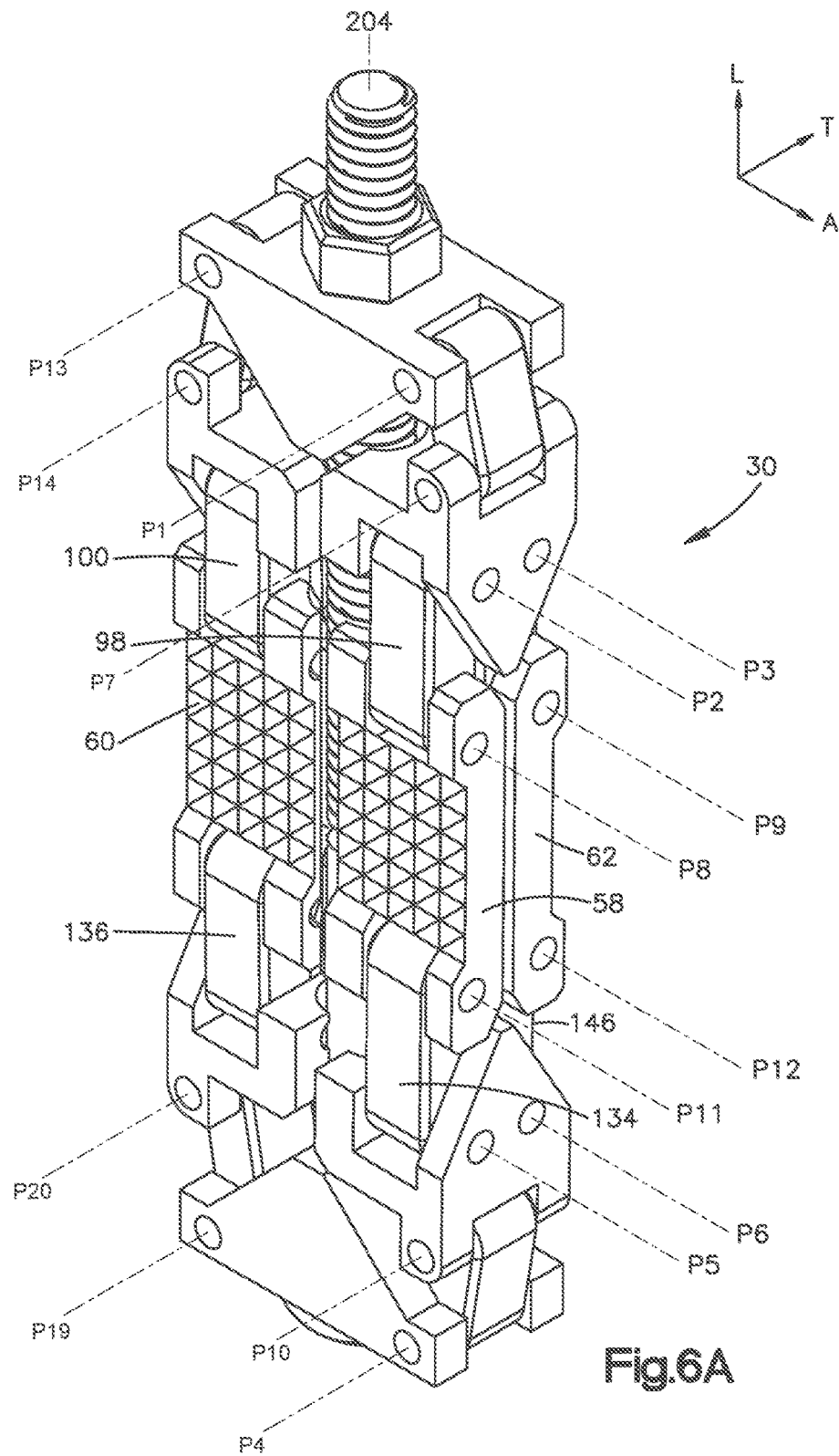
FIG. 6A is an isometric view of the intervertebral implant illustrated in FIG. 2, according to an aspect of the disclosure, the intervertebral implant in one configuration.
Figure 6B:
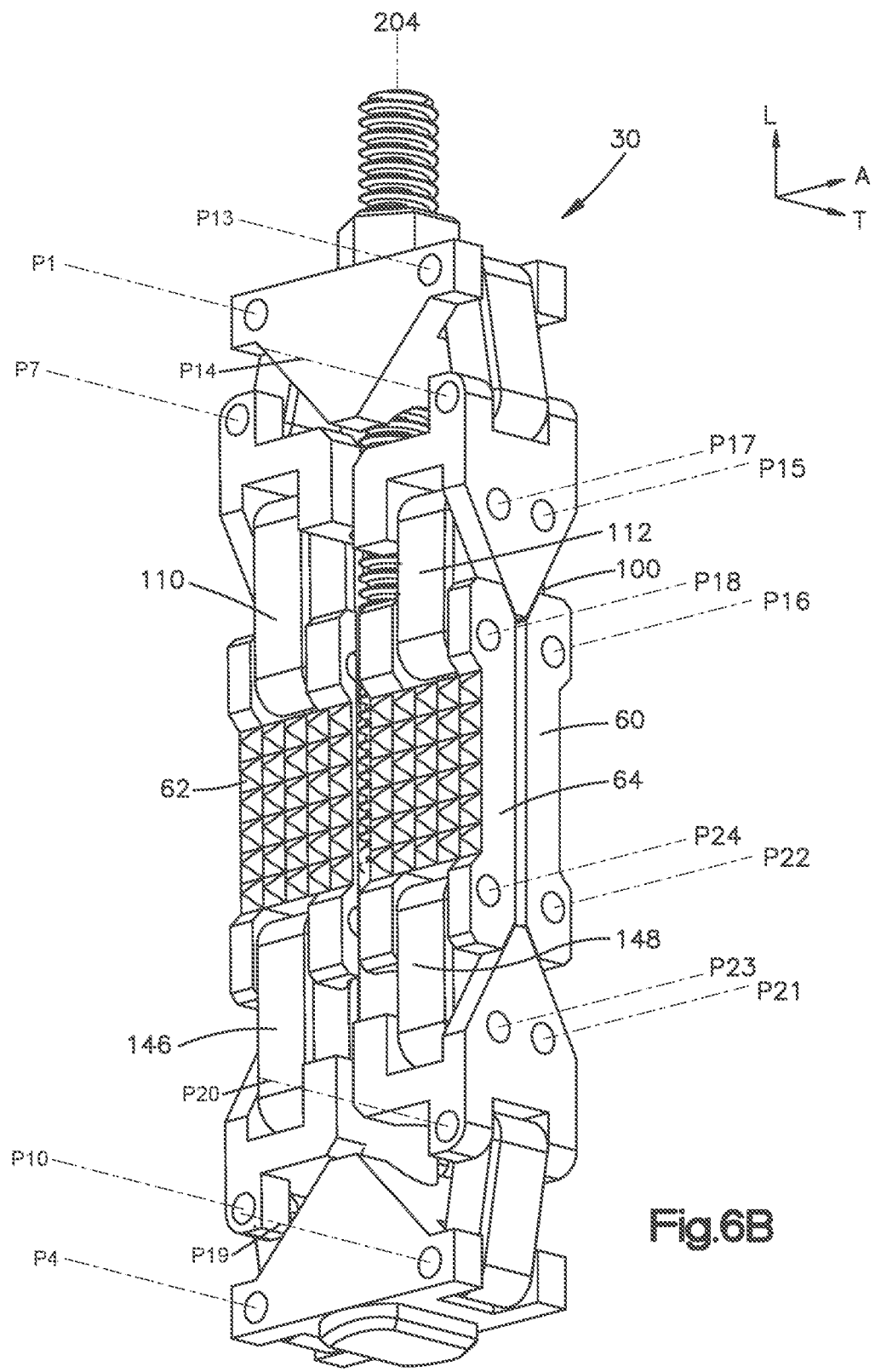
FIG. 6B is another isometric view of the intervertebral implant illustrated in FIG. 6A.
Figure 6C:
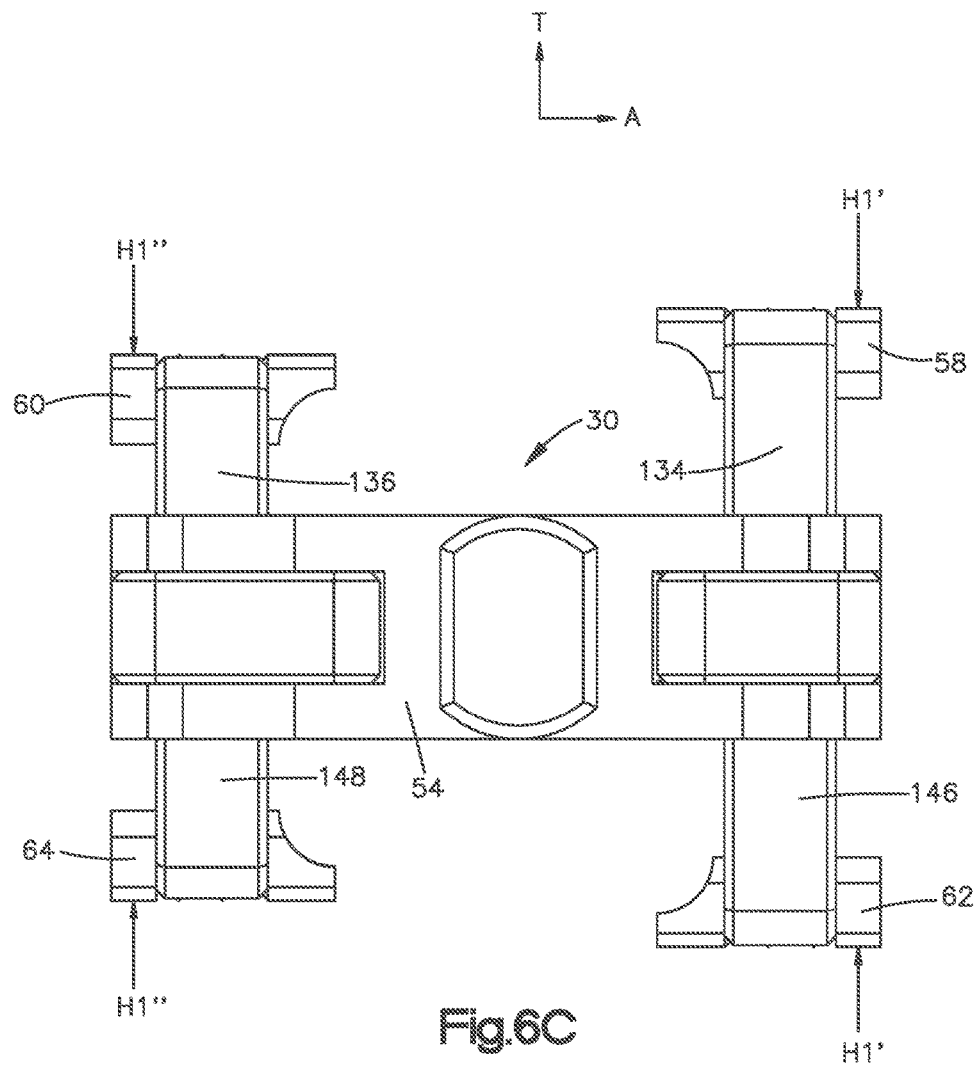
FIG. 6C is a front elevation view of the intervertebral implant illustrated in FIG. 6A, the intervertebral implant in another configuration.
Figure 7B:
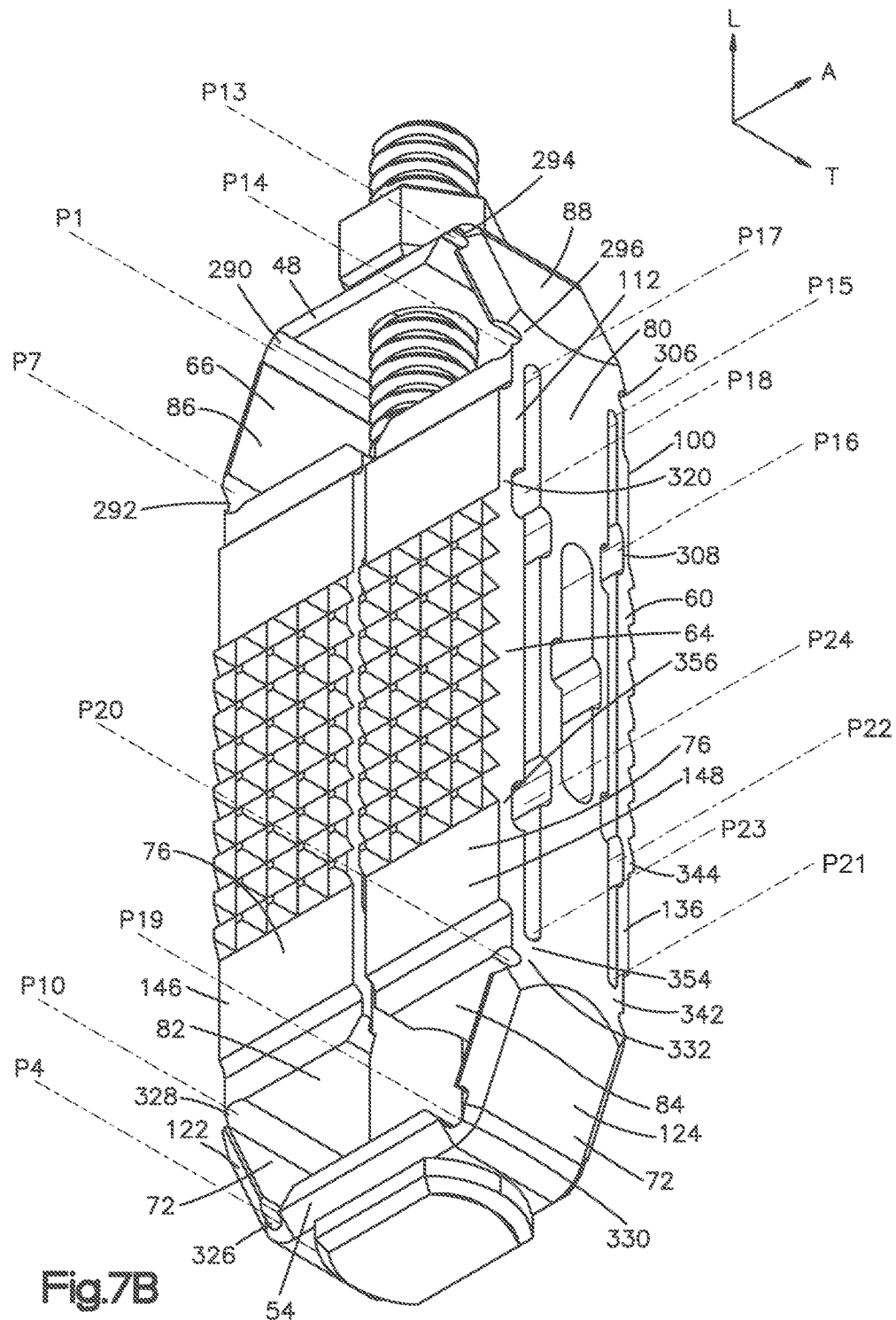
FIG. 7B is another isometric view of the intervertebral implant illustrated in FIG. 7A.

Referring to FIGS. 6A to 6C, the intervertebral implant 30 may be configured such that the height H1' measured along a straight line that passes through the first vertebral contact component 58, passes through the first vertebral contact component 62, and is parallel to the transverse direction T, is different than the height H1" measured along a straight line that passes through the second vertebral contact component 60, passes through the second vertebral contact component 64, and is parallel to the transverse direction T. The intervertebral implant 30 with different heights H1 as described in this paragraph above is referred to herein as having a non-uniform height.

As shown in the illustrated embodiment, the first and second links, of at least some of the respective linkages may have different lengths as measured along a straight line that passes perpendicularly through each of the respective pivot axes that pass through the respective link. For example the first link 98 may have a length measured along a straight line that passes perpendicularly through the second pivot axis P2 and the eighth pivot axis P8 that is different than a length of the link 100 measured along a straight line that passes perpendicularly through the fifteenth pivot axis P15 and the sixteenth pivot axis P16. Additionally, the first link 134 may have a length measured along a straight line that passes perpendicularly through the fifth pivot axis P5 and the eleventh pivot axis P11 that is different than a length of the link 136 measured along a straight line that passes perpendicularly through the twenty-first pivot axis P21 and the twenty-second pivot axis P22.

The intervertebral implant 30 may be configured such that the first link 110 may have a length measured along a straight line that passes perpendicularly through the third pivot axis P3 and the ninth pivot axis P9 that is different than a length of the link 112 measured along a straight line that passes perpendicularly through the seventeenth pivot axis P17 and the eighteenth pivot axis P18. Additionally, the first link 146 may have a length measured along a straight line that passes perpendicularly through the sixth pivot axis P6 and the twelfth pivot axis P12 that is different than a length of the link 148 measured along a straight line that passes perpendicularly through the twenty-third pivot axis P23 and the twenty-fourth pivot axis P24.

The intervertebral implant 30 with a non-uniform height H1 may be used during a spinal fusion procedure being performed on a patient with a curved spine, for example to restore proper lordosis. The non-uniform height H1 of the intervertebral implant 30 may be used to correct the curvature deformity while also fusing the adjacent vertebrae.

Referring to FIGS. 7A to 7D, according to one aspect of the disclosure, the intervertebral implant 30 is configured such that one or more of the linkages includes a deformable portion instead of one or both of the pins of the respective linkage. The deformable portion as described herein may include a portion of the intervertebral implant 30 that is either elastically deformed or plastically deformed. The deformable portion may have a reduced cross-sectional dimension compared to surrounding structures of the intervertebral implant 30.

As shown in the illustrated embodiment, the first linkage 66 may include a first deformable portion 290 pivotally coupling the first link 86 to the first end member 48 about the first pivot axis P1, a second deformable portion 292 pivotally coupling the first link 86 to the first intermediate component 78 about the seventh pivot axis P7, a third deformable portion 294 pivotally coupling the second link 88 to the first end member 48 about the thirteenth pivot axis P13, and a fourth deformable portion 296 pivotally coupling the second link 88 to the second intermediate component 80 about the fourteenth pivot axis P14.

The second linkage 68 may further include a first deformable portion 302 pivotally coupling the first link 98 to the first intermediate component 78 about the second pivot axis P2, a second deformable portion 304 pivotally coupling the first link 98 to the first vertebral contact component 58 about the eighth pivot axis P8, a third deformable portion 306 pivotally coupling the second link 100 to the second intermediate component 80 about the fifteenth pivot axis P15, and a fourth deformable portion 308 pivotally coupling the second link 100 to the second vertebral contact component 60 about the sixteenth pivot axis P16.

The third linkage 70 may further include a first deformable portion 314 pivotally coupling the first link 110 to the first intermediate component 78 about the third pivot axis P3, a second deformable portion 316 pivotally coupling the first link 110 to the first vertebral contact component 62 about the ninth pivot axis P9, a third deformable portion 318 pivotally coupling the second link 112 to the second intermediate component 84 about the seventeenth pivot axis P17, and a fourth deformable portion 320 pivotally coupling the second link 112 to the second vertebral contact component 64 about the eighteenth pivot axis P18.

The fourth linkage 72 may further include a first deformable portion 326 pivotally coupling the first link 122 to the second end member 54 about the fourth pivot axis P4, a second deformable portion 328 pivotally coupling the first link 122 to the first intermediate component 82 about the tenth pivot axis P10, a third deformable portion 330 pivotally coupling the second link 124 to the second end member 54 about the nineteenth pivot axis P19, and a fourth deformable portion 332 pivotally coupling the second link 124 to the second intermediate component 84 about the twentieth pivot axis P20.

The fifth linkage 74 may further include a first deformable portion 338 pivotally coupling the first link 134 to the first intermediate component 82 about the fifth pivot axis P5, a second deformable portion 340 pivotally coupling the first link 134 to the first vertebral contact component 58 about the eleventh pivot axis P11, a third deformable portion 342 pivotally coupling the second link 136 to the second intermediate component 84 about the twenty-first pivot axis P21, and a fourth deformable portion 344 pivotally coupling the second link 136 to the second vertebral contact component 60 about the twenty-second pivot axis P22.

The sixth linkage 76 may further include a first deformable portion 350 pivotally coupling the first link 146 to the first intermediate component 82 about the sixth pivot axis P6, a second deformable portion 352 pivotally coupling the first link 146 to the first vertebral contact component 62 about the twelfth pivot axis P12, a third deformable portion 354 pivotally coupling the second link 148 to the second intermediate component 84 about the twenty-third pivot axis P23, and a fourth deformable portion 356 pivotally coupling the second link 148 to the second vertebral contact component 64 about the twenty-fourth pivot axis P24.

According to one aspect of the disclosure, each of the linkages of the intervertebral implant 30 includes respective first and second deformable portions, such that the implant body 34 may include a single, monolithic structure that includes each of the first end member 48, the second end member 54, the first intermediate member 50, the second intermediate member 56, the first vertebral contact surface 42, the second vertebral contact surface 44, and each of the linkages. Alternatively, the intervertebral implant 30 may be configured such that some of the linkages include respective pins and some of the linkages include respective deformable portions.

Referring to FIGS. 7C and 7D, the intervertebral implant 30 may include a first support member 184 configured to provide support for the first vertebral contact member 42 when the intervertebral implant 30 is in the second configuration. The first support member 184 may include a first support component 186 configured to support, for example directly abut, the first vertebral contact component 58, and further include a second support component 188 configured to support, for example directly abut, the second vertebral contact component 60.

As shown in the illustrated embodiment, the first support component 186 abuts the first vertebral contact component 58 such that the first support component 186 resists movement of the first vertebral contact component 58 towards the first vertebral contact component 62 along the transverse direction T. The second support component 188 similarly may abut the second vertebral contact component 60 such that the second support component 188 resists movement of the second vertebral contact component 60 towards the second vertebral contact component 64 along the transverse direction T.

The intervertebral implant 30 may be configured such that both a first leg 190 of the first support component 186 is parallel to the first link 98, and a second leg 192 of the first support component 186 is parallel to the first link 134, regardless of the current configuration the intervertebral implant 30. The intervertebral implant 30 may be configured such that both a first leg 194 of the second support component 188 is parallel to the second link 100, and a second leg 196 of the second support component 188 is parallel to the second link 136, regardless of the current configuration of the intervertebral implant 30.

The intervertebral implant 30 may include a second support member 284 configured to provide support for the second vertebral contact member 44 when the intervertebral implant 30 is in the second configuration. The second support member 284 may include a first support component 286 configured to support, for example directly abut, the first vertebral contact component 62, and further include a second support component 288 configured to support, for example directly abut, the second vertebral contact component 64.

As shown in the illustrated embodiment, the first support component 286 abuts the first vertebral contact component 62 such that the first support component 286 resists movement of the first vertebral contact component 62 towards the first vertebral contact component 58 along the transverse direction T. The second support component 288 similarly may abut the second vertebral contact component 64 such that the second support component 288 resists movement of the second vertebral contact component 64 towards the second vertebral contact component 60 along the transverse direction T.

The intervertebral implant 30 may be configured such that both a first leg 290 of the first support component 286 is parallel to the first link 110, and a second leg 292 of the first support component 286 is parallel to the first link 146, regardless of the current configuration the intervertebral implant 30. The intervertebral implant 30 may be configured such that both a first leg 294 of the second support component 288 is parallel to the second link 112, and a second leg 296 of the second support component 288 is parallel to the second link 148, regardless of the current configuration of the intervertebral implant 30.

Referring to FIGS. 8A to 8E, the actuator 200 of the intervertebral implant 30 may include an actuation member 212 that is elongate along a central axis 214. According to one aspect of the disclosure, the actuation member 212 includes an outer surface 216 that includes teeth 218 on at least a portion of the outer surface 216.

Referring to FIGS. 3A and 8A to 8E, the actuation member 212 may be secured to the frame 46 such that the actuation member 212 is translatable along the longitudinal direction L relative to the first end member 48 and translationally fixed along the longitudinal direction L relative to the second end member 54. The actuation member 212 may further be secured to the frame 46 such that the central axis 214 is substantially parallel to the longitudinal direction L. According to one aspect of the disclosure, the central axis 214 may be substantially straight, for example as shown in FIG. 8D, such that the central axis 214 is substantially parallel with the longitudinal direction L. Alternatively, the central axis 214 may be curved, for example as shown in FIG. 8E.

Referring to FIGS. 3A and 8A to 8E, the actuation member 212 may be secured to the frame 46 such that the actuation member 212 is translatable along the longitudinal direction L relative to the first end member 48 and translationally fixed along the longitudinal direction L relative to the second end member 54. The actuation member 212 may further be secured to the frame 46 such that the central axis 214 is substantially parallel to the longitudinal direction L. According to one aspect of the disclosure, the central axis 214 may be substantially straight, for example as shown in FIG. 8C, such that the central axis 214 is substantially parallel with the longitudinal direction L. Alternatively, the central axis 214 may be curved, for example as shown in FIG. 8D.

Referring to FIGS. 8B and 8C, according to one aspect of the disclosure, the actuation screw 202 is configured to be translated relative to the first end member 48 along a direction substantially parallel to the central axis 214, thereby applying the compressive force F to the intervertebral implant 30. The actuator 200 may include a locking mechanism 220 configured to prevent actuation of the actuator 200 in a first direction that is parallel to the central axis 214, while allowing actuation of the actuator 200 in a second direction that is opposite the first direction.

As shown in the illustrated embodiment, the locking mechanism 220 includes the teeth 218 on the outer surface 216 of the actuation member 212. The locking mechanism 220 may further include a pawl 222 carried by the first end member 48. The teeth 218 and the pawl 222 may be configured as a one-way ratchet, such that the teeth 218 and the pawl 222 engage such that the actuation member 212 is translatable along a first direction 224 and not translatable along a second direction 226 opposite the first direction 224. For example, the pawl 222 may be configured to cam over the teeth 218 as the actuation member 212 translates relative to the first end member 48 in the first direction 224, and the pawl 222 may further be configured not to cam over the teeth 222 as a force is applied to the actuation member 212 in the second direction 226 thereby blocking movement of the actuation member 212 relative to the first end member 48 in the second direction 226. According to one aspect of the disclosure, the pawl 222 is a separate member attached to the first end member 48 as shown, for example, in FIG. 8B. According to another aspect of the disclosure, the pawl 222 is monolithic with the first end member 48 as shown, for example, in FIG. 8C.

Referring to FIGS. 8F and 8G, according to one embodiment, the actuator 200 may include an actuation screw 402 that is elongate along a central axis 404, and the actuation screw 402 includes an outer surface 406 that includes external threads 408 on at least a portion of the outer surface 406. The actuation screw 402 may include a first portion 410 movable coupled, for example telescopically, to a second portion 412 of the actuation screw 402. As shown in the illustrated embodiments, the actuation screw 402 defines a variable length L2 as measured from a first end 414 of the actuation screw 402 to a second end 416 of the actuation screw 402 along the central axis 404.

Referring to FIGS. 3A, 8F and 8G, The actuation screw 402 may be secured to the frame 46 such that the actuation screw 402 is rotatable about the central axis 404 relative to both the first end member 48 and the second end member 54. The actuation screw 402 may further be secured to the frame 46 such that the central axis 404 is parallel to the longitudinal direction L.

According to one aspect of the disclosure, a portion of the actuation screw 402, for example one of the first portion 410 and the second portion 412, is configured to be rotated about the central axis 404, relative to the other of the first portion 410 and the second portion 412 such that the external threads 408 engage internal threads (not shown) of the second portion 412 so as to change the length L2 of the actuation screw 402. As the length L2 of the actuation screw 402 changes, for example shortens, the actuation screw 402 exerts a compressive force on the first end member 48 and the second end member 54 thereby transitioning the intervertebral implant from one configuration, for example the first configuration, to another configuration, for example the third configuration.

Referring to FIG. 9 a plurality of the intervertebral implant 30 may be configured to be combined with at least one more of the intervertebral implants 30 to form an implant construct 300 that may be inserted into a single intervertebral disc space. As shown in the illustrated embodiment, the implant construct may include two or more identical intervertebral implants 30. Referring to FIGS. 10A and 10B, the implant construct 300 may include a central axis 302 that the implant construct 300 is elongate along. The implant construct 300 may be configured to be inserted into the intervertebral disc space 10 such that the central axis 302 is substantially straight, as shown in FIG. 10A. The implant construct 300 may be configured to be inserted into the intervertebral disc space 10 such that the central axis 302 is not substantially straight, for example substantially curved, as shown in FIG. 10B.

Figure 11A:
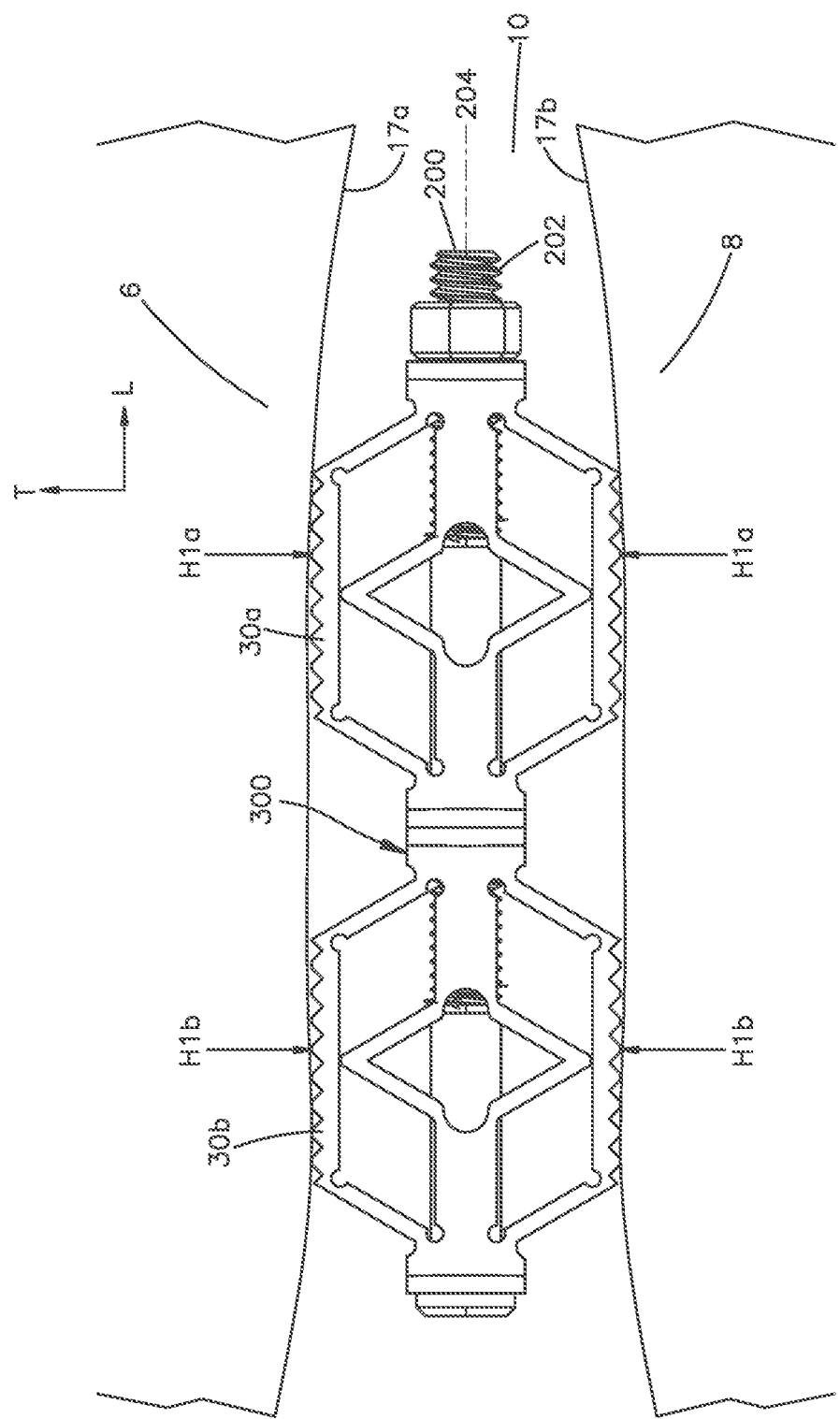
FIG. 11A is a side elevation view of an implant construct according to another aspect of the disclosure implanted in an intervertebral disc space, the implant construct including a first intervertebral implant, and a second intervertebral implant.
Figure 11B:
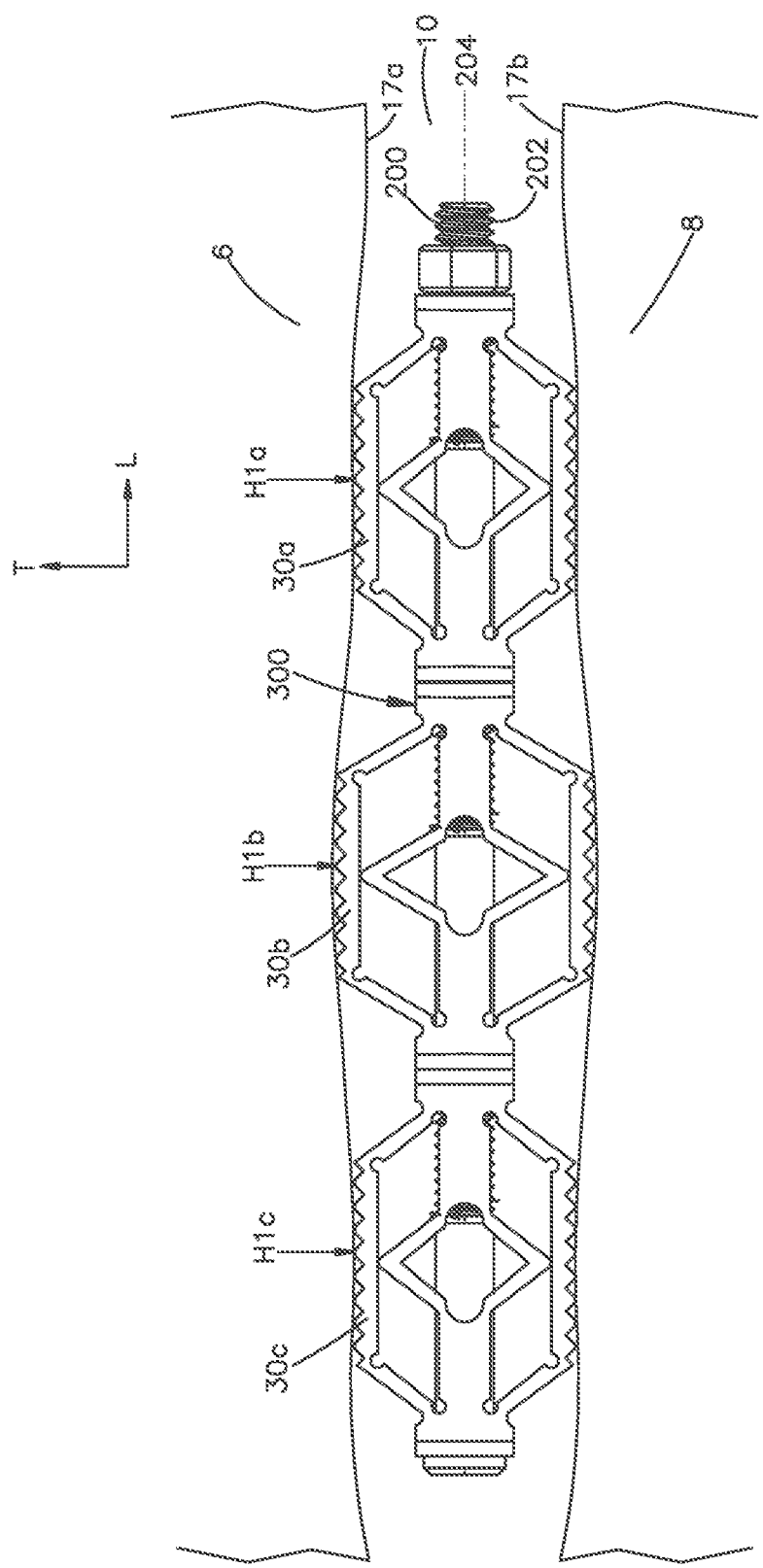
FIG. 11B is a side elevation view of an implant construct according to another aspect of the disclosure implanted in an intervertebral disc space, the implant construct including a first intervertebral implant, a second intervertebral implant, and a third intervertebral implant.

Referring to FIGS. 11A and 11B, the implant construct 300 may include two or more intervertebral implants 30 that are not identical. For example, the implant construct 300 may include a first intervertebral implant 30a that defines a height H a, when the first intervertebral implant 30a is in the second configuration, and a second intervertebral implant 30b that defines a height H1b when the second intervertebral implant 30b is in the second configuration, and the height H1a is different than the height H1b. An implant construct 300 that includes the first intervertebral implant 30a and the second intervertebral implant 30b as descried above may be used during a spinal fusion procedure being performed on a patient with a curved spine, for example a spine with lordosis. The different heights H1a and H1b may be used to correct the curvature deformity while also fusing the adjacent vertebrae.

Referring to FIG. 11B, the implant construct 300 may further include a third intervertebral implant 30c that defines a height H1c that is equal to one of the heights H1a or H1b. The implant construct 300 can be configured such that the height H1c of the third intervertebral implant 30c is substantially equal to the height H1a of the first intervertebral implant 30a, and the height H1b of the second intervertebral implant 30b is greater than both the height H1a and the height H1c. The implant construct 300 may further be configured such that the second intervertebral implant 30b is positioned between the first intervertebral implant 30a and the third intervertebral implant 30c.

Referring to FIGS. 11A and 11B, the implant construct 300 may be configured to match the natural topography of one or both of the endplate 17a of the superior vertebra 6 and the endplate 17b of the inferior vertebra 8 that define the intervertebral disc space 10. The use of the implant construct 300 that is configured to match the natural topography of one or both of the endplate 17a of the superior vertebra 6 and the endplate 17b of the inferior vertebra 8 may lead to an even load distribution across the implant construct 300, a reduction of the risk of subsidence, a reduction of additional fixation devices, such as bone screws, to secure the implant construct 300 in the intervertebral disc space 10, or any combination thereof.

Referring to FIGS. 9 to 11B, the implant construct 300 may include a single actuator 200 configured to transition each of the intervertebral implants 30 included in the implant construct 300 from one configuration to another configuration. For example, the implant construct 300 may include an actuator 200, for example the actuation screw 202, configured such that rotating the actuation screw 202 about the central axis 204, transitions both the first intervertebral implant 30a and the second intervertebral implant 30b from the first configuration to the third configuration, and from the third configuration to the second configuration. According to one aspect of the disclosure, the actuator 200 is configured such that rotating the actuation screw 202 about the central axis 204, transitions both the first intervertebral implant 30*a* and the second intervertebral implant 30*b* from one configuration to another configuration, simultaneously.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An implant comprising:
   a frame including an end member and an intermediate member pivotally coupled to the end member about a first pivot axis;
   a first vertebral contact member pivotally coupled to the frame about a second pivot axis that is substantially perpendicular to the first pivot axis, the first vertebral contact member defining a face configured to engage a first vertebra; and
   a second vertebral contact member coupled to the frame, the second vertebral contact member defining a face configured to engage a second vertebra,
   wherein the frame is configured such that: 1) pivoting the intermediate member with respect to the end member about the first pivot axis changes a width between the first vertebral contact member and the second vertebral contact member with respect to a direction that is substantially parallel to the second pivot axis, and 2) pivoting the first vertebral contact member with respect to the frame about the second pivot axis changes a height between the first vertebral contact member and the second vertebral contact member with respect to a direction that is substantially parallel to the first pivot axis.

2. The implant of claim 1, wherein the second vertebral contact member is pivotally coupled to the frame about a third pivot axis that is substantially parallel to the second pivot axis, and the frame is configured such that pivoting the second vertebral contact member with respect to the frame about the third pivot axis changes the height between the first vertebral contact member and the second vertebral contact member with respect to the direction that is substantially parallel to the first pivot axis.

3. The implant of claim 2, wherein the end member is a first end member, the intermediate member is a first intermediate member, the frame includes a second end member and a second intermediate member pivotally coupled to the second end member about a fourth pivot axis that is substantially parallel to the first pivot axis, and the frame is configured such that pivoting the second intermediate member with respect to the second end member about the fourth pivot axis changes the width between the first vertebral contact member and the second vertebral contact member with respect to the direction that is substantially parallel to the first pivot axis.

4. The implant of claim 3, wherein the first vertebral contact member includes a first vertebral contact component and a second vertebral contact component separated from the first vertebral contact component with respect to the direction that is substantially parallel to the second pivot axis, the first vertebral contact component pivotally coupled to the frame about the second pivot axis, the second vertebral contact component pivotally coupled to the frame about a fifth pivot axis that is substantially parallel to the second pivot axis, and the frame is configured such that: 1) pivoting the first vertebral contact component with respect to the frame about the second pivot axis changes a first height between the first vertebral contact component and the second vertebral contact member with respect to the direction that is substantially parallel to the first pivot axis and 2) pivoting the second vertebral contact component with respect to the frame about the fifth pivot axis changes a second height between the second vertebral contact component and the second vertebral contact member with respect to the direction that is substantially parallel to the first pivot axis.

5. The implant of claim 4, wherein the first height is equal to the second height.

6. The implant of claim 4, wherein the second vertebral contact member includes a first vertebral contact component and a second vertebral contact component separated from the first vertebral contact component of the second vertebral contact member with respect to the direction that is substantially parallel to the second pivot axis, the first vertebral contact component of the second vertebral contact member pivotally coupled to the frame about the third pivot axis, the second vertebral contact component of the second vertebral contact member pivotally coupled to the frame about a sixth pivot axis that is substantially parallel to the second pivot axis, and the frame is configured such that: 1) pivoting the first vertebral contact component of the second vertebral contact member with respect to the frame about the third pivot axis changes the first height between the first vertebral contact component of the first vertebral contact member and the first vertebral contact component of the second vertebral contact member with respect to the direction that is substantially parallel to the first pivot axis and 2) pivoting the second vertebral contact component of the second vertebral contact member with respect to the frame about the sixth pivot axis changes the second height between the second vertebral contact component of the first vertebral contact member and the second vertebral contact component of the second vertebral contact member with respect to the direction that is substantially parallel to the first pivot axis.

7. The implant of claim 6, wherein the first height is different than the second height.

8. The implant of claim 6, further comprising:
a first linkage pivotally coupled to the first end member about the about the first pivot axis, and pivotally coupled to the first intermediate member about a seventh pivot axis that is substantially parallel to the first pivot axis;
a second linkage pivotally coupled to the first intermediate member about the second pivot axis, and pivotally coupled to the first vertebral contact member about an eighth pivot axis that is substantially parallel to the second pivot axis;
a third linkage pivotally coupled to the first intermediate member about the third pivot axis, and pivotally coupled to the second vertebral contact member about a ninth pivot axis that is substantially parallel to the third pivot axis;
a fourth linkage pivotally coupled to the second end member about the about the fourth pivot axis, and pivotally coupled to the second intermediate member about a tenth pivot axis that is substantially parallel to the fourth pivot axis;
a fifth linkage pivotally coupled to the second intermediate member about the fifth pivot axis, and pivotally coupled to the first vertebral contact member about an eleventh pivot axis that is substantially parallel to the fifth pivot axis; and
a sixth linkage pivotally coupled to the second intermediate member about the sixth pivot axis, and pivotally coupled to the second vertebral contact member about a twelfth pivot axis that is substantially parallel to the sixth pivot axis.

9. The implant of claim 8, wherein the first intermediate member includes a first intermediate component and a second intermediate component separated from the first intermediate component along the direction that is substantially parallel to the second pivot axis, and the second intermediate member includes a first intermediate component and a second intermediate component separated from the first intermediate component of the second intermediate member along the direction that is substantially parallel to the second pivot axis.

10. The implant of claim 9, wherein:
the first linkage includes a first link: 1) pivotally coupled to the first end member about the first pivot axis and 2) pivotally coupled to the first intermediate component of the first intermediate member about the seventh pivot axis;
the second linkage includes a first link: 1) pivotally coupled to the first intermediate component of the first intermediate member about the second pivot axis and 2) pivotally coupled to the first vertebral contact component of the first vertebral contact member about the eighth pivot axis;
the third linkage includes a first link: 1) pivotally coupled to the first intermediate component of the second intermediate member about the third pivot axis and 2) pivotally coupled to the first vertebral contact component of the second vertebral contact member about the ninth pivot axis;
the fourth linkage includes a first link: 1) pivotally coupled to the second end member about the fourth pivot axis and 2) pivotally coupled to the first intermediate component of the second intermediate member about the tenth pivot axis;
the fifth linkage includes a first link: 1) pivotally coupled to the first intermediate component of the second intermediate member about the fifth pivot axis and 2) pivotally coupled to the first vertebral contact component of the first vertebral contact member about the eleventh pivot axis; and
the sixth linkage includes a first link: 1) pivotally coupled to the first intermediate component of the second intermediate member about the sixth pivot axis and 2) pivotally coupled to the first vertebral contact component of the second vertebral contact member about the twelfth pivot axis.

11. The implant of claim 10, wherein:
the first linkage includes a second link: 1) pivotally coupled to the first end member about a thirteenth pivot axis that is substantially parallel to the first pivot axis and 2) pivotally coupled to the second intermediate component of the first intermediate member about a fourteenth pivot axis that is substantially parallel to the first pivot axis;
the second linkage includes a second link: 1) pivotally coupled to the second intermediate component of the first intermediate member about a fifteenth pivot axis that is substantially parallel to the second pivot axis and 2) pivotally coupled to the second vertebral contact component of the first vertebral contact member about a sixteenth pivot axis that is substantially parallel to the second pivot axis;
the third linkage includes a second link: 1) pivotally coupled to the second intermediate component of the second intermediate member about a seventeenth pivot axis that is substantially parallel to the second pivot axis and 2) pivotally coupled to the second vertebral contact component of the second vertebral contact member about an eighteenth pivot axis that is substantially parallel to the second pivot axis;
the fourth linkage includes a second link: 1) pivotally coupled to the second end member about a nineteenth pivot axis that is substantially parallel to the first pivot axis and 2) pivotally coupled to the second intermediate component of the second intermediate member about a twentieth pivot axis that is substantially parallel to the first pivot axis;
the fifth linkage includes a second link: 1) pivotally coupled to the second intermediate component of the second intermediate member about a twenty-first pivot axis that is substantially parallel to the second pivot axis and 2) pivotally coupled to the second vertebral contact component of the first vertebral contact member about a twenty-second pivot axis that is substantially parallel to the second pivot axis; and
the sixth linkage includes a second link: 1) pivotally coupled to the second intermediate component of the second intermediate member about a twenty-third pivot axis that is substantially parallel to the second pivot axis and 2) pivotally coupled to the second vertebral contact component of the second vertebral contact member about a twenty-fourth pivot axis that is substantially parallel to the second pivot axis.

12. The implant of claim 11, wherein each of the links is pivotally coupled to the respective component by a pin, and each of the pivot axes passes through a center of one of the pins.

13. The implant of claim 11, wherein each of the links is pivotally coupled to the respective component by a weakened section.

14. The implant of claim 1, further comprising an actuator configured such that actuation of the actuator: 1) pivots the intermediate member with respect to the end member about the first pivot axis and 2) pivots the first vertebral contact member with respect to the frame about the second pivot axis.

15. The implant of claim 14, wherein the actuator is a threaded screw that is actuated by rotating the screw about a central axis of the screw.

16. The implant of claim 14, further comprising a locking mechanism configured to engage the actuator such that actuation of the actuator is prevented in at least one direction.

17. An implant comprising:
a frame including an end member and an intermediate member pivotally coupled to the end member about a first pivot axis;
a first vertebral contact member pivotally coupled to the frame about a second pivot axis that is substantially perpendicular to the first pivot axis, the first vertebral contact member defining a face configured to engage a first vertebra; and
a second vertebral contact member coupled to the frame, the second vertebral contact member defining a face configured to engage a second vertebra,
wherein the frame is configured such that: 1) pivoting the intermediate member with respect to the end member about the first pivot axis changes a width of the first vertebral contact member, the width measured along a straight line that is substantially parallel to the second pivot axis, and 2) pivoting the first vertebral contact member with respect to the frame about the second pivot axis changes a height measured from the face of the first vertebral contact member to the face of the second vertebral contact member along a straight line that is substantially parallel to the first pivot axis.

18. The implant of claim 17, wherein the second vertebral contact member is pivotally coupled to the frame about a third pivot axis that is substantially parallel to the second pivot axis, and the frame is configured such that pivoting the second vertebral contact member with respect to the frame about the third pivot axis changes the height.

19. An implant comprising:
a first vertebral contact member defining a face configured to engage a first vertebra;
a second vertebral contact member defining a face configured to engage a second vertebra; and
a frame including an end member, an intermediate member, a first linkage pivotally coupling the end member to the intermediate member such that the end member and the intermediate member are pivotable relative one another about a first pair of pivot axes that are parallel to each other, and a second linkage pivotally coupling the intermediate member to the first vertebral contact member such that the intermediate member and the first vertebral contact member are pivotable relative to one another about a second pair of pivot axes that are parallel to each other and perpendicular to the first pair of pivot axes,
wherein the first pair of pivot axes are separated by a first distance as measured along a straight line that is substantially parallel to the second pair of pivot axes, the second pair of pivot axes are separated by a second distance as measured along a straight line that is substantially parallel to the first pair of pivot axes, and the first distance is greater than the second distance.

20. The implant of claim 19, further comprising an actuator configured to be actuated such that the end member pivots relative to the intermediate member until a stop surface defined by the end member abuts a stop surface defined by the intermediate member,
wherein the implant is configured such that after the stop surface defined by the end member abuts the stop surface defined by the intermediate member, further actuation of the actuator pivots the first vertebral contact member relative to the intermediate member.

\* \* \* \* \*